(12) United States Patent
Christenson et al.

(10) Patent No.: US 6,599,727 B1
(45) Date of Patent: Jul. 29, 2003

(54) HUMAN POLY (ADP-RIBOSE) POLYMERASE 2 MATERIALS AND METHODS

(75) Inventors: Erik Christenson, Bellevue, WA (US); Anthony J. Demaggio, Kirkland, WA (US); Phyllis S. Goldman, Bothell, WA (US); David L. McElligott, Bothell, WA (US)

(73) Assignee: ICOS Corporation, Bothell, WA (US)

( * ) Notice: Subject to any disclaimer, the term of this patent is extended or adjusted under 35 U.S.C. 154(b) by 75 days.

(21) Appl. No.: 09/596,248

(22) Filed: Jun. 16, 2000

Related U.S. Application Data
(60) Provisional application No. 60/139,543, filed on Jun. 16, 1999.

(51) Int. Cl.$^7$ .......................... C12N 9/12; C12N 15/54; C07H 21/04
(52) U.S. Cl. ...................... 435/194; 435/183; 435/69.1; 435/252.3; 435/254.11; 435/320.1; 536/23.1; 536/23.2; 536/23.5; 530/350
(58) Field of Search ................................ 435/194, 183, 435/252.3, 69.1, 320.1, 254.11; 536/23.1, 23.2, 23.5; 530/350

(56) References Cited

U.S. PATENT DOCUMENTS

| | | | |
|---|---|---|---|
| 3,645,090 A | 2/1972 | Mochizuki et al. | 58/58 |
| 3,691,016 A | 9/1972 | Patel et al. | 195/68 |
| 3,940,475 A | 2/1976 | Gross | 424/1 |
| 3,969,287 A | 7/1976 | Jaworek et al. | 260/8 |
| 4,195,128 A | 3/1980 | Hildebrand et al. | 435/178 |
| 4,229,537 A | 10/1980 | Hodgins et al. | 435/177 |
| 4,247,642 A | 1/1981 | Hirohara et al. | 435/178 |
| 4,302,204 A | 11/1981 | Wahl et al. | 23/230.3 |
| 4,330,440 A | 5/1982 | Ayers et al. | 525/54.31 |
| 4,358,535 A | 11/1982 | Falkow et al. | 435/5 |
| 4,683,195 A | 7/1987 | Mullis et al. | 435/6 |
| 4,687,732 A | 8/1987 | Ward et al. | 435/6 |
| 4,703,004 A | 10/1987 | Hopp et al. | 435/68 |
| 4,711,955 A | 12/1987 | Ward et al. | 536/29 |
| 4,782,137 A | 11/1988 | Hopp et al. | 530/328 |
| 4,800,195 A | 1/1989 | Burgess et al. | 514/150 |
| 4,851,431 A | 7/1989 | Yehuda | 514/560 |
| 4,946,778 A | 8/1990 | Ladner et al. | 435/69.6 |
| 4,965,188 A | 10/1990 | Mullis et al. | 435/6 |
| 5,011,912 A | 4/1991 | Hopp et al. | 530/387 |
| 5,241,060 A | 8/1993 | Engelhardt et al. | 536/27 |
| 5,244,787 A | 9/1993 | Key et al. | 435/7.9 |
| 5,328,824 A | 7/1994 | Ward et al. | 435/6 |
| 5,580,990 A | 12/1996 | van den Berg et al. | 549/212 |
| 5,714,327 A | 2/1998 | Houthoff et al. | 435/6 |

FOREIGN PATENT DOCUMENTS

| | | | | |
|---|---|---|---|---|
| EP | 0 063 879 A2 | 11/1982 | | C07H/19/20 |
| EP | 0 075 444 A2 | 3/1983 | | C12N/15/00 |
| GB | 2 019 404 A | 11/1979 | | C07C/131/00 |
| GB | 2 034 323 A | 6/1980 | | C12N/15/00 |
| WO | WO 91/09955 | 7/1991 | | C12N/15/67 |
| WO | WO 92/20808 | 11/1992 | | C12N/15/85 |
| WO | WO 94/12650 | 6/1994 | | C12N/15/90 |
| WO | WO 99/11623 | 3/1999 | | C07D/217/24 |
| WO | WO 99/11649 | 3/1999 | | C07G/17/00 |
| WO | WO99/64572 | 12/1999 | | C12N/9/10 |

OTHER PUBLICATIONS

Johansson, M.,EMBL/Genbank Data Libraries, Accession No. AF085734, Dec. 1999.*
Cherney et al., cDNA sequence, Protein Structure, and Chromosomal Location of the Human Gene for Poly(AD-P–ribose) Polymerase, Proc. Natl. Acad. Sci. USA vol. 84, pp. 8370–8374, Dec. 1987.*
Alkhatid et al., Cloning and expression of cDNA for Human Poly(ADP–ribose) Polymerase, Proc. Natl. Acad. Sci. USA vol. 84, pp. 1224–1228, Mar. 1987.*
Okayama and Berg, A cDNA Cloning Vector That Permits Expression of cDNA Inserts in Mammalian Cells, Molecular and Cellular Biology, vol. 3, pp. 280–289, Feb. 1983.*
Babiychuk et al., Higher Plants Possess Two Structurally Different Poly(ADP–ribose) Polymerases, The Plant Journal, vol. 15 (5) pp. 635–645, Sep. 1998.*
Althaus and Richter, *ADP–Ribosylation of Proteins: Enzymology and Biochemical Significance*, Molecular Biochemistry and Biophysics, Springer–Verlag (1987).
Amé, J.C. et al. "PARP–2, A Novel Mammalian DNA Damage–dependent Poly(ADP–Ribose) Polymerase", *J. Biol. Chem.* 274(25):17860–17868 (1999).
Anderson, W.F., "Human gene therapy", *Nature*, 392 (6679 Suppl.):25–30.
Ausubel et al., (Eds.), "Screening of Recombinant DNA Libraries", *Current Protocols in Molecular Biology*, John Wiley & Son , Chapter 6, pp. 6.0.3–6.4.10 (1994).
Banasik et al., "Specific Inhibitors of Poly (ADP–Ribose) Synthetase and Mono (ADP–Ribosyl) transferase", *J. Biol. Chem.*, 267:1569–1575 (1992).
Barany, F., "The Ligase Chain Reaction in a PCR World", *PCR Methods and Applications*, 1:5–16 (1991).
Benjamin and Gill, "Poly(ADP–ribose) Synthesis In Vitro Programmed by Damaged DNA", *J. Biol. Chem.*, 255:10502–8 (1980).
Berger and Kimmel, (Eds.) "Guide to Molecular Cloning Techniques," *Methods in Enzymology*, vol. 152, Title Page and Table of Contents Academic Press, San Diego, California (1987).

(List continued on next page.)

*Primary Examiner*—Richard Hutson
(74) *Attorney, Agent, or Firm*—Marshall, Gerstein & Borun

(57) ABSTRACT

The invention provides a novel human poly(ADP-ribose) polymerase (hPARP2) polypeptides, polynucleotides encoding the polypeptides, expression constructs comprising the polynucleotides, and host cells transformed with the expression constructs. Also provided are methods for producing the hPARP2 polypeptides, antibodies that are immunoreactive with the hPARP2 polypeptides. In addition, there are provided methods for identifying specific binding partners of hPARP2, and more particularly methods for identifying binding partners that modulate biological activity of hPARP2. Methods of modulating biological activity of hPARP2 in vitro and in vivo are also provided.

3 Claims, No Drawings

OTHER PUBLICATIONS

Berghammer et al. "pADPRT-2: A Novel mammalian polymerizing (ADP–ribosyl) transfer gene related to truncated pADPRT Homologues in plants and *Caenorhabditis elegans*", *FEBS Lett.* 449:259–263 (1999).

Bramlage et al., "Designing ribozymes for the inhibition of gene expression", *Trends Biotechnol.*, 16:434–438 (1998).

Brüggemann et al., "Strategies for expressing human antibody repertoires in transgenic mice", *Immunol. Today*, 17:391–397 (1996).

Cane et al., "Harnessing the Biosynthetic Code: Combinations, Permutations, and Mutations", *Science*, 282:63–68 (1998).

Capecchi, M.R., "Altering the Genome by Homologous Recombination", *Science*, 244:1288–1292 (1989).

Caruthers, M.H., "Gene Synthesis Machines: DNA Chemistry and Its Uses", *Science*, 230:281–285 (1985).

Caruthers, et al., "Chemical Synthesis of Deoxyoligonucleotides and Deoxyoligonucleotide Analogs", *Methods Enzymol.*, 211:3–20 (1992).

Clackson et al., "Making antibody fragments using phage display libraries", *Nature*, 352:624–628 (1991).

Cline et al., "PCR fidelity of Pfu DNA polymerase and other thermostable DNA polymerases", *Nucleic Acids. Res.*, 24:3546–3551 (1996).

Dall'Acqua et al., "Antibody Engineering", *Curr. Opin. Struct. Biol.*, 8:443–450 (1998).

D'Amours et al., "Purification of the Death Substrate Poly-(ADP–ribose) Polymerase", *Anal. Biochem.*, 249:106–108 (1997).

David et al., "Protein Iodination with Solid State Lactoperoxidase", *Biochemistry*, 13:1014–1021 (1974).

Dayhoff in *Atlas of Protein Sequence and Structure*, National Biochemical Research Foundation, Washington, D.C. 5:124 (1972).

Delihas et al., "Natural antisense RNA/target RNA interactions: Possible models for antisense oligonucleotide drug design", *Nat. Biotechnol.*, 15:751–753 (1997).

Rossomando, E. F., "Ion–Exchange Chromatography", *Methods Enzymol.* (Guide to Protein Chemistry, Section VII) Deutscher, (Eds.) 182:309–421 (1990).

Eguchi, Y., "Antisense RNA", *Annu. Rev. Biochem.*, 60:631–652 (1991).

Fritz et al., "Effect of transfection of human poly(ADP–ribose) polymerase in Chinese hamster cells on mutagen resistance", *Mutation Res.*, 308:127–133 (1994).

Gatti et al., "Localization of an ataxia–telangiectasia gene to chromosome 11q22–23", *Nature*, 336:577–580 (1988).

Sarkar et al., "Restriction–site PCR: A Direct Method of Unknown Sequence Retrieval Adjacent to a Known Locus by Using Universal Primers", *PCR Methods Applic.* 2:319–322 (1993).

Gibson and Shillitoe, "Ribozymes: Their Functions and Strategies for Their Use", *Mol. Biotechnol.*, 7:125–137 (1997).

Harlow, et al., (Eds.) *Antibodies: A Laboratory Manual*, Chapter 6, Cold Spring Harbor Laboratory, Cold Spring Harbor, New York, NY, pp. 139–243 (1988).

Houston and Banks, "The chemical–biological interface: developments in automated and miniaturised screening technology", *Curr. Opin. Biotechnol.*, 8:734–740 (1997).

Hunter et al., "Preparation of Iodine–131 Labelled Human Growth Hormone of High Specific Activity", *Nature*, 194:495–496 (1962).

Huse et al., "Generation of a Large Combinatorial Library of the Immunoglobulin Repertoire in Phage Lambda", *Science*, 246:1275–1281 (1989).

Jayawickreme and Kost, "Gene expression systems in the development of high–throughput screens", *Curr. Opin. Biotechnol.*, 8:629–634 (1997).

Johansson, M. "A Human Poly(ADP–Ribose) Polymerase Gene Family (ADPRTL): cDNA Cloning of Two Novel Poly(ADP–ribose) Polymerase Homologues", *Genomics* 57 (3):442–445 (1999).

Köhler and Milstein, "Continuous cultures of fused cells secreting antibody of predefined specificity", *Nature*, 256:495–497 (1975).

Lagerström et al., "Capture PCR: Efficient Amplification of DNA Fragments Adjacent to a Known Sequence in Human and YAC DNA", *PCR Methods Applic.*, 1:111–119 (1991).

Lamoyi et al., "Preparation of F(ab')$_2$ Fragments from Mouse IgG of Various Subclasses", *J. Immunol. Meth.*, 56:235–243 (1983).

Landegren et al., "A Ligase–Mediated Gene Detection Technique", *Science*, 241:1077–1080 (1988).

Lavrovsky et al., "Therapeutic Potential and Mechanism of Action of Oligonucleotides and Ribozymes", *Biochem. Mol. Med.*, 62:11–22 (1997).

Leary et al., "Rapid and sensitive colorimetric method for visualizing biotin–labeled DNA probes hybridized to DNA or RNA immobilized on nitrocellulose: Bio–blots", *Proc. Nat'l. Acad. Sci. USA*, 80:4045–4049 (1983).

Lo et al., "Inhibition of Poly(ADP–Ribose) Polymerase: Reduction of Ischemic Injury and Attenuation of N–Methyl–D–Aspartate–Induced Neurotransmitter Dysregulation", *Stroke*, 29:830–6 (1998).

Marks et al., "By–passing Immunization Human Antibodies from V–gene Libraries Displayed on Phage", *J. Mol. Biol.*, 222:581–597 (1991).

Meinkoth and Wahl, "Hybridization of Nucleic Acids Immobilized on Solid Supports", *Anal. Biochem.*, 138:267–284 (1984).

Molinete et al., "Structure and Function of the Human poly (ADP–ribose) polymerase" *ADP–Ribosylation Reactions*, Poirier and Moreau (Eds.), Springer–Verlag, New York, p. 3–13, (1992).

Myers, P.L., "Will combinatorial chemistry deliver real medicines?", *Curr. Opin. Biotechnol.*, 8:701–707 (1997).

Nishikimi et al., "Poly(ADP–ribose) Synthetase—The DNA Binding Domain and the Automodification Domain", *J. Biol. Chem.* 257:6102–6105 (1982).

Ouwehand et al., "Novel Diagnostic and Therapeutic Strategies with Genetically Engineered Human Antibodies", *Vox Sang*, 74 (Suppl. 2), 223–232 (1998).

Owens and Young, "The genetic engineering of monoclonal antibodies", *J. Immunological Methods*, 168:149–165 (1994).

Parham, P., "On the Fragmentation of Monoclonal IgG1, IgG2a, and IgG2b from BALB/c Mice", *J. Immunol.*, 131:2895–2902 (1983).

Parker et al., "Targeted gene walking polymerase chain reaction", *Nucleic Acids. Res.*, 19(11):3055–3060 (1991).

Pearson et al., "Improved tools for biological sequence comparison", *Proc. Nat'l. Acad. Sci., USA*, 85:2444–2448 (1988).

Pieper et al., "Poly (ADP–ribose) polymerase, nitric oxide and cell death", *Trends Pharmacol Sci.*, 20:171–181 (1999).

Porath, J., "Immobilized Metal Ion Affinity Chromatography", *Protein Expr. Purif.*, 3:263–281 (1992).

Rader et al., "A phage display approach for rapid antibody humanization: Designed combinatorial V gene libraries", *Proc. Nat'l. Acad. Sci. USA*, 95:8910–8915 (1998).

Renz and Kurz, "A colorimetric method for DNA hybridization", *Nucleic Acids. Res.*, 12:3435–3444 (1984).

Richardson and Gumport, "Biotin and fluorescent labeling of RNA using T4 RNA ligase", *Nucleic Acids. Res.*, 11:6167–6184 (1983).

Roberge et al., "A Strategy for a Convergent Synthesis of N–Linked Glycopeptides on a Solid Support", *Science*, 269:202–204 (1995).

Rotman, B., "Measurement of Activity of Single Molecules of β–D–Galactosidase", *Proc. Nat'l. Acad. Sci. USA*, 47:1981–1991 (1961).

Sambrook et al., (Eds.), *Molecular Cloning:A Laboratory Manual*, Cold Spring Harbor Laboratory Press:Cold Spring Harbor, New York, NY (1989), 9:47–9.50.

Satoh and Lindahl, "Role of poly(ADP–ribose) formation in DNA repair", *Nature*, 356(6367): 356–8 (1992).

Shieh et al., "Poly(ADP–ribose) Polymerase Null Mouse Cells Synthesize ADP–ribose Polymers", *J. Biol. Chem.*, 273(46):30069–30072 (1998).

Sims et al., "Poly(ADP–ribose) Polymerase Inhibitors Preserve Nicotinamide Adenine Dinucleotide and Adenosine 5'–Triphosphate Pools in DNA–Damaged Cells: Mechanism of Stimulation of Unscheduled DNA Synthesis", *Biochemistry*, 22(22):5188–5194 (1983).

Smith, et al., "The synthesis of oligonucleotides containing an aliphatic amino group at the 5' terminus: synthesis of fluorescent DNA primers for use in DNA sequence analysis", *Nucleic Acids Res.*, 13(7):2399–2412 (1985).

Smith, et al., "Tankyrase, a Poly(ADP–Ribose) Polymerase at Human Telomeres", *Science*, 282:1484–1487 (1998).

Szabó, C., "Role of poly(ADP–ribose) synthetase in inflammation", *Eur. J. Pharmacol.*, 350(1):1–19 (1998).

Szabó and Dawson, "Role of poly(ADP–ribose) synthetase in inflammation and ischaemia–reperfusion", *Trends Pharmacol. Sci.*, 19(7):287–298 (1998).

Triglia et al., "A procedure for in vitro amplification of DNA segments that lie outside the boundaries of known sequences", *Nucleic Acids Res.*, 16:8186 (1988).

Tsopanakis et al., "Purification and Properties of Poly(ADP–ribose) Polymerase from Pig–Thymus Nuclei", *Eur. J. Biochem.*, 90:337–45 (1978).

Yamamoto et al., "Streptozotocin and alloxan induce DNA strand breaks and poly(ADP–ribose) synthetase in pancreatic islets", *Nature*, 294(5838):284–286 (1981).

Yoshihara, K., "Complete Dependency of Poly(ADP–Ribose) Synthesis on DNA and its Inhibition by Actinomycin D", *Biochem. Biophys. Res. Commun.*, 47:119–125 (1972).

Youssoufian and Lodish, "Transcriptional Inhibition of the Murine Erythropoietin Receptor Gene by an Upstream Repetitive Element", *Mol;. Cell Biol.*, 13(1):98–104(1993).

Hodgkin et al., "The Nematode *Casnorhabditis elegans* and Its Genome", *Science* 270:410 (1995).

* cited by examiner

SEQUENCE LISTING

<160> NUMBER OF SEQ ID NOS: 68

<210> SEQ ID NO 1
<211> LENGTH: 1814
<212> TYPE: DNA
<213> ORGANISM: Homo sapiens
<220> FEATURE:
<221> NAME/KEY: CDS
<222> LOCATION: (63)..(1811)

<400> SEQUENCE: 1

```
gcctagtgac actgggcccg cgattccttg gagcgggttg atgacgtcag cgttcgaatt        60 cc atg gcg gcg cgg cgg cga cgg agc acc ggc ggc ggc agg gcg aga          107
   Met Ala Ala Arg Arg Arg Arg Ser Thr Gly Gly Gly Arg Ala Arg
   1               5                  10                  15 gca tta aat gaa agc aaa aga gtt aat aat ggc aac acg gct cca gaa         155
Ala Leu Asn Glu Ser Lys Arg Val Asn Asn Gly Asn Thr Ala Pro Glu
                20                  25                  30 gac tct tcc cct gcc aag aaa act cgt aga tgc cag aga cag gag tcg         203
Asp Ser Ser Pro Ala Lys Lys Thr Arg Arg Cys Gln Arg Gln Glu Ser
            35                  40                  45 aaa aag atg cct gtg gct gga gga aaa gct aat aag gac agg aca gaa         251
```

```
                Lys Lys Met Pro Val Ala Gly Gly Lys Ala Asn Lys Asp Arg Thr Glu
                         50                  55                  60 gac aag caa gat ggt atg cca gga agg tca tgg gcc agc aaa agg gtc         299
Asp Lys Gln Asp Gly Met Pro Gly Arg Ser Trp Ala Ser Lys Arg Val
 65                  70                  75 tct gaa tct gtg aag gcc ttg ctg tta aag ggc aaa gct cct gtg gac         347
Ser Glu Ser Val Lys Ala Leu Leu Leu Lys Gly Lys Ala Pro Val Asp
 80                  85                  90                  95 cca gag tgt aca gcc aag gtg ggg aag gct cat gtg tat tgt gaa gga         395
Pro Glu Cys Thr Ala Lys Val Gly Lys Ala His Val Tyr Cys Glu Gly
                    100                 105                 110 aat gat gtc tat gat gtc atg cta aat cag acc aat ctc cag ttc aac         443
Asn Asp Val Tyr Asp Val Met Leu Asn Gln Thr Asn Leu Gln Phe Asn
                115                 120                 125 aac aac aag tac tat ctg att cag cta tta gaa gat gat gcc cag agg         491
Asn Asn Lys Tyr Tyr Leu Ile Gln Leu Leu Glu Asp Asp Ala Gln Arg
            130                 135                 140 aac ttc agt gtt tgg atg aga tgg ggc cga gtt ggg aaa atg gga cag         539
Asn Phe Ser Val Trp Met Arg Trp Gly Arg Val Gly Lys Met Gly Gln
            145                 150                 155 cac agc ctg gtg gct tgt tca ggc aat ctc aac aag gcc aag gaa atc         587
His Ser Leu Val Ala Cys Ser Gly Asn Leu Asn Lys Ala Lys Glu Ile
160                 165                 170                 175 ttt cag aag aaa ttc ctt gac aaa acg aaa aac aat tgg gaa gat cga         635
Phe Gln Lys Lys Phe Leu Asp Lys Thr Lys Asn Asn Trp Glu Asp Arg
                180                 185                 190 gaa aag ttt gag aag gtg cct gga aaa tat gat atg cta cag atg gac         683
Glu Lys Phe Glu Lys Val Pro Gly Lys Tyr Asp Met Leu Gln Met Asp
                195                 200                 205 tat gcc acc aat act cag gat gaa gag gaa aca aag aaa gag gaa tct         731
Tyr Ala Thr Asn Thr Gln Asp Glu Glu Glu Thr Lys Lys Glu Glu Ser
                210                 215                 220 ctt aaa tct ccc ttg aag cca gag tca cag cta gat ctt cgg gta cag         779
Leu Lys Ser Pro Leu Lys Pro Glu Ser Gln Leu Asp Leu Arg Val Gln
225                 230                 235 gag tta ata aag ttg atc tgt aat gtt cag gcc atg gaa gaa atg atg         827
Glu Leu Ile Lys Leu Ile Cys Asn Val Gln Ala Met Glu Glu Met Met
240                 245                 250                 255 atg gaa atg aag tat aat acc aag aaa gcc cca ctt ggg aag ctg aca         875
Met Glu Met Lys Tyr Asn Thr Lys Lys Ala Pro Leu Gly Lys Leu Thr
                260                 265                 270 gtg gca caa atc aag gca ggt tac cag tct ctt aag aag att gag gat         923
Val Ala Gln Ile Lys Ala Gly Tyr Gln Ser Leu Lys Lys Ile Glu Asp
                275                 280                 285 tgt att cgg gct ggc cag cat gga cga gct ctc atg gaa gca tgc aat         971
Cys Ile Arg Ala Gly Gln His Gly Arg Ala Leu Met Glu Ala Cys Asn
                290                 295                 300 gaa ttc tac acc agg att ccg cat gac ttt gga ctc cgt act cct cca        1019
Glu Phe Tyr Thr Arg Ile Pro His Asp Phe Gly Leu Arg Thr Pro Pro
305                 310                 315 cta atc cgg aca cag aag gaa ctg tca gaa aaa ata caa tta cta gag        1067
Leu Ile Arg Thr Gln Lys Glu Leu Ser Glu Lys Ile Gln Leu Leu Glu
320                 325                 330                 335 gct ttg gga gac att gaa att gct att aag ctg gtg aaa aca gag cta        1115
Ala Leu Gly Asp Ile Glu Ile Ala Ile Lys Leu Val Lys Thr Glu Leu
                340                 345                 350 caa agc cca gaa cac cca ttg gac caa cac tat aga aac cta cat tgt        1163
Gln Ser Pro Glu His Pro Leu Asp Gln His Tyr Arg Asn Leu His Cys
                355                 360                 365
```

-continued

```
gcc ttg cgc ccc ctt gac cat gaa agt tac gag ttc aaa gtg att tcc      1211
Ala Leu Arg Pro Leu Asp His Glu Ser Tyr Glu Phe Lys Val Ile Ser
        370                 375                 380 cag tac cta caa tct acc cat gct ccc aca cac agc gac tat acc atg      1259
Gln Tyr Leu Gln Ser Thr His Ala Pro Thr His Ser Asp Tyr Thr Met
385                 390                 395 acc ttg ctg gat ttg ttt gaa gtg gag aag gat ggt gag aaa gaa gcc      1307
Thr Leu Leu Asp Leu Phe Glu Val Glu Lys Asp Gly Glu Lys Glu Ala
400                 405                 410                 415 ttc aga gag gac ctt cat aac agg atg ctt cta tgg cat ggt tcc agg      1355
Phe Arg Glu Asp Leu His Asn Arg Met Leu Leu Trp His Gly Ser Arg
            420                 425                 430 atg agt aac tgg gtg gga atc ttg agc cat ggg ctt cga att gcc cca      1403
Met Ser Asn Trp Val Gly Ile Leu Ser His Gly Leu Arg Ile Ala Pro
            435                 440                 445 cct gaa gct ccc atc aca ggt tac atg ttt ggg aaa gga atc tac ttt      1451
Pro Glu Ala Pro Ile Thr Gly Tyr Met Phe Gly Lys Gly Ile Tyr Phe
                450                 455                 460 gct gac atg tct tcc aag agt gcc aat tac tgc ttt gcc tct cgc cta      1499
Ala Asp Met Ser Ser Lys Ser Ala Asn Tyr Cys Phe Ala Ser Arg Leu
465                 470                 475 aag aat aca gga ctg ctg ctc tta tca gag gta gct cta ggt cag tgt      1547
Lys Asn Thr Gly Leu Leu Leu Leu Ser Glu Val Ala Leu Gly Gln Cys
480                 485                 490                 495 aat gaa cta cta gag gcc aat cct aag gcc gaa gga ttg ctt caa ggt      1595
Asn Glu Leu Leu Glu Ala Asn Pro Lys Ala Glu Gly Leu Leu Gln Gly
                500                 505                 510 aaa cat agc acc aag ggg ctg ggc aag atg gct ccc agt tct gcc cac      1643
Lys His Ser Thr Lys Gly Leu Gly Lys Met Ala Pro Ser Ser Ala His
                515                 520                 525 ttc gtc acc ctg aat ggg agt aca gtg cca tta gga cca gca agt gac      1691
Phe Val Thr Leu Asn Gly Ser Thr Val Pro Leu Gly Pro Ala Ser Asp
            530                 535                 540 aca gga att ctg aat cca gat ggt tat acc ctc aac tac aat gaa tat      1739
Thr Gly Ile Leu Asn Pro Asp Gly Tyr Thr Leu Asn Tyr Asn Glu Tyr
545                 550                 555 att gta tat aac ccc aac cag gtc cgt atg cgg tac ctt tta aag gtt      1787
Ile Val Tyr Asn Pro Asn Gln Val Arg Met Arg Tyr Leu Leu Lys Val
560                 565                 570                 575 cag ttt aat ttc ctt cag ctg tgg tga                                   1814
Gln Phe Asn Phe Leu Gln Leu Trp
                580

<210> SEQ ID NO 2
<211> LENGTH: 583
<212> TYPE: PRT
<213> ORGANISM: Homo sapiens

<400> SEQUENCE: 2

Met Ala Ala Arg Arg Arg Ser Thr Gly Gly Arg Ala Arg Ala
1               5                   10                  15

Leu Asn Glu Ser Lys Arg Val Asn Asn Gly Asn Thr Ala Pro Glu Asp
                20                  25                  30

Ser Ser Pro Ala Lys Lys Thr Arg Arg Cys Gln Arg Gln Glu Ser Lys
            35                  40                  45

Lys Met Pro Val Ala Gly Gly Lys Ala Asn Lys Asp Arg Thr Glu Asp
        50                  55                  60

Lys Gln Asp Gly Met Pro Gly Arg Ser Trp Ala Ser Lys Arg Val Ser
65                  70                  75                  80
```

-continued

```
Glu Ser Val Lys Ala Leu Leu Lys Gly Lys Ala Pro Val Asp Pro
                 85                  90                  95

Glu Cys Thr Ala Lys Val Gly Lys Ala His Val Tyr Cys Glu Gly Asn
                100                 105                 110

Asp Val Tyr Asp Val Met Leu Asn Gln Thr Asn Leu Gln Phe Asn Asn
                115                 120                 125

Asn Lys Tyr Tyr Leu Ile Gln Leu Leu Glu Asp Ala Gln Arg Asn
    130                 135                 140

Phe Ser Val Trp Met Arg Trp Gly Arg Val Gly Lys Met Gly Gln His
145                 150                 155                 160

Ser Leu Val Ala Cys Ser Gly Asn Leu Asn Lys Ala Lys Glu Ile Phe
                165                 170                 175

Gln Lys Lys Phe Leu Asp Lys Thr Lys Asn Asn Trp Glu Asp Arg Glu
                180                 185                 190

Lys Phe Glu Lys Val Pro Gly Lys Tyr Asp Met Leu Gln Met Asp Tyr
                195                 200                 205

Ala Thr Asn Thr Gln Asp Glu Glu Thr Lys Lys Glu Glu Ser Leu
    210                 215                 220

Lys Ser Pro Leu Lys Pro Glu Ser Gln Leu Asp Leu Arg Val Gln Glu
225                 230                 235                 240

Leu Ile Lys Leu Ile Cys Asn Val Gln Ala Met Glu Glu Met Met Met
                245                 250                 255

Glu Met Lys Tyr Asn Thr Lys Lys Ala Pro Leu Gly Lys Leu Thr Val
                260                 265                 270

Ala Gln Ile Lys Ala Gly Tyr Gln Ser Leu Lys Lys Ile Glu Asp Cys
                275                 280                 285

Ile Arg Ala Gly Gln His Gly Arg Ala Leu Met Glu Ala Cys Asn Glu
    290                 295                 300

Phe Tyr Thr Arg Ile Pro His Asp Phe Gly Leu Arg Thr Pro Pro Leu
305                 310                 315                 320

Ile Arg Thr Gln Lys Glu Leu Ser Glu Lys Ile Gln Leu Leu Glu Ala
                325                 330                 335

Leu Gly Asp Ile Glu Ile Ala Ile Lys Leu Val Lys Thr Glu Leu Gln
                340                 345                 350

Ser Pro Glu His Pro Leu Asp Gln His Tyr Arg Asn Leu His Cys Ala
    355                 360                 365

Leu Arg Pro Leu Asp His Glu Ser Tyr Glu Phe Lys Val Ile Ser Gln
    370                 375                 380

Tyr Leu Gln Ser Thr His Ala Pro Thr His Ser Asp Tyr Thr Met Thr
385                 390                 395                 400

Leu Leu Asp Leu Phe Glu Val Glu Lys Asp Gly Glu Lys Glu Ala Phe
                405                 410                 415

Arg Glu Asp Leu His Asn Arg Met Leu Leu Trp His Gly Ser Arg Met
                420                 425                 430

Ser Asn Trp Val Gly Ile Leu Ser His Gly Leu Arg Ile Ala Pro Pro
    435                 440                 445

Glu Ala Pro Ile Thr Gly Tyr Met Phe Gly Lys Gly Ile Tyr Phe Ala
    450                 455                 460

Asp Met Ser Ser Lys Ser Ala Asn Tyr Cys Phe Ala Ser Arg Leu Lys
465                 470                 475                 480

Asn Thr Gly Leu Leu Leu Leu Ser Glu Val Ala Leu Gly Gln Cys Asn
                485                 490                 495

Glu Leu Leu Glu Ala Asn Pro Lys Ala Glu Gly Leu Leu Gln Gly Lys
```

-continued

```
              500                 505                 510
His Ser Thr Lys Gly Leu Gly Lys Met Ala Pro Ser Ser Ala His Phe
        515                 520                 525

Val Thr Leu Asn Gly Ser Thr Val Pro Leu Gly Pro Ala Ser Asp Thr
    530                 535                 540

Gly Ile Leu Asn Pro Asp Gly Tyr Thr Leu Asn Tyr Asn Glu Tyr Ile
545                 550                 555                 560

Val Tyr Asn Pro Asn Gln Val Arg Met Arg Tyr Leu Leu Lys Val Gln
                565                 570                 575

Phe Asn Phe Leu Gln Leu Trp
            580

<210> SEQ ID NO 3
<211> LENGTH: 472
<212> TYPE: DNA
<213> ORGANISM: Homo sapiens

<400> SEQUENCE: 3
tttttttttt tttttttag  acctgtacag ttttattac  ataaaatatc acaaaattca     60
caagtacaac actgcttatt ttcttgcttg aagatcagat ctctggttta tttaagatca    120
acattcacca cagctgaagg aaattaaact gaacctttaa aaggtaccgc atacggacct    180
ggttggggtt atatacaata tattcattgt agttgagggt ataaccatct ggattcagaa    240
ttcctgtgtc acttgctggt cctaatggca ctgtactccc attcctgcca aatggaaaaa    300
aagtgtgtca acatcagtct ctggttcaga agctgcaata gagaacgtag tcttatctgg    360
ccaaaaggag tcttctagtc ctcctggttc tgagtactta cagggtgacg aagtgggcag    420
aactgggagc catcttgccc agccccttgg ggctatgttt accttgaagc aa             472

<210> SEQ ID NO 4
<211> LENGTH: 476
<212> TYPE: DNA
<213> ORGANISM: Homo sapiens
<220> FEATURE:
<221> NAME/KEY: misc_feature
<222> LOCATION: (4)
<223> OTHER INFORMATION: n = A or T or G or C
<220> FEATURE:
<221> NAME/KEY: misc_feature
<222> LOCATION: (243)
<223> OTHER INFORMATION: n = A or T or G or C
<220> FEATURE:
<221> NAME/KEY: misc_feature
<222> LOCATION: (325)
<223> OTHER INFORMATION: n = A or T or G or C
<220> FEATURE:
<221> NAME/KEY: misc_feature
<222> LOCATION: (444)
<223> OTHER INFORMATION: n = A or T or G or C
<220> FEATURE:
<221> NAME/KEY: misc_feature
<222> LOCATION: (451)
<223> OTHER INFORMATION: n = A or T or G or C
<220> FEATURE:
<221> NAME/KEY: misc_feature
<222> LOCATION: (464)
<223> OTHER INFORMATION: n = A or T or G or C
<220> FEATURE:
<221> NAME/KEY: misc_feature
<222> LOCATION: (470)
<223> OTHER INFORMATION: n = A or T or G or C

<400> SEQUENCE: 4
aganctgtac agttttttatt acataaaata tcacaaaatt cacaagtaca cactgcttat     60
```

-continued

```
tttcttgctt gaagatcaga tctctggttt atttaatatc aacattcacc acagctgaag      120
gaaattaaac tgaaccttta aaaggtaccg catacggacc tgggttgggg ttatatacaa      180
tatattcatt gtagttgagg gtataacatc tgggattcag aattcctgtg tcacttgctg      240
ggncctaatg ggcactgtac tcccattcag gggtgacgag tgggggcagg aactggggag      300
gccatcttgc ccaggcccct tgggngctat ggtttacctt gaaggcaatc cttcgggcct      360
tagggattgg gcctctagta gttcattaca ctggacctag gggctacctc tggtaggggc      420
agcagtcccg tatttttag ggcnagaggg naaagcagtt attngggcan ttttgg          476
```

<210> SEQ ID NO 5
<211> LENGTH: 416
<212> TYPE: DNA
<213> ORGANISM: Homo sapiens
<220> FEATURE:
<221> NAME/KEY: misc_feature
<222> LOCATION: (334)
<223> OTHER INFORMATION: n = A or T or G or C
<220> FEATURE:
<221> NAME/KEY: misc_feature
<222> LOCATION: (346)
<223> OTHER INFORMATION: n = A or T or G or C
<220> FEATURE:
<221> NAME/KEY: misc_feature
<222> LOCATION: (360)
<223> OTHER INFORMATION: n = A or T or G or C
<220> FEATURE:
<221> NAME/KEY: misc_feature
<222> LOCATION: (381)
<223> OTHER INFORMATION: n = A or T or G or C
<220> FEATURE:
<221> NAME/KEY: misc_feature
<222> LOCATION: (387)
<223> OTHER INFORMATION: n = A or T or G or C

<400> SEQUENCE: 5

```
gctttgggag acattgaaat tgctattaag ctggtgaaaa cagagctaca aagcccagaa       60
cacccattgg accaacacta tagaaaccta cattgtgcct tgcgccccct tgaccatgaa      120
agttatgagt tcaaagtgat ttcccagtac ctacaatcta cccatgctcc cacacacagc      180
gactattacc atggaccttg ctgggatttg tttgaagtgg aggaaggga tgggtgagga       240 aaggaaggcc tttcaggagg agggacctttt cattaacagg gatgctttct atggggcatg     300
ggttccaggg gttgaggtaa ctggggttgg ggantctttg aggccntggg gttttcggan     360 tttgcccca ccttggaagg ntccccntca cagggtttac atgttttgg gggaaa          416
```

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 6

```
gtgttggtcc aatgggtgtt ctgggctttg tagctctg                              38
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7

```
ccatcctaat acgactcact atagggc                                          27
```

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
tgtaaaacga cggccagt                                                    18

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 9
ggaaacagct atgaccatg                                                   19

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:Primer

<400> SEQUENCE: 10
ggctgtacac tctgggtcca caggagc                                          27

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 11
cttccatgag agctcgtcca tgctggcc                                         28

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 12
ggccagcatg gacgagctct catggaag                                         28

<210> SEQ ID NO 13
<211> LENGTH: 1143
<212> TYPE: DNA
<213> ORGANISM: Homo sapiens

<400> SEQUENCE: 13
gcctagtgac actgggcccg cgattccttg gagcgggttg atgacgtcag cgttcgaatt       60
ccatggcggc gcggcggcga cggagcaccg gcggcggcag ggcgagagca ttaaatgaaa      120
gcaaaagagt taataatggc aacacggctc cagaagactc ttcccctgcc aagaaaactc      180
gtagatgcca gagacaggag tcgaaaaaga tgcctgtggc tggaggaaaa gctaataagg      240
acaggacaga agacaagcaa gatggtatgc caggaaggtc atgggccagc aaaagggtct      300

```
ctgaatctgt gaaggccttg ctgttaaagg gcaaagctcc tgtggaccca gagtgtacag      360
ccaaggtggg gaaggctcat gtgtattgtg aaggaaatga tgtctatgat gtcatgctaa      420
atcagaccaa tctccagttc aacaacaaca agtactatct gattcagcta ttagaagatg      480
atgcccagag gaacttcagt gtttggatga gatggggccg agttgggaaa atgggacagc      540
acagcctggt ggcttgttca ggcaatctca acaaggccaa ggaaatcttt cagaagaaat      600
tccttgacaa aacgaaaaac aattgggaag atcgagaaaa gtttgagaag gtgcctggaa      660
aatatgatat gctacagatg gactatgcca ccaatactca ggatgaagag gaaacaaaga      720
aagaggaatc tcttaaatct cccttgaagc cagagtcaca gctagatctt cgggtacagg      780
agttaataaa gttgatctgt aatgttcagg ccatggaaga aatgatgatg gaaatgaagt      840
ataataccaa gaaagcccca cttgggaagc tgacagtggc acaaatcaag gcaggttacc      900
agtctcttaa gaagattgag gattgtattc gggctggcca gcatggacga gctctcatgg      960
aagcatgcaa tgaattctac accaggattc cgcatgactt tggactccgt actcctccac     1020
taatccggac acagaaggaa ctgtcagaaa aaatacaatt actagaggct ttgggagaca     1080
ttgaaattgc tattaagctg gtgaaaacag agctacaaag cccagaacac ccattggacc     1140
aac                                                                   1143

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
gctcctgtgg acccagagtg tacagcc                                          27

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
acattcacca cagctgaagg                                                  20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
ccacagctga aggaaattaa ac                                               22

<210> SEQ ID NO 17
<211> LENGTH: 550
<212> TYPE: DNA
<213> ORGANISM: Artificial Sequence
<220> FEATURE:
<223> OTHER INFORMATION: Description of Artificial Sequence:P2-1 (hPARP2
      Fragment)

<400> SEQUENCE: 17
agccaaggtg gggaaggctc atgtgtattg tgaaggaaat gatgtctatg atgtcatgct      60
```

-continued

```
aaatcagacc aatctccagt tcaacaacaa caagtactat ctgattcagc tattagaaga      120
tgatgcccag aggaacttca gtgtttggat gagatggggc cgagttggga aaatgggaca      180
gcacagcctg gtggcttgtt caggcaatct caacaaggcc aaggaaatct ttcagaagaa      240
attccttgac aaaacgaaaa acaattggga agatcgagaa aagtttgaga aggtgcctgg      300
aaaatatgat atgctacaga tggactatgc caccaatact caggatgaag aggaaacaaa      360
gaaagaggaa tctcttaaat ctcccttgaa gccagagtca cagctagatc ttcgggtaca      420
ggagttaata aagttgatct gtaatgttca ggccatggaa gaaatgatga tggaaatgaa      480
gtataatacc aagaaagccc cacttgggaa gctgacagtg gcacaaatca aggcaggtta      540
ccagtctctt                                                             550
```

<210> SEQ ID NO 18
<211> LENGTH: 550
<212> TYPE: DNA
<213> ORGANISM: Artificial Sequence
<220> FEATURE:
<223> OTHER INFORMATION: Description of Artificial Sequence:P2-9 (hPARP2 Fragment)

<400> SEQUENCE: 18

```
agccaaggtg gggaaggctc atgtgtattg tgaaggaaat gatgtctatg atgtcatgct       60
aaatcagacc aatctccagt tcaacaacaa caagtactat ctgattcagc tattagaaga      120
tgatgcccag aggaacttca gtgtttggat gagatggggc cgagttggga aaatgggaca      180
gcacagcctg gtggcttgtt caggcaatct caacaaggcc aaggaaatct ttcagaagaa      240
attccttgac aaaacgaaaa acaattggga agatcgagaa aagtttgaga aggtgcctgg      300
aaaatatgat atgctacaga tggactatgc caccaatact caggatgaag aggaaacaaa      360
gaaagaggaa tctcttaaat ctcccttgaa gccagagtca cagctagatc ttcgggtaca      420
ggagttaata aagttgatct gtaatgttca ggccatggaa gaaatgatga tggaaatgaa      480
gtataatacc aagaaagccc cacttgggaa gctgacagtg gcacaaatca aggcaggtta      540
ccagtctctt                                                             550
```

<210> SEQ ID NO 19
<211> LENGTH: 360
<212> TYPE: PRT
<213> ORGANISM: Homo sapiens

<400> SEQUENCE: 19

```
Met Ala Ala Arg Arg Arg Arg Ser Thr Gly Gly Gly Arg Ala Arg Ala
 1               5                  10                  15

Leu Asn Glu Ser Lys Arg Val Asn Asn Gly Asn Thr Ala Pro Glu Asp
                20                  25                  30

Ser Ser Pro Ala Lys Lys Thr Arg Arg Cys Gln Arg Gln Glu Ser Lys
            35                  40                  45

Lys Met Pro Val Ala Gly Gly Lys Ala Asn Lys Asp Arg Thr Glu Asp
        50                  55                  60

Lys Gln Asp Gly Met Pro Gly Arg Ser Trp Ala Ser Lys Arg Val Ser
 65                 70                  75                  80

Glu Ser Val Lys Ala Leu Leu Leu Lys Gly Lys Ala Pro Val Asp Pro
                85                  90                  95

Glu Cys Thr Ala Lys Val Gly Lys Ala His Val Tyr Cys Glu Gly Asn
                100                 105                 110

Asp Val Tyr Asp Val Met Leu Asn Gln Thr Asn Leu Gln Phe Asn Asn
```

```
            115                 120                 125
Asn Lys Tyr Tyr Leu Ile Gln Leu Leu Glu Asp Asp Ala Gln Arg Asn
    130                 135                 140

Phe Ser Val Trp Met Arg Trp Gly Arg Val Gly Lys Met Gly Gln His
145                 150                 155                 160

Ser Leu Val Ala Cys Ser Gly Asn Leu Asn Lys Ala Lys Glu Ile Phe
                165                 170                 175

Gln Lys Lys Phe Leu Asp Lys Thr Lys Asn Asn Trp Glu Asp Arg Glu
            180                 185                 190

Lys Phe Glu Lys Val Pro Gly Lys Tyr Asp Met Leu Gln Met Asp Tyr
        195                 200                 205

Ala Thr Asn Thr Gln Asp Glu Glu Thr Lys Lys Glu Glu Ser Leu
    210                 215                 220

Lys Ser Pro Leu Lys Pro Glu Ser Gln Leu Asp Leu Arg Val Gln Glu
225                 230                 235                 240

Leu Ile Lys Leu Ile Cys Asn Val Gln Ala Met Glu Glu Met Met Met
                245                 250                 255

Glu Met Lys Tyr Asn Thr Lys Lys Ala Pro Leu Gly Lys Leu Thr Val
            260                 265                 270

Ala Gln Ile Lys Ala Gly Tyr Gln Ser Leu Lys Lys Ile Glu Asp Cys
        275                 280                 285

Ile Arg Ala Gly Gln His Gly Arg Ala Leu Met Glu Ala Cys Asn Glu
    290                 295                 300

Phe Tyr Thr Arg Ile Pro His Asp Phe Gly Leu Arg Thr Pro Pro Leu
305                 310                 315                 320

Ile Arg Thr Gln Lys Glu Leu Ser Glu Lys Ile Gln Leu Leu Glu Ala
                325                 330                 335

Leu Gly Asp Ile Glu Ile Ala Ile Lys Leu Val Lys Thr Glu Leu Gln
            340                 345                 350

Ser Pro Glu His Pro Leu Asp Gln
        355                 360

<210> SEQ ID NO 20
<211> LENGTH: 864
<212> TYPE: DNA
<213> ORGANISM: Homo sapiens

<400> SEQUENCE: 20
gctctcatgg aagcatgcaa tgaattctac accaggattc cgcatgactt tggactccgt      60
actcctccac taatccggac acagaaggaa ctgtcagaaa aaatacaatt actagaggct     120
ttgggagaca ttgaaattgc tattaagctg gtgaaaacag agctacaaag cccagaacac     180
ccattggacc aacactatag aaacctacat tgtgccttgc gccccttga ccatgaaagt      240 tacgagttca aagtgatttc ccagtaccta caatctaccc atgctcccac acacagcgac     300
tataccatga ccttgctgga tttgtttgaa gtggagaagg atggtgagaa gaagccttc      360 agagaggacc ttcataacag gatgcttcta tggcatggtt ccaggatgag taactgggtg     420
ggaatcttga gccatgggct tcgaattgcc ccacctgaag ctcccatcac aggttacatg     480
tttgggaaag gaatctactt tgctgacatg tcttccaaga gtgccaatta ctgctttgcc     540
tctcgcctaa agaatacagg actgctgctc ttatcagagg tagctctagg tcagtgtaat     600
gaactactag aggccaatcc taaggccgaa ggattgcttc aaggtaaaca tagcaccaag     660
gggctgggca agatggctcc cagttctgcc cacttcgtca ccctgaatgg gagtacagtg     720
```

```
ccattaggac cagcaagtga cacaggaatt ctgaatccag atggttatac cctcaactac    780
aatgaatata ttgtatataa ccccaaccag gtccgtatgc ggtaccttt aaaggttcag    840 tttaatttcc ttcagctgtg gtga                                          864
```

<210> SEQ ID NO 21
<211> LENGTH: 287
<212> TYPE: PRT
<213> ORGANISM: Homo sapiens

<400> SEQUENCE: 21

```
Ala Leu Met Glu Ala Cys Asn Glu Phe Tyr Thr Arg Ile Pro His Asp
 1               5                  10                  15

Phe Gly Leu Arg Thr Pro Pro Leu Ile Arg Thr Gln Lys Glu Leu Ser
            20                  25                  30

Glu Lys Ile Gln Leu Leu Glu Ala Leu Gly Asp Ile Glu Ile Ala Ile
        35                  40                  45

Lys Leu Val Lys Thr Glu Leu Gln Ser Pro Glu His Pro Leu Asp Gln
    50                  55                  60

His Tyr Arg Asn Leu His Cys Ala Leu Arg Pro Leu Asp His Glu Ser
65                  70                  75                  80

Tyr Glu Phe Lys Val Ile Ser Gln Tyr Leu Gln Ser Thr His Ala Pro
                85                  90                  95

Thr His Ser Asp Tyr Thr Met Thr Leu Leu Asp Leu Phe Glu Val Glu
            100                 105                 110

Lys Asp Gly Glu Lys Glu Ala Phe Arg Glu Asp Leu His Asn Arg Met
        115                 120                 125

Leu Leu Trp His Gly Ser Arg Met Ser Asn Trp Val Gly Ile Leu Ser
    130                 135                 140

His Gly Leu Arg Ile Ala Pro Pro Glu Ala Pro Ile Thr Gly Tyr Met
145                 150                 155                 160

Phe Gly Lys Gly Ile Tyr Phe Ala Asp Met Ser Ser Lys Ser Ala Asn
                165                 170                 175

Tyr Cys Phe Ala Ser Arg Leu Lys Asn Thr Gly Leu Leu Leu Leu Ser
            180                 185                 190

Glu Val Ala Leu Gly Gln Cys Asn Glu Leu Leu Glu Ala Asn Pro Lys
        195                 200                 205

Ala Glu Gly Leu Leu Gln Gly Lys His Ser Thr Lys Gly Leu Gly Lys
    210                 215                 220

Met Ala Pro Ser Ser Ala His Phe Val Thr Leu Asn Gly Ser Thr Val
225                 230                 235                 240

Pro Leu Gly Pro Ala Ser Asp Thr Gly Ile Leu Asn Pro Asp Gly Tyr
                245                 250                 255

Thr Leu Asn Tyr Asn Glu Tyr Ile Val Tyr Asn Pro Asn Gln Val Arg
            260                 265                 270

Met Arg Tyr Leu Leu Lys Val Gln Phe Asn Phe Leu Gln Leu Trp
        275                 280                 285
```

<210> SEQ ID NO 22
<211> LENGTH: 1707
<212> TYPE: DNA
<213> ORGANISM: Mus musculus
<220> FEATURE:
<221> NAME/KEY: CDS
<222> LOCATION: (16)..(1695)
<223> OTHER INFORMATION:

<400> SEQUENCE: 22

-continued

| | |
|---|---|
| ctcgagtcaa gagcg atg gcg ccg cgg cgg cag aga tca ggc tct gga agg<br>                 Met Ala Pro Arg Arg Gln Arg Ser Gly Ser Gly Arg<br>                  1                 5                 10 | 51 |
| cga gtg cta aat gaa gcc aag aaa gtt gat aat ggc aac aaa gca aca<br>Arg Val Leu Asn Glu Ala Lys Lys Val Asp Asn Gly Asn Lys Ala Thr<br>             15                     20                  25 | 99 |
| gaa gac gac tct cct cct ggc aag aag atg cgc acg tgc cag aga aaa<br>Glu Asp Asp Ser Pro Pro Gly Lys Lys Met Arg Thr Cys Gln Arg Lys<br>    30                     35                  40 | 147 |
| ggg cct atg gct gga ggg aag gac gca gac agg aca aaa gac aat cga<br>Gly Pro Met Ala Gly Gly Lys Asp Ala Asp Arg Thr Lys Asp Asn Arg<br> 45                 50                  55               60 | 195 |
| gac tct gtg aag acc ttg ctg tta aag ggc aaa gcc cct gtg gac cca<br>Asp Ser Val Lys Thr Leu Leu Leu Lys Gly Lys Ala Pro Val Asp Pro<br>             65                     70                  75 | 243 |
| gag tgt gca gcc aag ctg gga aag gct cat gtg tat tgt gaa gga gat<br>Glu Cys Ala Ala Lys Leu Gly Lys Ala His Val Tyr Cys Glu Gly Asp<br>           80                     85                  90 | 291 |
| gat gtc tat gat gtc atg cta aat caa acc aat ctc cag ttc aac aac<br>Asp Val Tyr Asp Val Met Leu Asn Gln Thr Asn Leu Gln Phe Asn Asn<br>             95                   100              105 | 339 |
| aac aag tac tac ctt att cag ctg tta gaa gat gat gcc cag agg aac<br>Asn Lys Tyr Tyr Leu Ile Gln Leu Leu Glu Asp Asp Ala Gln Arg Asn<br> 110                 115                 120 | 387 |
| ttc agt gtt tgg atg agg tgg ggc cga gtt gga aag acg ggc cag cac<br>Phe Ser Val Trp Met Arg Trp Gly Arg Val Gly Lys Thr Gly Gln His<br>125                 130                 135              140 | 435 |
| agc ttg gtg act tgt tct ggt gac ctc aac aaa gca aaa gaa ata ttt<br>Ser Leu Val Thr Cys Ser Gly Asp Leu Asn Lys Ala Lys Glu Ile Phe<br>                145                 150              155 | 483 |
| cag aaa aaa ttc ctt gac aaa act aaa aac aat tgg gag gac cgt gag<br>Gln Lys Lys Phe Leu Asp Lys Thr Lys Asn Asn Trp Glu Asp Arg Glu<br>         160                 165                 170 | 531 |
| aac ttt gaa aaa gta cct gga aaa tac gac atg tta cag atg gac tat<br>Asn Phe Glu Lys Val Pro Gly Lys Tyr Asp Met Leu Gln Met Asp Tyr<br>              175                 180              185 | 579 |
| gct gcc agc acg cag gat gaa agt aaa aca aaa gaa gag gaa act ttg<br>Ala Ala Ser Thr Gln Asp Glu Ser Lys Thr Lys Glu Glu Glu Thr Leu<br> 190                 195                 200 | 627 |
| aag cct gag tct cag ctg gat ctt cga gtc cag gag ctg cta aag ttg<br>Lys Pro Glu Ser Gln Leu Asp Leu Arg Val Gln Glu Leu Leu Lys Leu<br>205                 210                 215              220 | 675 |
| atc tgt aac gtg cag acc atg gaa gaa atg atg att gag atg aag tat<br>Ile Cys Asn Val Gln Thr Met Glu Glu Met Met Ile Glu Met Lys Tyr<br>                225                 230              235 | 723 |
| gac acc aag aga gcc ccg ctt gga aag ctg aca gtg gcg caa atc aag<br>Asp Thr Lys Arg Ala Pro Leu Gly Lys Leu Thr Val Ala Gln Ile Lys<br>         240                 245                 250 | 771 |
| gcc ggt tac cag tct ctc aag aag att gag gac tgc atc cgc gct ggc<br>Ala Gly Tyr Gln Ser Leu Lys Lys Ile Glu Asp Cys Ile Arg Ala Gly<br>              255                 260              265 | 819 |
| cag cat ggg cga gcg ctt gtt gaa gcg tgc aat gaa ttc tac acc agg<br>Gln His Gly Arg Ala Leu Val Glu Ala Cys Asn Glu Phe Tyr Thr Arg<br> 270                 275                 280 | 867 |
| atc cct cat gac ttt gga ctc tcc atc cct cca gta atc cgg aca gag<br>Ile Pro His Asp Phe Gly Leu Ser Ile Pro Pro Val Ile Arg Thr Glu<br>285                 290                 295              300 | 915 |
| aag gaa ctg tca gac aaa gta aaa ctg cta gag gca ttg gga gac att<br>Lys Glu Leu Ser Asp Lys Val Lys Leu Leu Glu Ala Leu Gly Asp Ile | 963 |

| | | | | |
|---|---|---|---|---|
| gaa att gcc ctt aaa ctg gtg aag tca gag cgc caa ggc cta gaa cac<br>Glu Ile Ala Leu Lys Leu Val Lys Ser Glu Arg Gln Gly Leu Glu His<br>320 325 330 | | | | 1011 |
| cca ctg gac caa cac tat aga aac cta cac tgt gct ttg cgt cct ctg<br>Pro Leu Asp Gln His Tyr Arg Asn Leu His Cys Ala Leu Arg Pro Leu<br>335 340 345 | | | | 1059 |
| gac cat gaa agt aat gag ttt aag gtg att tct cag tac cta cag tct<br>Asp His Glu Ser Asn Glu Phe Lys Val Ile Ser Gln Tyr Leu Gln Ser<br>350 355 360 | | | | 1107 |
| acg cat gct cct aca cac aag gac tat act atg acc ttg ctg gat gtt<br>Thr His Ala Pro Thr His Lys Asp Tyr Thr Met Thr Leu Leu Asp Val<br>365 370 375 380 | | | | 1155 |
| ttc gaa gta gag aag gaa ggg gag aaa gag gcc ttc agg gag gac ctt<br>Phe Glu Val Glu Lys Glu Gly Glu Lys Glu Ala Phe Arg Glu Asp Leu<br>385 390 395 | | | | 1203 |
| cct aac agg atg ctc ctc tgg cat gga tcc agg ctg agt aac tgg gtg<br>Pro Asn Arg Met Leu Leu Trp His Gly Ser Arg Leu Ser Asn Trp Val<br>400 405 410 | | | | 1251 |
| ggg atc ctg agc cac ggg ctt aga gtt gcc cca cct gag gct ccc atc<br>Gly Ile Leu Ser His Gly Leu Arg Val Ala Pro Pro Glu Ala Pro Ile<br>415 420 425 | | | | 1299 |
| aca ggt tat atg ttt gga aaa gga atc tac ttt gct gac atg tcc tcc<br>Thr Gly Tyr Met Phe Gly Lys Gly Ile Tyr Phe Ala Asp Met Ser Ser<br>430 435 440 | | | | 1347 |
| aag agt gcc aat tac tgc ttt gcc tct cgc cta aag aat aca gga ttg<br>Lys Ser Ala Asn Tyr Cys Phe Ala Ser Arg Leu Lys Asn Thr Gly Leu<br>445 450 455 460 | | | | 1395 |
| ctt ctt ctg tca gag gta gct cta ggt cag tgt aat gaa cta ctg gag<br>Leu Leu Leu Ser Glu Val Ala Leu Gly Gln Cys Asn Glu Leu Leu Glu<br>465 470 475 | | | | 1443 |
| gcc aat cct aaa gca caa gga ttg ctt cgg ggc aag cat agc acc aag<br>Ala Asn Pro Lys Ala Gln Gly Leu Leu Arg Gly Lys His Ser Thr Lys<br>480 485 490 | | | | 1491 |
| ggg atg gga aag atg gct ccc agc cct gcc cac ttc atc acc ctg aat<br>Gly Met Gly Lys Met Ala Pro Ser Pro Ala His Phe Ile Thr Leu Asn<br>495 500 505 | | | | 1539 |
| ggg agt aca gtg ccc tta gga cca gca agt gac aca gga att ctc aat<br>Gly Ser Thr Val Pro Leu Gly Pro Ala Ser Asp Thr Gly Ile Leu Asn<br>510 515 520 | | | | 1587 |
| cca gag ggg tac acc ctc aac tac aat gag ttt att gtt tat agc ccc<br>Pro Glu Gly Tyr Thr Leu Asn Tyr Asn Glu Phe Ile Val Tyr Ser Pro<br>525 530 535 540 | | | | 1635 |
| aac cag gtc cgt atg cga tac ctt cta aag att caa ttt aac ttc ctg<br>Asn Gln Val Arg Met Arg Tyr Leu Leu Lys Ile Gln Phe Asn Phe Leu<br>545 550 555 | | | | 1683 |
| cag cta tgg tga atgttgctcg ag<br>Gln Leu Trp | | | | 1707 |

<210> SEQ ID NO 23
<211> LENGTH: 559
<212> TYPE: PRT
<213> ORGANISM: Mus musculus

<400> SEQUENCE: 23

Met Ala Pro Arg Arg Gln Arg Ser Gly Ser Gly Arg Arg Val Leu Asn
1               5                   10                  15

Glu Ala Lys Lys Val Asp Asn Gly Asn Lys Ala Thr Glu Asp Asp Ser
            20                  25                  30

-continued

```
Pro Pro Gly Lys Lys Met Arg Thr Cys Gln Arg Lys Gly Pro Met Ala
         35                  40                  45

Gly Gly Lys Asp Ala Asp Arg Thr Lys Asp Asn Arg Asp Ser Val Lys
     50                  55                  60

Thr Leu Leu Leu Lys Gly Lys Ala Pro Val Asp Pro Glu Cys Ala Ala
 65                  70                  75                  80

Lys Leu Gly Lys Ala His Val Tyr Cys Glu Gly Asp Asp Val Tyr Asp
                 85                  90                  95

Val Met Leu Asn Gln Thr Asn Leu Gln Phe Asn Asn Asn Lys Tyr Tyr
            100                 105                 110

Leu Ile Gln Leu Leu Glu Asp Ala Gln Arg Asn Phe Ser Val Trp
            115                 120                 125

Met Arg Trp Gly Arg Val Gly Lys Thr Gly Gln His Ser Leu Val Thr
        130                 135                 140

Cys Ser Gly Asp Leu Asn Lys Ala Lys Glu Ile Phe Gln Lys Lys Phe
145                 150                 155                 160

Leu Asp Lys Thr Lys Asn Asn Trp Glu Asp Arg Glu Asn Phe Glu Lys
                165                 170                 175

Val Pro Gly Lys Tyr Asp Met Leu Gln Met Asp Tyr Ala Ala Ser Thr
                180                 185                 190

Gln Asp Glu Ser Lys Thr Lys Glu Glu Thr Leu Lys Pro Glu Ser
        195                 200                 205

Gln Leu Asp Leu Arg Val Gln Glu Leu Leu Lys Leu Ile Cys Asn Val
        210                 215                 220

Gln Thr Met Glu Glu Met Met Ile Glu Met Lys Tyr Asp Thr Lys Arg
225                 230                 235                 240

Ala Pro Leu Gly Lys Leu Thr Val Ala Gln Ile Lys Ala Gly Tyr Gln
                245                 250                 255

Ser Leu Lys Lys Ile Glu Asp Cys Ile Arg Ala Gly Gln His Gly Arg
                260                 265                 270

Ala Leu Val Glu Ala Cys Asn Glu Phe Tyr Thr Arg Ile Pro His Asp
                275                 280                 285

Phe Gly Leu Ser Ile Pro Pro Val Ile Arg Thr Glu Lys Glu Leu Ser
        290                 295                 300

Asp Lys Val Lys Leu Leu Glu Ala Leu Gly Asp Ile Glu Ile Ala Leu
305                 310                 315                 320

Lys Leu Val Lys Ser Glu Arg Gln Gly Leu Glu His Pro Leu Asp Gln
                325                 330                 335

His Tyr Arg Asn Leu His Cys Ala Leu Arg Pro Leu Asp His Glu Ser
                340                 345                 350

Asn Glu Phe Lys Val Ile Ser Gln Tyr Leu Gln Ser Thr His Ala Pro
        355                 360                 365

Thr His Lys Asp Tyr Thr Met Thr Leu Leu Asp Val Phe Glu Val Glu
        370                 375                 380

Lys Glu Gly Glu Lys Glu Ala Phe Arg Glu Asp Leu Pro Asn Arg Met
385                 390                 395                 400

Leu Leu Trp His Gly Ser Arg Leu Ser Asn Trp Val Gly Ile Leu Ser
                405                 410                 415

His Gly Leu Arg Val Ala Pro Pro Glu Ala Pro Ile Thr Gly Tyr Met
                420                 425                 430

Phe Gly Lys Gly Ile Tyr Phe Ala Asp Met Ser Ser Lys Ser Ala Asn
        435                 440                 445

Tyr Cys Phe Ala Ser Arg Leu Lys Asn Thr Gly Leu Leu Leu Leu Ser
```

```
                    450                 455                 460
Glu Val Ala Leu Gly Gln Cys Asn Glu Leu Leu Glu Ala Asn Pro Lys
465                 470                 475                 480

Ala Gln Gly Leu Leu Arg Gly Lys His Ser Thr Lys Gly Met Gly Lys
                485                 490                 495

Met Ala Pro Ser Pro Ala His Phe Ile Thr Leu Asn Gly Ser Thr Val
                500                 505                 510

Pro Leu Gly Pro Ala Ser Asp Thr Gly Ile Leu Asn Pro Glu Gly Tyr
                515                 520                 525

Thr Leu Asn Tyr Asn Glu Phe Ile Val Tyr Ser Pro Asn Gln Val Arg
                530                 535                 540

Met Arg Tyr Leu Leu Lys Ile Gln Phe Asn Phe Leu Gln Leu Trp
545                 550                 555

<210> SEQ ID NO 24
<211> LENGTH: 3045
<212> TYPE: DNA
<213> ORGANISM: Homo sapiens
<220> FEATURE:
<221> NAME/KEY: CDS
<222> LOCATION: (1)..(3045)
<223> OTHER INFORMATION:

<400> SEQUENCE: 24 atg gcg gag tct tcg gat aag ctc tat cga gtc gag tac gcc aag agc      48
Met Ala Glu Ser Ser Asp Lys Leu Tyr Arg Val Glu Tyr Ala Lys Ser
 1               5                  10                  15 ggg cgc gcc tct tgc aag aaa tgc agc gag agc atc ccc aag gac tcg      96
Gly Arg Ala Ser Cys Lys Lys Cys Ser Glu Ser Ile Pro Lys Asp Ser
                20                  25                  30 ctc cgg atg gcc atc atg gtg cag tcg ccc atg ttt gat gga aaa gtc     144
Leu Arg Met Ala Ile Met Val Gln Ser Pro Met Phe Asp Gly Lys Val
            35                  40                  45 cca cac tgg tac cac ttc tcc tgc ttc tgg aag gtg ggc cac tcc atc     192
Pro His Trp Tyr His Phe Ser Cys Phe Trp Lys Val Gly His Ser Ile
 50                  55                  60 cgg cac cct gac gtt gag gtg gat ggg ttc tct gag ctt cgg tgg gat     240
Arg His Pro Asp Val Glu Val Asp Gly Phe Ser Glu Leu Arg Trp Asp
 65                  70                  75                  80 gac cag cag aaa gtc aag aag aca gcg gaa gct gga gga gtg aca ggc     288
Asp Gln Gln Lys Val Lys Lys Thr Ala Glu Ala Gly Gly Val Thr Gly
                85                  90                  95 aaa ggc cag gat gga att ggt agc aag gca gag aag act ctg ggt gac     336
Lys Gly Gln Asp Gly Ile Gly Ser Lys Ala Glu Lys Thr Leu Gly Asp
            100                 105                 110 ttt gca gca gag tat gcc aag tcc aac aga agt acg tgc aag ggg tgt     384
Phe Ala Ala Glu Tyr Ala Lys Ser Asn Arg Ser Thr Cys Lys Gly Cys
        115                 120                 125 atg gag aag ata gaa aag ggc cag gtg cgc ctg tcc aag aag atg gtg     432
Met Glu Lys Ile Glu Lys Gly Gln Val Arg Leu Ser Lys Lys Met Val
    130                 135                 140 gac ccg gag aag cca cag cta ggc atg att gac cgc tgg tac cat cca     480
Asp Pro Glu Lys Pro Gln Leu Gly Met Ile Asp Arg Trp Tyr His Pro
145                 150                 155                 160 ggc tgc ttt gtc aag aac agg gag gag ctg ggt ttc cgg ccc gag tac     528
Gly Cys Phe Val Lys Asn Arg Glu Glu Leu Gly Phe Arg Pro Glu Tyr
                165                 170                 175 agt gcg agt cag ctc aag ggc ttc agc ctc ctt gct aca gag gat aaa     576
Ser Ala Ser Gln Leu Lys Gly Phe Ser Leu Leu Ala Thr Glu Asp Lys
            180                 185                 190
```

```
gaa gcc ctg aag aag cag ctc cca gga gtc aag agt gaa gga aag aga      624
Glu Ala Leu Lys Lys Gln Leu Pro Gly Val Lys Ser Glu Gly Lys Arg
            195                 200                 205 aaa ggc gat gag gtg gat gga gtg gat gaa gtg gcg aag aag aaa tct      672
Lys Gly Asp Glu Val Asp Gly Val Asp Glu Val Ala Lys Lys Lys Ser
210                 215                 220 aaa aaa gaa aaa gac aag gat agt aag ctt gaa aaa gcc cta aag gct      720
Lys Lys Glu Lys Asp Lys Asp Ser Lys Leu Glu Lys Ala Leu Lys Ala
225                 230                 235                 240 cag aac gac ctg atc tgg aac atc aag gac gag cta aag aaa gtg tgt      768
Gln Asn Asp Leu Ile Trp Asn Ile Lys Asp Glu Leu Lys Lys Val Cys
            245                 250                 255 tca act aat gac ctg aag gag cta ctc atc ttc aac aag cag caa gtg      816
Ser Thr Asn Asp Leu Lys Glu Leu Leu Ile Phe Asn Lys Gln Gln Val
            260                 265                 270 cct tct ggg gag tcg gcg atc ttg gac cga gta gct gat ggc atg gtg      864
Pro Ser Gly Glu Ser Ala Ile Leu Asp Arg Val Ala Asp Gly Met Val
            275                 280                 285 ttc ggt gcc ctc ctt ccc tgc gag gaa tgc tcg ggt cag ctg gtc ttc      912
Phe Gly Ala Leu Leu Pro Cys Glu Glu Cys Ser Gly Gln Leu Val Phe
290                 295                 300 aag agc gat gcc tat tac tgc act ggg gac gtc act gcc tgg acc aag      960
Lys Ser Asp Ala Tyr Tyr Cys Thr Gly Asp Val Thr Ala Trp Thr Lys
305                 310                 315                 320 tgt atg gtc aag aca cag aca ccc aac cgg aag gag tgg gta acc cca     1008
Cys Met Val Lys Thr Gln Thr Pro Asn Arg Lys Glu Trp Val Thr Pro
            325                 330                 335 aag gaa ttc cga gaa atc tct tac ctc aag aaa ttg aag gtt aaa aag     1056
Lys Glu Phe Arg Glu Ile Ser Tyr Leu Lys Lys Leu Lys Val Lys Lys
            340                 345                 350 cag gac cgt ata ttc ccc cca gaa acc agc gcc tcc gtg gcg gcc acg     1104
Gln Asp Arg Ile Phe Pro Pro Glu Thr Ser Ala Ser Val Ala Ala Thr
            355                 360                 365 cct ccg ccc tcc aca gcc tcg gct cct gct gct gtg aac tcc tct gct     1152
Pro Pro Pro Ser Thr Ala Ser Ala Pro Ala Ala Val Asn Ser Ser Ala
            370                 375                 380 tca gca gat aag cca tta tcc aac atg aag atc ctg act ctc ggg aag     1200
Ser Ala Asp Lys Pro Leu Ser Asn Met Lys Ile Leu Thr Leu Gly Lys
385                 390                 395                 400 ctg tcc cgg aac aag gat gaa gtg aag gcc atg att gag aaa ctc ggg     1248
Leu Ser Arg Asn Lys Asp Glu Val Lys Ala Met Ile Glu Lys Leu Gly
                405                 410                 415 ggg aag ttg acg ggg acg gcc aac aag gct tcc ctg tgc atc agc acc     1296
Gly Lys Leu Thr Gly Thr Ala Asn Lys Ala Ser Leu Cys Ile Ser Thr
            420                 425                 430 aaa aag gag gtg gaa aag atg aat aag aag atg gag gaa gta aag gaa     1344
Lys Lys Glu Val Glu Lys Met Asn Lys Lys Met Glu Glu Val Lys Glu
            435                 440                 445 gcc aac atc cga gtt gtg tct gag gac ttc ctc cag gac gtc tcc gcc     1392
Ala Asn Ile Arg Val Val Ser Glu Asp Phe Leu Gln Asp Val Ser Ala
450                 455                 460 tcc acc aag agc ctt cag gag ttg ttc tta gcg cac atc ttg tcc cct     1440
Ser Thr Lys Ser Leu Gln Glu Leu Phe Leu Ala His Ile Leu Ser Pro
465                 470                 475                 480 tgg ggg gca gag gtg aag gca gag cct gtt gaa gtt gtg gcc cca aga     1488
Trp Gly Ala Glu Val Lys Ala Glu Pro Val Glu Val Val Ala Pro Arg
                485                 490                 495 ggg aag tca ggg gct gcg ctc tcc aaa aaa agc aag ggc cag gtc aag     1536
Gly Lys Ser Gly Ala Ala Leu Ser Lys Lys Ser Lys Gly Gln Val Lys
```

-continued

```
                    500                 505                 510
gag gaa ggt atc aac aaa tct gaa aag aga atg aaa tta act ctt aaa        1584
Glu Glu Gly Ile Asn Lys Ser Glu Lys Arg Met Lys Leu Thr Leu Lys
            515                 520                 525 gga gga gca gct gtg gat cct gat tct gga ctg gaa cac tct gcg cat        1632
Gly Gly Ala Ala Val Asp Pro Asp Ser Gly Leu Glu His Ser Ala His
530                 535                 540 gtc ctg gag aaa ggt ggg aag gtc ttc agt gcc acc ctt ggc ctg gtg        1680
Val Leu Glu Lys Gly Gly Lys Val Phe Ser Ala Thr Leu Gly Leu Val
545                 550                 555                 560 gac atc gtt aaa gga acc aac tcc tac tac aag ctg cag ctt ctg gag        1728
Asp Ile Val Lys Gly Thr Asn Ser Tyr Tyr Lys Leu Gln Leu Leu Glu
            565                 570                 575 gac gac aag gaa aac agg tat tgg ata ttc agg tcc tgg ggc cgt gtg        1776
Asp Asp Lys Glu Asn Arg Tyr Trp Ile Phe Arg Ser Trp Gly Arg Val
            580                 585                 590 ggt acg gtg atc ggt agc aac aaa ctg gaa cag atg ccg tcc aag gag        1824
Gly Thr Val Ile Gly Ser Asn Lys Leu Glu Gln Met Pro Ser Lys Glu
            595                 600                 605 gat gcc att gag cag ttc atg aaa tta tat gaa gaa aaa acc ggg aac        1872
Asp Ala Ile Glu Gln Phe Met Lys Leu Tyr Glu Glu Lys Thr Gly Asn
            610                 615                 620 gct tgg cac tcc aaa aat ttc acg aag tat ccc aaa aag ttt tac ccc        1920
Ala Trp His Ser Lys Asn Phe Thr Lys Tyr Pro Lys Lys Phe Tyr Pro
625                 630                 635                 640 ctg gag att gac tat ggc cag gat gaa gag gca gtg aag aag ctc aca        1968
Leu Glu Ile Asp Tyr Gly Gln Asp Glu Glu Ala Val Lys Lys Leu Thr
                    645                 650                 655 gta aat cct ggc acc aag tcc aag ctc ccc aag cca gtt cag gac ctc        2016
Val Asn Pro Gly Thr Lys Ser Lys Leu Pro Lys Pro Val Gln Asp Leu
            660                 665                 670 atc aag atg atc ttt gat gtg gaa agt atg aag aaa gcc atg gtg gag        2064
Ile Lys Met Ile Phe Asp Val Glu Ser Met Lys Lys Ala Met Val Glu
            675                 680                 685 tat gag atc gac ctt cag aag atg ccc ttg ggg aag ctg agc aaa agg        2112
Tyr Glu Ile Asp Leu Gln Lys Met Pro Leu Gly Lys Leu Ser Lys Arg
            690                 695                 700 cag atc cag gcc gca tac tcc atc ctc agt gag gtc cag cag gcg gtg        2160
Gln Ile Gln Ala Ala Tyr Ser Ile Leu Ser Glu Val Gln Gln Ala Val
705                 710                 715                 720 tct cag ggc agc agc gac tct cag atc ctg gat ctc tca aat cgc ttt        2208
Ser Gln Gly Ser Ser Asp Ser Gln Ile Leu Asp Leu Ser Asn Arg Phe
                    725                 730                 735 tac acc ctg atc ccc cac gac ttt ggg atg aag aag cct ccg ctc ctg        2256
Tyr Thr Leu Ile Pro His Asp Phe Gly Met Lys Lys Pro Pro Leu Leu
                    740                 745                 750 aac aat gca gac agt gtg cag gcc aag gtg gaa atg ctt gac aac ctg        2304
Asn Asn Ala Asp Ser Val Gln Ala Lys Val Glu Met Leu Asp Asn Leu
            755                 760                 765 ctg gac atc gag gtg gcc tac agt ctg ctc agg gga ggg tct gat gat        2352
Leu Asp Ile Glu Val Ala Tyr Ser Leu Leu Arg Gly Gly Ser Asp Asp
            770                 775                 780 agc agc aag gat ccc atc gat gtc aac tat gag aag ctc aaa act gac        2400
Ser Ser Lys Asp Pro Ile Asp Val Asn Tyr Glu Lys Leu Lys Thr Asp
785                 790                 795                 800 att aag gtg gtt gac aga gat tct gaa gaa gcc gag atc atc agg aag        2448
Ile Lys Val Val Asp Arg Asp Ser Glu Glu Ala Glu Ile Ile Arg Lys
                    805                 810                 815 tat gtt aag aac act cat gca acc aca cac agt gcg tat gac ttg gaa        2496
```

-continued

```
Tyr Val Lys Asn Thr His Ala Thr Thr His Ser Ala Tyr Asp Leu Glu
        820                 825                 830 gtc atc gat atc ttt aag ata gag cgt gaa ggc gaa tgc cag cgt tac     2544
Val Ile Asp Ile Phe Lys Ile Glu Arg Glu Gly Glu Cys Gln Arg Tyr
        835                 840                 845 aag ccc ttt aag cag ctt cat aac cga aga ttg ctg tgg cac ggg tcc     2592
Lys Pro Phe Lys Gln Leu His Asn Arg Arg Leu Leu Trp His Gly Ser
850                 855                 860 agg acc acc aac ttt gct ggg atc ctg tcc cag ggt ctt cgg ata gcc     2640
Arg Thr Thr Asn Phe Ala Gly Ile Leu Ser Gln Gly Leu Arg Ile Ala
865                 870                 875                 880 ccg cct gaa gcg ccc gtg aca ggc tac atg ttt ggt aaa ggg atc tat     2688
Pro Pro Glu Ala Pro Val Thr Gly Tyr Met Phe Gly Lys Gly Ile Tyr
                885                 890                 895 ttc gct gac atg gtc tcc aag agt gcc aac tac tac cat acg tct cag     2736
Phe Ala Asp Met Val Ser Lys Ser Ala Asn Tyr Tyr His Thr Ser Gln
            900                 905                 910 gga gac cca ata ggc tta atc ctg ttg gga gaa gtt gcc ctt gga aac     2784
Gly Asp Pro Ile Gly Leu Ile Leu Leu Gly Glu Val Ala Leu Gly Asn
        915                 920                 925 atg tat gaa ctg aag cac gct tca cat atc agc agg tta ccc aag ggc     2832
Met Tyr Glu Leu Lys His Ala Ser His Ile Ser Arg Leu Pro Lys Gly
930                 935                 940 aag cac agt gtc aaa ggt ttg ggc aaa act acc cct gat cct tca gct     2880
Lys His Ser Val Lys Gly Leu Gly Lys Thr Thr Pro Asp Pro Ser Ala
945                 950                 955                 960 aac att agt ctg gat ggt gta gac gtt cct ctt ggg acc ggg att tca     2928
Asn Ile Ser Leu Asp Gly Val Asp Val Pro Leu Gly Thr Gly Ile Ser
                965                 970                 975 tct ggt gtg ata gac acc tct cta cta tat aac gag tac att gtc tat     2976
Ser Gly Val Ile Asp Thr Ser Leu Leu Tyr Asn Glu Tyr Ile Val Tyr
            980                 985                 990 gat att gct cag gta aat ctg aag tat ctg ctg aaa ctg aaa ttc aat     3024
Asp Ile Ala Gln Val Asn Leu Lys Tyr Leu Leu Lys Leu Lys Phe Asn
        995                 1000                1005 ttt aag acc tcc ctg tgg taa                                         3045
Phe Lys Thr Ser Leu Trp
    1010
```

<210> SEQ ID NO 25
<211> LENGTH: 1014
<212> TYPE: PRT
<213> ORGANISM: Homo sapiens

<400> SEQUENCE: 25

```
Met Ala Glu Ser Ser Asp Lys Leu Tyr Arg Val Glu Tyr Ala Lys Ser
 1               5                  10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95

Lys Gly Gln Asp Gly Ile Gly Ser Lys Ala Glu Lys Thr Leu Gly Asp
            100                 105                 110
```

-continued

```
Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
        130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
                260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
        290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
                340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
        435                 440                 445

Ala Asn Ile Arg Val Val Ser Glu Asp Phe Leu Gln Asp Val Ser Ala
        450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Ser Lys Gly Gln Val Lys
                500                 505                 510

Glu Glu Gly Ile Asn Lys Ser Glu Lys Arg Met Lys Leu Thr Leu Lys
        515                 520                 525
```

-continued

```
Gly Gly Ala Ala Val Asp Pro Asp Ser Gly Leu Glu His Ser Ala His
        530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu Gln Phe Met Lys Leu Tyr Glu Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
    770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Ser Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
    850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Tyr His Thr Ser Gln
            900                 905                 910

Gly Asp Pro Ile Gly Leu Ile Leu Leu Gly Glu Val Ala Leu Gly Asn
        915                 920                 925

Met Tyr Glu Leu Lys His Ala Ser His Ile Ser Arg Leu Pro Lys Gly
    930                 935                 940

Lys His Ser Val Lys Gly Leu Gly Lys Thr Thr Pro Asp Pro Ser Ala
```

```
                           945                 950                 955                 960
Asn Ile Ser Leu Asp Gly Val Asp Val Pro Leu Gly Thr Gly Ile Ser
                        965                 970                 975

Ser Gly Val Ile Asp Thr Ser Leu Leu Tyr Asn Glu Tyr Ile Val Tyr
            980                 985                 990

Asp Ile Ala Gln Val Asn Leu Lys Tyr Leu Leu Lys Leu Lys Phe Asn
        995                 1000                1005

Phe Lys Thr Ser Leu Trp
    1010

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 26
cgtcgaccca tggcggagtc ttcggataag ctctatcga                              39

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 27
ggaaacgcgt ttggtgccag gatttactgt cagcttctt                              39

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 28
ttgaaacgcg ttccagagtc acagctagat cttcgggta                              39

<210> SEQ ID NO 29
<211> LENGTH: 88
<212> TYPE: DNA
<213> ORGANISM: Artificial Sequence
<220> FEATURE:
<223> OTHER INFORMATION: Description of Artificial Sequence: Primer

<400> SEQUENCE: 29
gtctcgaaag cggccgctta gcctccgaac tgtggatgcc tccacgccca cagctgaagg       60
aaattaaact gaacctttaa aaggtacc                                          88

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 30
tttgttcgcc cagactc                                                      17

<210> SEQ ID NO 31
<211> LENGTH: 22
```

```
<212> TYPE: DNA
<213> ORGANISM: Artificial Sequence
<220> FEATURE:
<223> OTHER INFORMATION: Description of Artificial Sequence: Primer

<400> SEQUENCE: 31
tatgtttcag gttcaggggg ag                                          22

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
gcggaagctg gaggagtgac                                             20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
gtcactcctc cagcttccgc                                             20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 34
aagccctgaa gaagcagctc                                             20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
gagctgcttc ttcagggctt                                             20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
cagacaccca accggaagga                                             20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
```

```
tccttccggt tgggtgtctg                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
tccgcctcca ccaagagcct                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 39
aggctcttgg tggaggcgga                                              20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 40
tggcctggtg gacatcgtta                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 41
taacgatgtc caccaggcca                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 42
gtattcttta ggcgagaggc                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
tgacgaagtg ggcagaactg                                              20

<210> SEQ ID NO 44
<211> LENGTH: 21
<212> TYPE: DNA
<213> ORGANISM: Artificial Sequence
```

```
<220> FEATURE:
<223> OTHER INFORMATION: Description of Artificial Sequence: Primer

<400> SEQUENCE: 44
gagcaccccc tggaccagca c                                              21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 45
acagcgacta taccatgacc                                                20

<210> SEQ ID NO 46
<211> LENGTH: 3200
<212> TYPE: DNA
<213> ORGANISM: Artificial Sequence
<220> FEATURE:
<223> OTHER INFORMATION: Description of Artificial Sequence:
      hPARP1/hPARP2 Fusion

<400> SEQUENCE: 46
atgagaggct cccatcacca tcaccatcac gattacgata tcccaacgac cgaaaacctg      60
tattttcagg gcgccatgga tccggaattc aaaggcctac gtcgacccat ggcggagtct     120
tcggataagc tctatcgagt cgagtacgcc aagagcgggc gcgcctcttg caagaaatgt     180
agcgagagca tccccaagga ctcgctccgg atggccatca tggtgcagtc gcccatgttt     240
gatggaaaag tcccacactg gtaccacttc tcctgcttct ggaaggtggg ccactccatc     300
cggcaccctg acgttgaggt ggatgggttc tctgagcttc ggtgggatga ccagcagaaa     360
gtcaagaaga cagcggaagc tggaggagtg acaggcaaag ccaggatgg aattggtagc     420 aaggcagaga agactctggg tgactttgca gcagagtatg tcaagtccaa cagaagtacg     480 tgcaagggt gtatggagaa gatagaaaag gccaggtgc cctgtccaa gagatggtg       540 gacccggaga agccacagct aggcatgatt gaccgctggt accatccagg ctgctttgtc     600
aagaacaggg aggagctggg tttccggccc gagtacagtg cgagtcagct caaggcttc      660 agcctccttg ctacagagga taaagaagcc ctgaagaagc agctcccagg agtcaagagt     720
gaaggaaaga gtaaaggcga tgaggtggat ggagtggatg aagtggcgaa gagaaatct      780 aaaaagaaa aagacaagga tagtaagctt gaaaagccc taaaggctca gaacgacctg      840
atctggaaca tcaaggacga gctaaagaaa gtgtgttcaa ctaatgacct gaaggagcta     900
ctcatcttca caagcagca agtgccttct ggggagtcgg cgatcttgga ccgagtagct     960
gatggcatgg tgttcggtgc cctccttccc tgcgaggaat gctcgggtca gctggtcttc    1020
aagagcgatg cctattactg cactggggac gtcactgcct ggaccaagtg tatggtcaag    1080
acacagacac ccaaccggaa ggagtgggta accccaaagg aattccgaga atctcttac    1140 ctcaagaaat tgaaggttaa aaagcaggac cgtatattcc ccccagaaac cagcgcctcc    1200
gtggcggcca cgcctccgcc ctccacagcc tcggctcctg ctgctgtgaa ctcctctgct    1260
tcagcagata agccattatc caacatgaag atcctgactc tcgggaagct gtcccggaac    1320
aaggatgaag tgaaggccat gattgagaaa ctcggggga agttgacggg gacggccaac    1380
aaggcttccc tgtgcatcag caccaaaaag gaggtggaaa agatgaataa gaagatggag    1440
gaagtaaagg aagccaacat ccgagttgtg tctgaggact cctccagga cgtctccgcc    1500
```

-continued

```
tccaccaaga gccttcagga gttgttctta gcgcacatct tgtccccttg gggggcagag    1560
gtgaaggcag agcctgttga agttgtggcc ccaagaggga agtcagggc tgcgctctcc     1620 aaaaaaagca agggccaggt caaggaggaa ggtatcaaca aatctgaaaa gagaatgaaa    1680
ttaactctta aggaggagc agctgtggat cctgattctg gactggaaca ctctgcgcat     1740
gtcctggaga aggtgggaa ggtcttcagt gccacccttg gcctggtgga catcgttaaa    1800
ggaaccaact cctactacaa gctgcagctt ctggaggacg acaaggaaaa caggtattgg    1860
atattcaggt cctgggccg tgtgggtacg gtgatcggta gcaacaaact gaacagatg     1920 ccgtccaagg aggatgccat tgagcacttc atgaaattat atgaagaaaa aaccgggaac    1980
gcttggcact ccaaaaattt cacgaagtat cccaaaaagt tctaccccct ggagattgac    2040
tatggccagg atgaagaggc agtgaagaag ctgacagtaa atcctggcac caaacgcgtt    2100
ccagagtcac agctagatct tcgggtacag gagttaataa agttgatctg taatgttcag    2160
gccatggaag aaatgatgat ggaaatgaag tataatacca gaaagcccc tcttgggaag     2220 ctgacagtgg cgcaaatcaa ggcaggttac cagtctctta agaagattga ggattgtatt    2280
cgggctggcc agcatggacg agctctcatg gaagcatgca atgaattcta caccaggatt    2340
ccgcatgact ttggactccg tactcctcca ctaatccgga cacagaagga actgtcagaa    2400
aaaatacaat tactagaggc tttgggagac attgaaattg ctattaagct ggtgaaaaca    2460
gagctacaaa gccagaaca cccattggac caacactata gaaacctaca ttgtgccttg    2520 cgccccttg accatgaaag ttacgagttc aaagtgattt cccagtacct acaatctacc    2580
catgctccca cacacagcga ctataccatg accttgctgg atttgtttga agtggagaag    2640
gatggtgaga agaagccctt cagagaggac cttcataaca ggatgcttct atggcatggt    2700
tccaggatga gtaactgggt gggaatcttg agccatgggc ttcgaattgc ccacctgaa     2760 gctcccatca caggttacat gtttgggaaa ggaatctact ttgctgacat gtcttccaag    2820
agtgccaatt actgctttgc ctctcgccta aagaatacag gactgctgct cttatcagag    2880
gtagctctag gtcagtgtaa tgaactacta gaggccaatc ctaaggccga aggattgctt    2940
caaggtaaac atagcaccaa ggggctgggc aagatggctc ccagttctgc ccacttcgtc    3000
accctgaatg ggagtacagt gccattagga ccagcaagtg acacaggaat tctgaatcca    3060
gatggttata ccctcaacta caatgaatat attgtatata accccaacca ggtccgtatg    3120
cggtaccttt taaaggttca gtttaatttc cttcagctgt gggcgtggag gcatccacag    3180
ttcggaggct aagcggccgc                                                 3200
```

<210> SEQ ID NO 47
<211> LENGTH: 1063
<212> TYPE: PRT
<213> ORGANISM: Artificial Sequence
<220> FEATURE:
<223> OTHER INFORMATION: Description of Artificial Sequence:
    hPARP1/hPARP2 Fusion

<400> SEQUENCE: 47

```
Met Arg Gly Ser His His His His His His Asp Tyr Asp Ile Pro Thr
 1               5                   10                  15

Thr Glu Asn Leu Tyr Phe Gln Gly Ala Met Asp Pro Glu Phe Lys Gly
            20                  25                  30

Leu Arg Arg Pro Met Ala Glu Ser Ser Asp Lys Leu Tyr Arg Val Glu
        35                  40                  45
```

-continued

```
Tyr Ala Lys Ser Gly Arg Ala Ser Cys Lys Lys Cys Ser Glu Ser Ile
     50                  55                  60

Pro Lys Asp Ser Leu Arg Met Ala Ile Met Val Gln Ser Pro Met Phe
 65                  70                  75                  80

Asp Gly Lys Val Pro His Trp Tyr His Phe Ser Cys Phe Trp Lys Val
                 85                  90                  95

Gly His Ser Ile Arg His Pro Asp Val Glu Val Asp Gly Phe Ser Glu
                100                 105                 110

Leu Arg Trp Asp Asp Gln Gln Lys Val Lys Lys Thr Ala Glu Ala Gly
            115                 120                 125

Gly Val Thr Gly Lys Gly Gln Asp Gly Ile Gly Ser Lys Ala Glu Lys
    130                 135                 140

Thr Leu Gly Asp Phe Ala Ala Glu Tyr Val Lys Ser Asn Arg Ser Thr
145                 150                 155                 160

Cys Lys Gly Cys Met Glu Lys Ile Glu Lys Gly Gln Val Arg Leu Ser
                165                 170                 175

Lys Lys Met Val Asp Pro Glu Lys Pro Gln Leu Gly Met Ile Asp Arg
            180                 185                 190

Trp Tyr His Pro Gly Cys Phe Val Lys Asn Arg Glu Glu Leu Gly Phe
        195                 200                 205

Arg Pro Glu Tyr Ser Ala Ser Gln Leu Lys Gly Phe Ser Leu Leu Ala
    210                 215                 220

Thr Glu Asp Lys Glu Ala Leu Lys Lys Gln Leu Pro Gly Val Lys Ser
225                 230                 235                 240

Glu Gly Lys Ser Lys Gly Asp Glu Val Asp Gly Val Asp Glu Val Ala
                245                 250                 255

Lys Lys Lys Ser Lys Lys Glu Lys Asp Lys Asp Ser Lys Leu Glu Lys
            260                 265                 270

Ala Leu Lys Ala Gln Asn Asp Leu Ile Trp Asn Ile Lys Asp Glu Leu
        275                 280                 285

Lys Lys Val Cys Ser Thr Asn Asp Leu Lys Glu Leu Leu Ile Phe Asn
290                 295                 300

Lys Gln Gln Val Pro Ser Gly Glu Ser Ala Ile Leu Asp Arg Val Ala
305                 310                 315                 320

Asp Gly Met Val Phe Gly Ala Leu Leu Pro Cys Glu Glu Cys Ser Gly
                325                 330                 335

Gln Leu Val Phe Lys Ser Asp Ala Tyr Tyr Cys Thr Gly Asp Val Thr
            340                 345                 350

Ala Trp Thr Lys Cys Met Val Lys Thr Gln Thr Pro Asn Arg Lys Glu
        355                 360                 365

Trp Val Thr Pro Lys Glu Phe Arg Glu Ile Ser Tyr Leu Lys Lys Leu
    370                 375                 380

Lys Val Lys Lys Gln Asp Arg Ile Phe Pro Pro Glu Thr Ser Ala Ser
385                 390                 395                 400

Val Ala Ala Thr Pro Pro Pro Ser Thr Ala Ser Ala Pro Ala Ala Val
                405                 410                 415

Asn Ser Ser Ala Ser Ala Asp Lys Pro Leu Ser Asn Met Lys Ile Leu
            420                 425                 430

Thr Leu Gly Lys Leu Ser Arg Asn Lys Asp Glu Val Lys Ala Met Ile
        435                 440                 445

Glu Lys Leu Gly Gly Lys Leu Thr Gly Thr Ala Asn Lys Ala Ser Leu
    450                 455                 460

Cys Ile Ser Thr Lys Lys Glu Val Glu Lys Met Asn Lys Lys Met Glu
```

-continued

```
465                 470                 475                 480
Glu Val Lys Glu Ala Asn Ile Arg Val Val Ser Glu Asp Phe Leu Gln
                    485                 490                 495
Asp Val Ser Ala Ser Thr Lys Ser Leu Gln Glu Leu Phe Leu Ala His
                500                 505                 510
Ile Leu Ser Pro Trp Gly Ala Glu Val Lys Ala Glu Pro Val Glu Val
                515                 520                 525
Val Ala Pro Arg Gly Lys Ser Gly Ala Ala Leu Ser Lys Lys Ser Lys
            530                 535                 540
Gly Gln Val Lys Glu Glu Gly Ile Asn Lys Ser Glu Lys Arg Met Lys
545                 550                 555                 560
Leu Thr Leu Lys Gly Gly Ala Ala Val Asp Pro Asp Ser Gly Leu Glu
                565                 570                 575
His Ser Ala His Val Leu Glu Lys Gly Gly Lys Val Phe Ser Ala Thr
                580                 585                 590
Leu Gly Leu Val Asp Ile Val Lys Gly Thr Asn Ser Tyr Tyr Lys Leu
            595                 600                 605
Gln Leu Leu Glu Asp Asp Lys Glu Asn Arg Tyr Trp Ile Phe Arg Ser
    610                 615                 620
Trp Gly Arg Val Gly Thr Val Ile Gly Ser Asn Lys Leu Glu Gln Met
625                 630                 635                 640
Pro Ser Lys Glu Asp Ala Ile Glu His Phe Met Lys Leu Tyr Glu Glu
                645                 650                 655
Lys Thr Gly Asn Ala Trp His Ser Lys Asn Phe Thr Lys Tyr Pro Lys
                660                 665                 670
Lys Phe Tyr Pro Leu Glu Ile Asp Tyr Gly Gln Asp Glu Glu Ala Val
            675                 680                 685
Lys Lys Leu Thr Val Asn Pro Gly Thr Lys Arg Val Pro Glu Ser Gln
        690                 695                 700
Leu Asp Leu Arg Val Gln Glu Leu Ile Lys Leu Ile Cys Asn Val Gln
705                 710                 715                 720
Ala Met Glu Glu Met Met Met Glu Met Lys Tyr Asn Thr Lys Lys Ala
                725                 730                 735
Pro Leu Gly Lys Leu Thr Val Ala Gln Ile Lys Ala Gly Tyr Gln Ser
                740                 745                 750
Leu Lys Lys Ile Glu Asp Cys Ile Arg Ala Gly Gln His Gly Arg Ala
            755                 760                 765
Leu Met Glu Ala Cys Asn Glu Phe Tyr Thr Arg Ile Pro His Asp Phe
770                 775                 780
Gly Leu Arg Thr Pro Pro Leu Ile Arg Thr Gln Lys Glu Leu Ser Glu
785                 790                 795                 800
Lys Ile Gln Leu Leu Glu Ala Leu Gly Asp Ile Glu Ile Ala Ile Lys
                805                 810                 815
Leu Val Lys Thr Glu Leu Gln Ser Pro Glu His Pro Leu Asp Gln His
                820                 825                 830
Tyr Arg Asn Leu His Cys Ala Leu Arg Pro Leu Asp His Glu Ser Tyr
            835                 840                 845
Glu Phe Lys Val Ile Ser Gln Tyr Leu Gln Ser Thr His Ala Pro Thr
        850                 855                 860
His Ser Asp Tyr Thr Met Thr Leu Leu Asp Leu Phe Glu Val Glu Lys
865                 870                 875                 880
Asp Gly Glu Lys Glu Ala Phe Arg Glu Asp Leu His Asn Arg Met Leu
                885                 890                 895
```

```
Leu Trp His Gly Ser Arg Met Ser Asn Trp Val Gly Ile Leu Ser His
        900                 905                 910

Gly Leu Arg Ile Ala Pro Pro Glu Ala Pro Ile Thr Gly Tyr Met Phe
    915                 920                 925

Gly Lys Gly Ile Tyr Phe Ala Asp Met Ser Ser Lys Ser Ala Asn Tyr
    930                 935                 940

Cys Phe Ala Ser Arg Leu Lys Asn Thr Gly Leu Leu Leu Ser Glu
945                 950                 955                 960

Val Ala Leu Gly Gln Cys Asn Glu Leu Leu Glu Ala Asn Pro Lys Ala
                965                 970                 975

Glu Gly Leu Leu Gln Gly Lys His Ser Thr Lys Gly Leu Gly Lys Met
            980                 985                 990

Ala Pro Ser Ser Ala His Phe Val  Thr Leu Asn Gly Ser  Thr Val Pro
        995                 1000                1005

Leu Gly  Pro Ala Ser Asp Thr  Gly Ile Leu Asn Pro  Asp Gly Tyr Thr
    1010                1015                1020

Leu  Asn Tyr Asn Glu Tyr  Ile Val Tyr Asn Pro  Asn Gln Val Arg Met
1025                1030                1035                1040

Arg Tyr Leu Leu Lys  Val Gln Phe Asn Phe  Leu Gln Leu Trp Ala  Trp
            1045                1050                1055

Arg His Pro Gln  Phe Gly Gly
            1060

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence:Primer

<400> SEQUENCE: 48
cgtcgaccca tggcggcgcg gcggcgacgg agcaccggc                              39

<210> SEQ ID NO 49
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 49
tggaacgcgt ttcaagggag atttaagaga ttcctctttt                             39

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 50
ccaggtccgt atgcggtacc                                                   20

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 51
```
gccacgatgg gtaccgcggc cgctcaccac agctgaagg                                    39

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 52
ggtgacgaag tgggcagaac                                                         20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 53
ttctgcccac ttcgtcaccc                                                         20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 54
cgcaaggcac aatgtaggtt                                                         20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 55
gcctctcgcc taaagaatac                                                         20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 56
aagcaatcct tcggccttag                                                         20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 57
agttctgccc acttcgtcac                                                         20

<210> SEQ ID NO 58
<211> LENGTH: 1874
<212> TYPE: DNA

<213> ORGANISM: Artificial Sequence
<220> FEATURE:
<223> OTHER INFORMATION: Description of Artificial Sequence:hPARP2 + His
      Tag

<400> SEQUENCE: 58

| | | | | | |
|---|---|---|---|---|---|
| atgagaggct | cccatcacca | tcaccatcac | gattacgata | tcccaacgac | cgaaaacctg | 60 |
| tattttcagg | gcgccatgga | tccggaattc | aaaggcctac | gtcgaccccat | ggcggcgcgg | 120 |
| cggcgacgga | gcaccggcgg | cggcagggcg | agagcattaa | atgaaagcaa | aagagttaat | 180 |
| aatggcaaca | cggctccaga | agactcttcc | cctgccaaga | aaactcgtag | atgccagaga | 240 |
| caggagtcga | aaaagatgcc | tgtggctgga | ggaaaagcta | ataaggacag | gacagaagac | 300 |
| aagcaagatg | gtatgccagg | aaggtcatgg | gccagcaaaa | gggtctccga | atctgtgaag | 360 |
| gccttgctgt | taaagggcaa | agctcctgtg | gacccagagt | gtacagccaa | ggtggggaag | 420 |
| gctcatgtgt | attgtgaagg | aaatgatgtc | tatgatgtca | tgctaaatca | gaccaatctc | 480 |
| cagttcaaca | acaacaagta | ctatctgatt | cagctattag | aagatgatgc | ccagaggaac | 540 |
| ttcagtgttt | ggatgagatg | gggccgagtt | gggaaaatgg | gacagcacag | cctggtggct | 600 |
| tgttcaggca | atctcaacaa | ggccaaggaa | atctttcaga | gaaaattcct | tgacaaaacg | 660 |
| aaaaacaatt | gggaagatcg | agaaaagttt | gagaaggtgc | ctggaaaata | tgatatgcta | 720 |
| cagatggact | atgccaccaa | tactcaggat | gaagaggaaa | caaagaaaga | ggaatctctt | 780 |
| aaatctccct | gaagccaga | gtcacagcta | gatcttcggg | tacaggagtt | aataaagttg | 840 |
| atctgtaatg | ttcaggccat | ggaagaaatg | atgatgaaa | tgaagtataa | taccaagaaa | 900 |
| gccctcttg | ggaagctgac | agtggcgcaa | atcaaggcag | gttaccagtc | tcttaagaag | 960 |
| attgaggatt | gtattcgggc | tggccagcat | ggacgagctc | tcatggaagc | atgcaatgaa | 1020 |
| ttctacacca | ggattccgca | tgactttgga | ctccgtactc | ctccactaat | ccggacacag | 1080 |
| aaggaactgt | cagaaaaaat | acaattacta | gaggctttgg | gagacattga | aattgctatt | 1140 |
| aagctggtga | aaacagagct | acaaagccca | gaacacccat | tggaccaaca | ctatagaaac | 1200 |
| ctacattgtg | ccttgcgccc | ccttgaccat | gaaagttacg | agttcaaagt | gatttcccag | 1260 |
| tacctacaat | ctacccatgc | tcccacacac | agcgactata | ccatgacctt | gctggatttg | 1320 |
| tttgaagtgg | agaaggatgg | tgagaaagaa | gccttcagag | aggaccttca | taacaggatg | 1380 |
| cttctatggc | atggttccag | gatgagtaac | tgggtgggaa | tcttgagcca | tgggcttcga | 1440 |
| attgccccac | ctgaagctcc | catcacaggt | tacatgtttg | ggaaaggaat | ctactttgct | 1500 |
| gacatgtctt | ccaagagtgc | caattactgc | tttgcctctc | gcctaaagaa | tacaggactg | 1560 |
| ctgctcttat | cagaggtagc | tctaggtcag | tgtaatgaac | tactagaggc | caatcctaag | 1620 |
| gccgaaggat | tgcttcaagg | taaacatagc | accaagggc | tgggcaagat | ggctcccagt | 1680 |
| tctgcccact | tcgtcaccct | gaatgggagt | acagtgccat | taggaccagc | aagtgacaca | 1740 |
| ggaattctga | atccagatgg | ttataccctc | aactacaatg | aatatattgt | atataacccc | 1800 |
| aaccaggtcc | gtatgcggta | ccttttaaag | gttcagttta | atttccttca | gctgtggtga | 1860 |
| gcggccgcgg | tacc | | | | | 1874 |

<210> SEQ ID NO 59
<211> LENGTH: 619
<212> TYPE: PRT
<213> ORGANISM: Artificial Sequence
<220> FEATURE:
<223> OTHER INFORMATION: Description of Artificial Sequence:hPARP2 + His
      Tag

```
<400> SEQUENCE: 59

Met Arg Gly Ser His His His His His His Asp Tyr Asp Ile Pro Thr
  1               5                  10                  15

Thr Glu Asn Leu Tyr Phe Gln Gly Ala Met Asp Pro Glu Phe Lys Gly
             20                  25                  30

Leu Arg Arg Pro Met Ala Ala Arg Arg Arg Ser Thr Gly Gly Gly
         35                  40                  45

Arg Ala Arg Ala Leu Asn Glu Ser Lys Arg Val Asn Asn Gly Asn Thr
     50                  55                  60

Ala Pro Glu Asp Ser Ser Pro Ala Lys Thr Arg Arg Cys Gln Arg
 65                  70                  75                  80

Gln Glu Ser Lys Lys Met Pro Val Ala Gly Lys Ala Asn Lys Asp
                 85                  90                  95

Arg Thr Glu Asp Lys Gln Asp Gly Met Pro Gly Arg Ser Trp Ala Ser
            100                 105                 110

Lys Arg Val Ser Glu Ser Val Lys Ala Leu Leu Lys Gly Lys Ala
            115                 120                 125

Pro Val Asp Pro Glu Cys Thr Ala Lys Val Gly Lys Ala His Val Tyr
        130                 135                 140

Cys Glu Gly Asn Asp Val Tyr Asp Val Met Leu Asn Gln Thr Asn Leu
145                 150                 155                 160

Gln Phe Asn Asn Asn Lys Tyr Tyr Leu Ile Gln Leu Leu Glu Asp Asp
                165                 170                 175

Ala Gln Arg Asn Phe Ser Val Trp Met Arg Trp Gly Arg Val Gly Lys
            180                 185                 190

Met Gly Gln His Ser Leu Val Ala Cys Ser Gly Asn Leu Asn Lys Ala
        195                 200                 205

Lys Glu Ile Phe Gln Lys Lys Phe Leu Asp Lys Thr Lys Asn Asn Trp
    210                 215                 220

Glu Asp Arg Glu Lys Phe Glu Lys Val Pro Gly Lys Tyr Asp Met Leu
225                 230                 235                 240

Gln Met Asp Tyr Ala Thr Asn Thr Gln Asp Glu Glu Thr Lys Lys
                245                 250                 255

Glu Glu Ser Leu Lys Ser Pro Leu Lys Pro Glu Ser Gln Leu Asp Leu
            260                 265                 270

Arg Val Gln Glu Leu Ile Lys Leu Ile Cys Asn Val Gln Ala Met Glu
        275                 280                 285

Glu Met Met Met Glu Met Lys Tyr Asn Thr Lys Lys Ala Pro Leu Gly
    290                 295                 300

Lys Leu Thr Val Ala Gln Ile Lys Ala Gly Tyr Gln Ser Leu Lys Lys
305                 310                 315                 320

Ile Glu Asp Cys Ile Arg Ala Gly Gln His Gly Arg Ala Leu Met Glu
                325                 330                 335

Ala Cys Asn Glu Phe Tyr Thr Arg Ile Pro His Asp Phe Gly Leu Arg
            340                 345                 350

Thr Pro Pro Leu Ile Arg Thr Gln Lys Glu Leu Ser Glu Lys Ile Gln
        355                 360                 365

Leu Leu Glu Ala Leu Gly Asp Ile Glu Ile Ala Ile Lys Leu Val Lys
    370                 375                 380

Thr Glu Leu Gln Ser Pro Glu His Pro Leu Asp Gln His Tyr Arg Asn
385                 390                 395                 400

Leu His Cys Ala Leu Arg Pro Leu Asp His Glu Ser Tyr Glu Phe Lys
```

```
                    405                 410                 415
Val Ile Ser Gln Tyr Leu Gln Ser Thr His Ala Pro Thr His Ser Asp
                420                 425                 430

Tyr Thr Met Thr Leu Leu Asp Leu Phe Glu Val Glu Lys Asp Gly Glu
            435                 440                 445

Lys Glu Ala Phe Arg Glu Asp Leu His Asn Arg Met Leu Leu Trp His
    450                 455                 460

Gly Ser Arg Met Ser Asn Trp Val Gly Ile Leu Ser His Gly Leu Arg
465                 470                 475                 480

Ile Ala Pro Pro Glu Ala Pro Ile Thr Gly Tyr Met Phe Gly Lys Gly
                485                 490                 495

Ile Tyr Phe Ala Asp Met Ser Ser Lys Ser Ala Asn Tyr Cys Phe Ala
            500                 505                 510

Ser Arg Leu Lys Asn Thr Gly Leu Leu Leu Leu Ser Glu Val Ala Leu
        515                 520                 525

Gly Gln Cys Asn Glu Leu Leu Glu Ala Asn Pro Lys Ala Glu Gly Leu
    530                 535                 540

Leu Gln Gly Lys His Ser Thr Lys Gly Leu Gly Lys Met Ala Pro Ser
545                 550                 555                 560

Ser Ala His Phe Val Thr Leu Asn Gly Ser Thr Val Pro Leu Gly Pro
                565                 570                 575

Ala Ser Asp Thr Gly Ile Leu Asn Pro Asp Gly Tyr Thr Leu Asn Tyr
            580                 585                 590

Asn Glu Tyr Ile Val Tyr Asn Pro Asn Gln Val Arg Met Arg Tyr Leu
        595                 600                 605

Leu Lys Val Gln Phe Asn Phe Leu Gln Leu Trp
    610                 615

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 60
ggagacattg aaattgctat                                              20

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 61
gaacacccat tggaccaaca c                                            21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 62
gaggtatata ttaatgtatc g                                            21

<210> SEQ ID NO 63
```

```
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 63
gatttaatct gtatcagg                                                   18

<210> SEQ ID NO 64
<211> LENGTH: 738
<212> TYPE: DNA
<213> ORGANISM: Artificial Sequence
<220> FEATURE:
<223> OTHER INFORMATION: Description of Artificial Sequence:hPARP2
      Fragment + C-Terminal His Tag

<400> SEQUENCE: 64
ggagacattg aaattgctat taagctggtg aaaacagagc tacaaagccc agaacaccca      60
ttggaccaac actatagaaa cctacattgt gccttgcgcc cccttgacca tgaaagttac    120
gagttcaaag tgatttccca gtacctacaa tctacccatg ctcccacaca cagcgactat    180
accatgacct tgctggattt gtttgaagtg gagaaggatg gtgagaaaga agccttcaga    240
gaggaccttc ataacaggat gcttctatgg catggttcca ggatgagtaa ctgggtggga    300
atcttgagcc atgggcttcg aattgcccca cctgaagctc ccatcacagg ttacatgttt    360
gggaaaggaa tctactttgc tgacatgtct tccaagagtg ccaattactg ctttgcctct    420
cgcctaaaga atacaggact gctgctctta tcagaggtag ctctaggtca gtgtaatgaa    480
ctactagagg ccaatcctaa ggccgaagga ttgcttcaag gtaaacatag caccaagggg    540
ctgggcaaga tggctcccag ttctgcccac ttcgtcaccc tgaatgggag tacagtgcca    600
ttaggaccag caagtgacac aggaattctg aatccagatg gttatacccct caactacaat    660 gaatatattg tatataaccc caaccaggtc cgtatgcggt accttttaaa ggttcagttt    720
aatttccttc agctgtgg                                                  738

<210> SEQ ID NO 65
<211> LENGTH: 275
<212> TYPE: PRT
<213> ORGANISM: Artificial Sequence
<220> FEATURE:
<223> OTHER INFORMATION: Description of Artificial Sequence:hPARP2
      Fragment + C-Terminal His Tag

<400> SEQUENCE: 65

Gly Asp Ile Glu Ile Ala Ile Lys Leu Val Lys Thr Glu Leu Gln Ser
  1               5                  10                  15

Pro Glu His Pro Leu Asp Gln His Tyr Arg Asn Leu His Cys Ala Leu
                 20                  25                  30

Arg Pro Leu Asp His Glu Ser Tyr Glu Phe Lys Val Ile Ser Gln Tyr
             35                  40                  45

Leu Gln Ser Thr His Ala Pro Thr His Ser Asp Tyr Thr Met Thr Leu
         50                  55                  60

Leu Asp Leu Phe Glu Val Glu Lys Asp Gly Glu Lys Glu Ala Phe Arg
 65                  70                  75                  80

Glu Asp Leu His Asn Arg Met Leu Leu Trp His Gly Ser Arg Met Ser
                 85                  90                  95

Asn Trp Val Gly Ile Leu Ser His Gly Leu Arg Ile Ala Pro Pro Glu
                100                 105                 110
```

```
Ala Pro Ile Thr Gly Tyr Met Phe Gly Lys Gly Ile Tyr Phe Ala Asp
        115                 120                 125
Met Ser Ser Lys Ser Ala Asn Tyr Cys Phe Ala Ser Arg Leu Lys Asn
    130                 135                 140
Thr Gly Leu Leu Leu Ser Glu Val Ala Leu Gly Gln Cys Asn Glu
145                 150                 155                 160
Leu Leu Glu Ala Asn Pro Lys Ala Glu Gly Leu Leu Gln Gly Lys His
                165                 170                 175
Ser Thr Lys Gly Leu Gly Lys Met Ala Pro Ser Ser Ala His Phe Val
                180                 185                 190
Thr Leu Asn Gly Ser Thr Val Pro Leu Gly Pro Ala Ser Asp Thr Gly
                195                 200                 205
Ile Leu Asn Pro Asp Gly Tyr Thr Leu Asn Tyr Asn Glu Tyr Ile Val
        210                 215                 220
Tyr Asn Pro Asn Gln Val Arg Met Arg Tyr Leu Leu Lys Val Gln Phe
225                 230                 235                 240
Asn Phe Leu Gln Leu Trp Lys Gly Glu Phe Glu Ala Tyr Val Glu Gln
                245                 250                 255
Lys Leu Ile Ser Glu Glu Asp Leu Asn Ser Ala Val Asp His His His
                260                 265                 270
His His His
        275

<210> SEQ ID NO 66
<211> LENGTH: 687
<212> TYPE: DNA
<213> ORGANISM: Artificial Sequence
<220> FEATURE:
<223> OTHER INFORMATION: Description of Artificial Sequence:hPARP2
      Fragment + C-Terminal His Tag

<400> SEQUENCE: 66
gaacacccat tggaccaaca ctatagaaac ctacattgtg ccttgcgccc ccttgaccat      60
gaaagttacg agttcaaagt gatttcccag tacctacaat ctaccatgc tcccacacac    120
agcgactata ccatgacctt gctggatttg tttgaagtgg agaaggatgg tgagaaagaa    180
gccttcagag aggaccttca taacaggatg cttctatggc atggttccag gatgagtaac    240
tgggtgggaa tcttgagcca tgggcttcga attgccccac ctgaagctcc catcacaggt    300
tacatgtttg ggaaaggaat ctactttgct gacatgtctt ccaagagtgc aattactgc    360
tttgcctctc gcctaaagaa tacaggactg ctgctcttat cagaggtagc tctaggtcag    420
tgtaatgaac tactagaggc caatcctaag gccgaaggat tgcttcaagg taaacatagc    480
accaagggc tgggcaagat ggctcccagt tctgcccact tcgtcaccct gaatgggagt    540
acagtgccat taggaccagc aagtgacaca ggaattctga atccagatgg ttatacccctc    600
aactacaatg aatatattgt atataacccc aaccaggtcc gtatgcggta ccttttaaag    660
gttcagttta atttccttca gctgtgg                                        687

<210> SEQ ID NO 67
<211> LENGTH: 258
<212> TYPE: PRT
<213> ORGANISM: Artificial Sequence
<220> FEATURE:
<223> OTHER INFORMATION: Description of Artificial Sequence:hPARP2
      Fragment + C-Terminal His Tag

<400> SEQUENCE: 67
```

-continued

Glu His Pro Leu Asp Gln His Tyr Arg Asn Leu His Cys Ala Leu Arg
 1               5                  10                  15

Pro Leu Asp His Glu Ser Tyr Glu Phe Lys Val Ile Ser Gln Tyr Leu
                20                  25                  30

Gln Ser Thr His Ala Pro Thr His Ser Asp Tyr Thr Met Thr Leu Leu
            35                  40                  45

Asp Leu Phe Glu Val Glu Lys Asp Gly Glu Lys Glu Ala Phe Arg Glu
        50                  55                  60

Asp Leu His Asn Arg Met Leu Leu Trp His Gly Ser Arg Met Ser Asn
 65                 70                  75                  80

Trp Val Gly Ile Leu Ser His Gly Leu Arg Ile Ala Pro Pro Glu Ala
                85                  90                  95

Pro Ile Thr Gly Tyr Met Phe Gly Lys Gly Ile Tyr Phe Ala Asp Met
                100                 105                 110

Ser Ser Lys Ser Ala Asn Tyr Cys Phe Ala Ser Arg Leu Lys Asn Thr
            115                 120                 125

Gly Leu Leu Leu Ser Glu Val Ala Leu Gly Gln Cys Asn Glu Leu
        130                 135                 140

Leu Glu Ala Asn Pro Lys Ala Glu Gly Leu Leu Gln Gly Lys His Ser
145                 150                 155                 160

Thr Lys Gly Leu Gly Lys Met Ala Pro Ser Ser Ala His Phe Val Thr
                165                 170                 175

Leu Asn Gly Ser Thr Val Pro Leu Gly Pro Ala Ser Asp Thr Gly Ile
                180                 185                 190

Leu Asn Pro Asp Gly Tyr Thr Leu Asn Tyr Asn Glu Tyr Ile Val Tyr
                195                 200                 205

Asn Pro Asn Gln Val Arg Met Arg Tyr Leu Leu Lys Val Gln Phe Asn
        210                 215                 220

Phe Leu Gln Leu Trp Lys Gly Glu Phe Glu Ala Tyr Val Glu Gln Lys
225                 230                 235                 240

Leu Ile Ser Glu Glu Asp Leu Asn Ser Ala Val Asp His His His His
                245                 250                 255

His His

<210> SEQ ID NO 68
<211> LENGTH: 7
<212> TYPE: PRT
<213> ORGANISM: artificial sequence
<220> FEATURE:
<223> OTHER INFORMATION: Common catalytic motif for hPARP proteins
<220> FEATURE:
<221> NAME/KEY: MISC_FEATURE
<222> LOCATION: (2)
<223> OTHER INFORMATION: Xaa = unknown or any amino acid
<220> FEATURE:
<221> NAME/KEY: MISC_FEATURE
<222> LOCATION: (3)
<223> OTHER INFORMATION: Xaa = unknown or any amino acid
<220> FEATURE:
<221> NAME/KEY: MISC_FEATURE
<222> LOCATION: (4)
<223> OTHER INFORMATION: Xaa = unknown or any amino acid

<400> SEQUENCE: 68

Gly Xaa Xaa Xaa Gly Lys Gly
 1               5

HUMAN POLY (ADP-RIBOSE) POLYMERASE 2 MATERIALS AND METHODS

This application claims the benefit of U.S. Provisional Application Serial No. 60/139,543, filed Jun. 16, 1999.

The present invention relates generally to a novel human polypeptide having poly(ADP-ribose) polymerase activity, to polynucleotides encoding the polypeptide, and to methods of using such materials.

BACKGROUND OF THE INVENTION

Regulation of gene function occurs by several mechanisms in eukaryotic cells. Amongst these mechanisms are gene transcription regulation, mRNA translation regulation, and post-translation modification of proteins. Post-translation modification of proteins includes several processes whereby proteins are covalently altered to affect cellular, sub-cellular localization, stability, transport, interaction specificity, enzymatic activity, and numerous other characteristics.

Common and extensively studied covalent modification processes include acetylation, glycosylation, and phosphorylation. Less well characterized is a process that involves the covalent addition of polymers of ADP-ribose to protein targets. The polymer is termed "poly(ADP-ribose)," and the enzyme(s) responsible for this activity have been variously called poly(ADP-ribose) polymerase (PARP), poly(ADP-ribose) synthetase (PARS), or ADP-ribosyl transferase (ADPRT) [Althaus and Richter, *ADP-Ribosylation of Proteins: Enzymology and Biochemical Significance*, Molecular Biochemistry and Biophysics, Springer-Verlag (1987)]. A previously identified PARP gene product (hereinafter "PARP1") is expressed at high levels in the nuclei of cells and is dependent upon DNA damage for activation [Szabó and Dawson, *Trends Pharmacol Sci* 19(7):287–98 (1998)]. Current models hypothesize that PARP1 binds to DNA single or double stranded breaks through an amino terminal DNA binding domain. The binding activates the carboxy terminal catalytic domain and results in the formation of polymers of ADP-ribose on target molecules. PARP1 is itself a target of polyADP-ribosylation by virtue of a centrally located automodification domain. The ribosylation of PARP1 causes dissociation of the PARP1 molecules from the DNA. The entire process of binding, ribosylation, and dissociation occurs very rapidly. It has been suggested that this transient binding of PARP1 to sites of DNA damage may result in the recruitment of DNA repair machinery or may act to suppress recombination long enough for the recruitment of repair machinery [Satoh and Lindahl, *Nature* 356(6367):356–8 (1992)].

The source of ADP-ribose for the PARP reaction is nicotinamide adenine dinucleotide (NAD). NAD is synthesized in cells, from cellular ATP stores and thus high levels of activation of PARP activity can rapidly lead to depletion of cellular energy stores. It has been demonstrated that induction of PARP activity can lead to cell death that is correlated with depletion of cellular NAD and ATP pools [Yamamoto et al., *Nature* 294(5838):284–6 (1981); Sims et al., *Biochemistry* 22(22):5188–94 (1983)]. PARP activity is induced in many instances of oxidative stress or during inflammation. For-example, during reperfusion of ischemic tissues reactive nitric oxide is generated and nitric oxide results in the generation of additional reactive oxygen species including hydrogen peroxide, peroxynitrate and hydroxyl radical [Szabó, *Eur J Pharmacol* 350(1):1–19 (1998)]. These latter species can directly damage DNA and the resulting damage induces activation of PARP activity. Frequently, it appears that sufficient activation of PARP activity occurs so that the cell energy stores are depleted and the cell dies.

A similar mechanism is believed to operate during inflammation when endothelial cells and pro-inflammatory cells synthesize nitric oxide which results in oxidative DNA damage in surrounding cells and the subsequent activation of PARP activity [Szabó 1998, supra]. Such a mechanism is also believed to play a role in tissue damage associated with transient cerebral ischemia, in which excessive NMDA receptor activation mediates DNA damage, which induces excessive PARP activation [Lo et al., *Stroke* 29:830–6 (1998)]. The cell death that results from PARP activation is believed to be a major contributing factor in the extent of tissue damage that results from ischemia/reperfusion injury or from inflammation.

Two lines of evidence suggest that PARP activity is a critical element in those processes. First, chemical inhibitors of PARP activity have been successfully used to reduce tissue damage resulting in animal models of ischemia/reperfusion injury or inflammation. Second, mice in which both alleles of PARP1 have been disabled (PARP1 knockout mice) are resistant to numerous forms of ischemia/reperfusion injury and detrimental effects of inflammation. Because of those observations, potent small molecule inhibitors of PARP activity have great potential as clinical drug candidates in several indications.

The experimental data derived from the PARP1 knockout mice suggest that inhibitors of PARP1 function may be clinically beneficial. However, a recent report demonstrates that PARP1 knockout mice are not devoid of DNA damage-inducible PARP activity [Shieh et al., *J Biol Chem* 273(46):30069–72 (1998)]. A recently identified gene product, tankyrase, has been shown to have poly(ADP) ribosylation activity [Smith et al., *Science* 282(5393):1484–7 (1998)]. Tankyrase activity however, does not appear to be inducible by DNA damage and thus is unlikely to account for the activity observed in PARP1 knockout mice. It has been suggested that the residual DNA damage induced PARP activity in PARP1 knockout mice may be due to the activity of a second PARP gene, which has been identified in the mouse and named murine PARP2 [Shieh et al. (1998), supra]. The existence of multiple PARP genes in mammals suggests that appropriate drug design for human therapeutics requires the identification of additional human gene products with PARP activity. A gene comparable to mouse PARP2 has not previously been identified in humans.

In view of the above considerations, it is clear that existing knowledge is lacking with respect to cellular DNA repair mechanisms, signaling and induction of cell death in response to DNA damage, mechanisms of inflammation, and treatment of inflammation-mediated disease states. Thus, there exists a need in the art for the identification of additional human PARP-like molecules for use in determining the selectivity of therapeutics designed to inhibit PARP function and as targets in their own right for therapeutic intervention in human diseases. The profiling of PARP inhibitors on additional PARP gene products may allow for the PARP-selective drugs, which could be beneficial for particular indications, the reduction of undesirable side effects, or the targeting of therapeutics to selected tissues. Likewise, the identification of hPARP2 will allow for the development of hPARP2 specific therapeutics, which may also have benefits in terms of particular disease indications, the reduction of undesirable side effects, and the targeting of therapeutics to particular tissues. The identification of human hPARP2 would also allow for the development of drugs with the ability to inhibit both PARP activities that may also have therapeutic benefit. Other purposes and advantages of the invention will be readily apparent to the artisan having ordinary skill in the art.

SUMMARY OF THE INVENTION

It has now been discovered that these and other purposes can be achieved by the present invention, which, in one aspect, is a purified and isolated hPARP2 polypeptide comprising an amino acid sequence defined in SEQ ID NO:2 or a functional derivative thereof. The invention also embraces hPARP2 polypeptides encoded by a polynucleotide which hybridizes under stringent (moderately or highly) conditions to the complement of the polynucleotide set out in SEQ ID NO: 2 and a polynucleotide which hybridizes under stringent (moderately or highly) conditions to the complement of a polynucleotide that encodes the polypeptide set out in SEQ ID NO: 1.

In another aspect, the invention further provides polynucleotides encoding the hPARP2 polypeptide defined in SEQ ID NO:2. Preferably, the polynucleotides comprise the nucleotide sequence defined in SEQ ID NO:1. Alternatively, the polynucleotides encoding an hPARP2 polypeptide can be polynucleotides that hybridize under moderately stringent hybridization conditions to the coding or non-coding strand of the polynucleotide of SEQ ID NO:1 or a polynucleotide which hybridizes to the complement of a polynucleotide that encodes the polypeptide set out in SEQ ID NO: 2. In a preferred case, the polynucleotide hybridizes to the complement of the polynucleotide defined in SEQ ID NO:1, under stringent (moderately or highly) hybridization conditions, and encodes a protein that has poly(ADP) polymerase activity or interacts with damaged DNA. The polynucleotides of the invention may be DNA molecules or RNA molecules, and may optionally further comprise a detectable label moiety.

In another aspect, the invention provides expression constructs that comprise an hPARP2-encoding polynucleotide having a nucleotide sequence defined in SEQ ID NO:1 or a polynucleotide which hybridizes to the complement of a polynucleotide that encodes the polypeptide set out in SEQ ID NO: 2. The hPARP2-encoding polynucleotide can be operatively linked to a heterologous promoter. Host cells transformed or transfected with an hparp2-based expression construct are also provided. Also contemplated are methods for producing a polypeptide having an amino acid sequence defined by SEQ ID NO:2, comprising the steps of:

a) growing hPARP2-expressing host cells under conditions appropriate for expression of the polypeptide; and b) isolating the polypeptide from the host cell or the medium in which the host cell is grown.

The invention further provides antibodies that are specifically immunoreactive with the hPARP2 polypeptides described herein. As used herein, "specifically immunoreactive" antibodies embrace those which only recognize the polypeptide (or antibody, as discussed below) of the invention. The antibody can be selected from the group consisting of monoclonal antibodies, polyclonal antibodies, single chain antibodies (scFv antibodies), chimeric antibodies, multifunctional/multispecific antibodies, humanized antibodies, human antibodies, CDR-grafted antibodies, Fab fragments, Fab' fragments, F(ab')$_2$ fragments, Fv fragments, diabodies; linear antibodies; single-chain antibody molecules; and multispecific antibodies formed from antibody fragments. Also provided are cell lines that produce antibodies. Anti-idiotype antibodies specifically immunoreactive with an hPARP2-specific antibody are also contemplated.

In a further aspect, the invention is a method for identifying a specific binding partner of an hPARP2 polypeptide, comprising:

a) contacting the hPARP2 polypeptide with a test compound under conditions that permit binding of the hPARP2 polypeptide and the test compound;

b) detecting binding of the test compound and the hPARP2 polypeptide; and c) identifying the test compound as a specific binding partner of the hPARP2 polypeptide.

The specific binding partner is preferably a compound that modulates a biological activity of the hPARP2 polypeptide. Accordingly, the specific binding partner can be one that inhibits a biological activity of the hPARP2 polypeptide. Alternatively, the specific binding partner can be one that enhances a biological activity of the hPARP2 polypeptide.

In still another aspect, the invention is a method for identifying a specific binding partner of an hparp2 polynucleotide, comprising:

a) contacting the hparp2 polynucleotide with a test compound under conditions that permit binding of the hparp2 polynucleotide and the test compound;

b) detecting binding of the test compound and the hparp2 polynucleotide; and c) identifying the test compound as a specific binding partner of the hparp2 polynucleotide.

Thus, specific binding partner identified by the method is preferably a compound that modulates expression of the hPARP2 polypeptide. The specific binding partner can be one that inhibits expression of the hPARP2 polypeptide or one that enhances expression of the hPARP2 polypeptide.

Furthermore, in another aspect, the invention is a method of treating a human subject having a medical condition mediated by a poly(ADP-ribose) polymerase, comprising administering to the subject an hPARP2 inhibitory compound in an amount effective for inhibiting hPARP2 in the subject. The method may further comprise administering to the subject an hPARP1 inhibitory compound in an amount effective for inhibiting hPARP1 in the subject.

In another aspect, the invention is a method of treating a human subject having a disorder selected from the group consisting of inflammatory disorders, neurological disorders, cardiovascular disorders, and disorders of neoplastic tissue growth. Preferably the disorder is an inflammatory disorder or is associated with inflammatory cell activation. For example, the medical condition can be a condition that is characterized by reperfusion injury. Illustrative disorders characterized by reperfusion injury include ischemic stroke, hemorrhagic shock, myocardial ischemia or infarction, transplantation, and cerebral vasospasm. Other disorders associated with inflammatory cell activation and amenable to treatment according to the methods of the invention include rheumatoid arthritis, osteoarthritis, gouty arthritis, spondylitis; Behcet disease; sepsis, septic shock, endotoxic shock, gram negative sepsis, gram positive sepsis, toxic shock syndrome; multiple organ injury syndrome secondary to septicemia, trauma, or hemorrhage; allergic conjunctivitis, vernal conjunctivitis, uveitis, thyroid-associated ophthalmopathy; eosinophilic granuloma; asthma, chronic bronchitis, allergic rhinitis, ARDS, chronic obstructive pulmonary disease, silicosis, pulmonary sarcoidosis, pleurisy, alveolitis, vasculitis, pneumonia, bronchiectasis, pulmonary oxygen toxicity; reperfusion injury of the myocardium, brain, or extremities; cystic fibrosis; keloid formation, scar tissue formation; atherosclerosis; systemic lupus erythematosus, autoimmune thyroiditis, multiple sclerosis; Reynaud's syndrome; graft versus host disease, allograft rejection; chronic glomerulonephritis; inflammatory bowel disease, Crohn's disease, ulcerative colitis, necrotizing enterocolitis; inflammatory dermatoses, contact dermatitis, atopic dermatitis, psoriasis, urticaria, fever and myalgias due to infection; meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion associated syndromes; and cytokine-induced toxicity.

The invention, in still another aspect, is a method of inhibiting poly(ADP-ribose) polymerase activity in a cell, comprising contacting said cell with an hPARP2 antagonist in an amount effective for inhibiting expression or activity of the hPARP2 polypeptide.

These and other features and advantages of the present invention will be appreciated from the detailed description and examples that are set forth herein. The detailed description and examples are provided to enhance the understanding of the invention, but are not intended to limit the scope of the invention.

DETAILED DESCRIPTION OF THE PREFERRED EMBODIMENTS

The present invention relates generally to a previously uncharacterized nucleic acid encoding a novel human protein designated "human poly(ADP-ribose) polymerase 2" (hereinafter "hPARP2"). As illustrated herein hPARP2 is distinct from known proteins sharing a poly(ADP-ribose) polymerase activity. The present invention is based on the discovery of novel gene that encodes the hPARP2 protein, and nucleic acid sequences, oligonucleotides, fragments, and antisense molecules thereof.

The nucleotide sequence information provided by the invention makes possible large-scale expression of the encoded hPARP2 polypeptide by techniques well known and routinely practiced in the art. The invention also permits identification and isolation of polynucleotides encoding related hPARP2 polypeptides by well-known techniques including Southern (DNA) and/or northern (mRNA) hybridization, and amplification techniques such as polymerase chain reaction (PCR), ligase chain reaction (LCR), and the like. Examples of related polynucleotides include human and non-human parp2 genomic sequences, including allelic variants, as well as polynucleotides encoding polypeptides homologous to hPARP2 and structurally related polypeptides sharing one or more biological, immunological, and/or physical properties of hPARP2.

The invention includes both naturally-occurring and non-naturally occurring hPARP2 polynucleotides and polypeptide products thereof. Naturally-occurring hPARP2 products include distinct polynucleotide and polypeptide hPARP2 species as they occur in humans. However, the invention includes other human hPARP2 species defined through the analysis of sequence homology. The invention further comprises corresponding homologs of human hPARP2 that are expressed in cells of other animal species, preferably mammalian homologs, and more preferably primate homologs. Within each hPARP2 species, the invention further provides splice variants, which are encoded by the same genomic DNA but arise from distinct mRNA transcripts. Non-naturally occurring hPARP2 products include variants of the naturally occurring hPARP2 products such as polynucleotide and polypeptide analogs (i.e., wherein one or more nucleotides or amino acids are added, substituted, or deleted). Non-naturally-occurring hPARP2 products also include hPARP2 products that have been covalently modified, e.g., water-soluble polymer modifications, glycosylation variants, and the like.

The hPARP polypeptides and the nucleic acids that encode the polypeptides provide a basis for diagnostic methods for the precise and accurate detection and/or quantitation of hPARP2 expression and medical conditions associated with excessive or insufficient hPARP2 activity. Furthermore, the nucleotide sequences disclosed herein may be used in the detection of aberrations, such as mutations and deletions, in the gene encoding hPARP2. For example, the nucleotide sequences disclosed herein may be used to identify and isolate a genomic sequence for hparp2. PCR primers can be designed from various portions of the introns and exons of a genomic hparp2 nucleic acid sequence that will allow detection of aberrations in the genomic sequence.

The invention further provides methods of using hPARP2 and genetically engineered host cells that express recombinant hPARP2 to evaluate and screen for modulators of the poly(ADP-ribose) polymerase activity of the enzyme. Such screening methods may be used for the identification of allosteric agonists and antagonists of hPARP2 activity as well as for the identification of direct (e.g., competitive inhibitors) of such activity. hPARP2 protein antagonists and inhibitors, such as anti-hPARP2 antibodies and hparp2 antisense molecules, will provide the basis for pharmaceutical compositions for the treatment and amelioration of symptoms associated with excessive poly(ADP-ribose) polymerase activity. Agonists of hPARP2 will provide the basis of the treatment and amelioration of symptoms associated with insufficient poly(ADP-ribose) polymerase activity.

hparp2 Polynucleotides

The present invention provides, inter alia, novel purified and isolated polynucleotides encoding human hPARP2 polypeptides. The polynucleotides of the invention include DNA sequences and RNA transcripts, both sense and complementary antisense strands, and splice variants thereof. DNA sequences of the invention include, without limitation, cDNA and genomic sequences. As used herein, lower case "hparp2" refers to a nucleic acid sequence whereas upper case "hPARP2" refers to an amino acid sequence.

"Nucleic acid" as used herein refers to an oligonucleotide or polynucleotide sequence, and fragments or portions thereof, and to DNA or RNA of genomic or synthetic origin, which may be double-stranded or single-stranded, whether representing the sense or antisense strand. An exemplary double-stranded polynucleotide according to the invention can have a first strand (i.e., a coding strand) having a sequence encoding an hPARP2 polypeptide, along with a second strand (i.e., a "complementary" or "non-coding" strand) having a sequence deducible from the first strand according to the Watson-Crick base-pairing rules for DNA. Double-stranded or "duplex" structures may be DNA:DNA, DNA:RNA, or RNA:RNA nucleic acids. A preferred double-stranded polynucleotide is a cDNA having a nucleotide sequence defined by SEQ ID NO:1. An exemplary single-stranded polynucleotide according to the invention is a messenger RNA (mRNA) encoding an hPARP2 polypeptide. Another exemplary single-stranded polynucleotide is an oligonucleotide probe or primer that hybridizes to the coding or non-coding strand of a polynucleotide defined by SEQ ID NO:1. Other alternative nucleic acid structures, e.g., triplex structures, are also contemplated.

Genomic DNA of the invention comprises the protein-coding region for an hPARP2 polypeptide and includes allelic variants of the preferred polynucleotides of the invention, such as single nucleotide polymorphisms. Genomic DNA of the invention is distinguishable from genomic DNAs encoding polypeptides other than hPARP2 in that it includes the hPARP2-coding region found in hparp2 cDNA of the invention. Genomic DNA can be transcribed into RNA, and the resulting RNA transcript may undergo one or more splicing events wherein one or more introns (i.e., non-coding regions) of the transcript are removed, or "spliced out." RNA transcripts that can be spliced by alternative mechanisms and therefore be subjected to removal of different non-coding RNA sequences but still encode an hPARP2 polypeptide, are referred to in the art as "splice variants," and are embraced by the invention. Splice variants comprehended by the invention, therefore, are encoded by the same DNA sequences but give rise to different amino acid sequences. Such splice variants can comprise regions in which the reading frame is shifted, wherein a downstream portion of the RNA sequence is translated differently, to yield different amino acid sequences in the resulting polypeptides. Allelic variants are known in the art to be modified forms of the wild-type (predominant) gene sequence. Such modifications result from recombination during chromosomal segregation or exposure to conditions that give rise to genetic mutation. Allelic variants, like wild-type genes, are naturally occurring sequences, as opposed to non-naturally occurring variants, which arise from in vitro manipulation.

The invention also comprehends cDNA, which is obtained through reverse transcription of an RNA polynucleotide encoding hPARP2 followed by second strand synthesis of a complementary strand to provide a double stranded DNA. For example, the invention provides a cDNA sequence that encodes a polypeptide having the amino acid sequence defined by SEQ ID NO:2. In a preferred embodiment, the invention provides polynucleotides comprising a nucleotide sequence defined by SEQ ID NO:1.

In another aspect, the invention provides, inter alia, polynucleotides that encode polypeptides comprising amino acids 49–583, and preferably amino acids 1–583, of the amino acid sequence defined by SEQ ID NO:2. Alternatively, the invention provides polynucleotides that encode polypeptides comprising amino acids 1–49 of the amino acid sequence defined SEQ ID NO:2. Exemplary polynucleotides relating to this aspect of the invention include polynucleotides comprising at least nucleotides 209–1811, and preferably nucleotides 63–1811, of the nucleotide sequence defined by SEQ ID NO: 1. Alternative exemplary polynucleotides comprise nucleotides 1–209 or 63–209 of the nucleotide sequence defined by SEQ ID NO:1. Preferably, the polynucleotides encode an hPARP2 polypeptide or fragments thereof having hPARP2 catalytic activity.

As noted, highly preferred nucleic acid sequence according to the invention is defined by SEQ ID NO:1. However, because the genetic code is redundant or "degenerate" in its information-encoding properties, different nucleotide sequences may encode the same polypeptide sequence. Accordingly, the invention comprises the alternative (degenerate) nucleotide sequences that encode hPARP2 polypeptides of the invention and functional equivalents thereof. For example, the invention includes polynucleotides comprising nucleotide sequences that are substantially homologous to the hparp2 sequence of SEQ ID NO:1. More particularly, the invention includes polynucleotides whose corresponding nucleotide sequences have at least 90%, preferably at least 95%, more preferably at least 98%, and still more preferably at least 99% identity with a nucleotide sequence defined in SEQ ID NO:1.

Variant polynucleotides of the invention further include fragments of the nucleotide sequence defined in SEQ ID NO:1 and homologs thereof. The disclosure of full-length polynucleotides encoding hPARP2 polypeptides makes readily available to the person having ordinary skill in the art every possible fragment of the full-length polynucleotides. Preferably, fragment polynucleotides of the invention comprise sequences unique to the hPARP2-coding nucleotide sequence, and therefore hybridize under highly stringent or moderately stringent conditions only (i.e., specifically) to polynucleotides encoding hPARP2 or fragments thereof containing the unique sequence. Polynucleotide fragments of genomic sequences of the invention comprise not only sequences unique to the coding region, but also include fragments of the full-length sequence derived from introns, regulatory regions, and/or other untranslated sequences. Sequences unique to polynucleotides of the invention are recognizable through sequence comparison to other known polynucleotides, and can be identified through use of computer software routinely used in the art, e.g., alignment programs available in public sequence databases.

The invention also provides fragment polynucleotides that are conserved in one or more polynucleotides encoding members of the hPARP2 family of polypeptides. Such fragments include sequences characteristic of the family of hPARP2 polypeptides, referred to as "signature" sequences. The conserved signature sequences are readily discernable following simple sequence comparison of polynucleotides encoding members of the hPARP2 family. Polynucleotide fragments of the invention can be labeled in a manner that permits their detection, including radioactive and non-radioactive labeling.

Hybridization can be defined to include the process of forming partially or completely double-stranded nucleic acid molecules through sequence-specific association of complementary single-stranded nucleic molecules. The invention, therefore, further encompasses the use of nucleic acid species that hybridize to the coding or non-coding strands of a polynucleotide that encodes an hPARP2 protein. Preferred hybridizing species hybridize to the coding or non-coding strand of the nucleotide sequence defined by SEQ ID NO:1. Also encompassed are species that would hybridize to an hPARP2-encoding polynucleotide but for the redundancy of the genetic code, i.e., polynucleotides that encode the same amino acid sequence but rely on different codon usage.

Hybridizing species include, for example, nucleic acid hybridization or amplification probes (oligonucleotides) that are capable of detecting nucleotide sequences (e.g., genomic sequences) encoding hPARP2 or closely related molecules, such as alleles. The specificity of the probe, i.e., whether it is derived from a highly conserved, conserved, or non-conserved region or domain, and the stringency of the hybridization or amplification conditions (high, intermediate, or low) will determine whether the probe identifies only naturally occurring hparp2, or related sequences. Probes for the detection of related nucleotide sequences are selected from conserved or highly conserved regions of hparp2 family members and such probes may be used in a pool of degenerate probes. For the detection of identical nucleotide sequences, or where maximum specificity is desired, oligonucleotide probes are selected from the non-conserved nucleotide regions or unique regions of hparp2 polynucleotides. As used herein, the term "non-conserved nucleotide region" refers to a nucleotide region that is unique to hparp2 disclosed herein and does not occur in related hparp2 family members.

Specificity of hybridization is typically characterized in terms of the degree of stringency of the conditions under which the hybridization is performed. The degree of stringency of hybridization conditions can refer to the melting temperature ($T_m$) of the nucleic acid binding complex [see, e.g., Berger and Kimmel, "Guide to Molecular Cloning Techniques," *Methods in Enzymology*, Vol. 152, Academic Press, San Diego Calif. (1987)]. "Maximal stringency" typically occurs at about $T_m$–5° C. (5° C. below the $T_m$ of the probe); "high stringency" at about 5° C. to 10° C. below $T_m$; "intermediate stringency" at about 10° C. to 20° C. below $T_m$; and "low stringency" at about 20° C. to 25° C. below $T_m$.

Alternatively, the stringency of hybridization can refer to the physicochemical conditions employed in the procedure. To illustrate, exemplary moderately stringent hybridization conditions are: hybridization in 3× saline sodium citrate (SSC), 0.1% sarkosyl, and 20 mM sodium phosphate, pH 6.8, at 65° C.; and washing in 2×SSC with 0.1% sodium dodecyl sulfate (SDS), at 65° C. Exemplary highly stringent hybridization conditions are: hybridization in 50% formamide, 5×SSC, at 42° C. overnight, and washing in 0.5×SSC and 0.1% SDS, at 50° C. It is understood in the art that conditions of equivalent stringency can be achieved through variation of temperature and buffer, or salt concentration [see Ausubel et al. (Eds.), *Current Protocols in Molecular Biology*, John Wiley & Sons (1994), at pp. 6.0.3–6.4.10]. Modifications in hybridization conditions can be determined empirically or calculated precisely based on the length-of the oligonucleotide probe and the percentage of guanosine/cytosine (GC) base pairing of the probe. The hybridization conditions can be calculated as described in Sambrook et al., (Eds.), *Molecular Cloning: A Laboratory Manual*, Cold Spring Harbor Laboratory Press: Cold Spring Harbor, N.Y. (1989), at pp. 9.47–9.51.

The artisan will appreciate that hybridization under more stringent conditions enables the identification of species having a higher degree of homology or sequence identity with the target sequence. By contrast, hybridization under less stringent conditions enables identification of species having a lesser but still significant degree of homology or sequence identity with the target sequence. Therefore, also included within the scope of the present invention are nucleic acid species that are capable of hybridizing to the nucleotide sequence of SEQ ID NO:1 under conditions of intermediate (moderate) to maximal stringency. Preferably, the hybridizing species hybridize to the coding or non-coding strands of a polynucleotide defined by SEQ ID NO:1 under highly stringent conditions. Preferred polynucleotides include, inter alia, species that hybridize to a nucleic acid sequence consisting of nucleotides 1 to 209 as defined by SEQ ID NO:1 or the complement of that region under conditions of moderate stringency, and more preferably that do so under conditions of high stringency. Other preferred polynucleotides are species that hybridize to a nucleic acid sequence consisting of nucleotides 63 to 209 as defined by SEQ ID NO:1 or the complement of that region under conditions of moderate stringency, and more preferably that do so under conditions of high stringency.

The polynucleotides of the invention encompass oligonucleotides (i.e., nucleic acid oligomers typically about 10 to 60 nucleotides in length) that hybridize to either the coding or the non-coding strands of a nucleic acid encoding an hPARP2 amino acid sequence. In particular, the invention comprises oligonucleotides that hybridize to the coding or non-coding strand of a polynucleotide defined by SEQ ID NO:1. The length of the oligonucleotide is not critical, as long as it is capable of hybridizing to the target nucleic acid molecule. However, longer nucleic acid molecules are more difficult to prepare and require longer hybridization times. Therefore, the oligonucleotide should not be longer than necessary. Accordingly, the oligonucleotide should contain at least 10 nucleotides, preferably at least 15 nucleotides, and more preferably at least 20 nucleotides. Normally, the oligonucleotide will not contain more than 60 nucleotides, preferably not more than 30 nucleotides, and more preferably not more than 25 nucleotides. Such oligonucleotides may be used as described herein as primers for DNA synthesis (e.g., as primers in PCR; "amplimers"), as probes for detecting the presence of target DNA in a sample (e.g., northern or Southern blots and in situ hybridization), as therapeutic agents (e.g., in antisense therapy), or for other purposes. Oligonucleotides may be single- or double-stranded, with the double-stranded forms having one or both ends blunt or stepped.

The oligonucleotides may be obtained or derived by known methods from natural sources. Alternatively, the oligonucleotides may be produced synthetically according to methods known in the art. Such methods include, for example, cloning and restriction of appropriate sequences or direct chemical synthesis by any suitable method. Various chemical methods for making oligonucleotides are known in the art, including the phosphotriester method, the phosphodiester method; the diethylphosphoramidite method; the solid support method, and the H-phosphonate method [for reviews, see Caruthers, *Science* 230:281–5 (1985); Caruthers et al., *Methods Enzymol* 211:3–20 (1992)]. Typically, preparation of oligonucleotides is carried out by automated phosphoramidite synthesis on polymer support. Nucleic acid molecules consisting of 100 or more nucleotides may also be produced by such methods.

The hparp2 polynucleotides of the invention include variants, which are polynucleotides that encode hPARP2 or a functional equivalent thereof, and which can include deletions, insertions, or substitutions of nucleotide residues. As used herein a "deletion" is a change in a nucleotide or amino acid sequence in which one or more nucleotides or amino acid residues, respectively, are absent. As used herein an "insertion" or "addition" is a change in a nucleotide or amino acid sequence that results in the addition of one or more nucleotides or amino acid residues, respectively. As used herein a "substitution" is a change in a nucleotide or amino acid sequence in which one or more nucleotides or amino acids are replaced by different nucleotides or amino acids, respectively.

Polynucleotide variants also included within the scope of the present invention are alleles or alternative naturally occurring forms of hparp2. Alleles result from naturally occurring mutations, i.e., deletions, insertions or substitutions, in the genomic nucleotide sequence, which may or may not alter the structure or function or the expressed polypeptides. Each of these types of mutational changes may occur alone, or in combination with the others, one or more times in a given allelic sequence. Single nucleotide polymorphisms (SNPs) may occur, in which a single base mutation may define an altered polypeptide, which in turn may be associated with an overt phenotypic difference. Of course, SNPs may be silent, as they may not change the encoded polypeptide, or any change they do encode may have no effect on phenotype.

The invention further embraces natural homologs of the human parp2 DNA that occur in other animal species, preferably other mammal species, and more preferably other primate species. Such species homologs, in general, share significant homology at the nucleotide level within the protein-coding regions. Thus, the invention encompasses polynucleotides that share at least 75%, at least.80%, at least 85%, at least 90%, at least 95%, at least 98%, or at least 99% nucleotide identity with the protein-coding region of a polynucleotide encoding a human hPARP2 polypeptide, e.g., the polynucleotide defined by SEQ ID NO:1. Percent sequence "homology" with respect to polynucleotides of the invention can be defined as the percentage of nucleotide bases in a candidate sequence that are identical to nucleotides in the hPARP2-encoding sequence after aligning the sequences and introducing gaps, if necessary, to achieve maximum percent sequence identity. Computer software is available (from commercial and public domain sources) for calculating percent identity in an automated fashion (e.g., FASTA).

The invention includes polynucleotides that have been engineered to selectively modify the cloning, processing, and/or expression of the hPARP2 gene product. Mutations may be introduced using techniques well known in the art, e.g., site-directed mutagenesis to insert new restriction sites, to alter glycosylation patterns, or to change codon preferences inherent in the use of certain expression systems, while simultaneously maintaining control of the amino acid sequence of the expressed polypeptide product. For example, codons preferred by a particular prokaryotic or eukaryotic host cell can be selected to increase the rate of hPARP2 expression or to produce recombinant RNA transcripts having desirable properties, such as longer half-lives.

The hparp2 polynucleotides can be synthesized, wholly or partly, using chemical methods well known in the art. "Chemically synthesized," as used herein and is understood in the art, refers to purely chemical, as opposed to enzymatic, methods for producing polynucleotides. "Wholly" chemically synthesized DNA sequences are therefore produced entirely by chemical means; "partly" chemically synthesized DNAs embrace those wherein only portions of the resulting DNA were produced by chemical means.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiester linkages within the backbone of the molecule.

The invention also provides hPARP2 peptide nucleic acid (PNA) molecules. These hPARP2 PNAs are informational molecules that have a neutral "peptide-like" backbone with nucleobases that allow the molecules to hybridize to complementary hPARP2-encoding DNA or RNA with higher affinity and specificity than corresponding oligonucleotides (PerSeptive Biosystems).

Polypeptide Expression Systems

Knowledge of hPARP2-encoding DNA sequences enables the artisan to modify cells to permit or increase expression of hPARP2. Accordingly, host cells are provided, including prokaryotic or eukaryotic cells, either stably or transiently modified by introduction of a polynucleotide of the invention to permit expression of the encoded hPARP2 polypeptide. Autonomously replicating recombinant expression constructs such as plasmid and viral DNA vectors incorporating hPARP2-encoding sequences are also provided.

Expression constructs are also provided comprising hPARP2-encoding polynucleotides operatively linked to an endogenous or exogenous expression control DNA sequence and a transcription terminator. Expression control DNA sequences include promoters, enhancers, and operators, and are generally selected based on the expression systems in which the expression construct is to be used. Preferred promoter and enhancer sequences are generally selected for the ability to increase gene expression, while operator sequences are generally selected for the ability to regulate gene expression. Preferred constructs of the invention also include sequences necessary for replication in a host cell. Expression constructs are preferably used for production of an encoded hPARP2 polypeptide, but may also be used to amplify the construct itself.

Polynucleotides of the invention may be introduced into the host cell as part of a circular plasmid, or as linear DNA comprising an isolated protein coding region or a viral vector. Methods for introducing DNA in to a host cell include transformation, transfection, electroporation, nuclear injection, or fusion with carriers such as liposomes, micelles, ghost cells, and protoplasts. Expression systems of the invention include, for example, bacteria, yeast, fungal, plant, insect, invertebrate, amphibian, and mammalian cell systems. Some suitable prokaryotic host cells include, for example, *E. coli* strains SG-936, HB 101, W3110, X1776, X2282, DHI, and MRC1, Pseudomonas species, Bacillus species such as *B. subtilis*, and Streptomyces species. Suitable eukaryotic host cells include yeasts, such as *Saccharomyces cerevisiae, S. pombe, Pichia pastoris* and other fungi, insect cells such as sf9 or sf21 cells (*Spodoptera frugiperda*), animal cells such as Chinese hamster ovary (CHO) cells, human cells such as JY, 293, and NIH3T3 cells, and plant cells such as *Arabidopsis thaliana* cells. The hparp2 nucleotide sequence, or any portion of it, may be cloned into a vector for the production of an mRNA probe. Such vectors are known in the art, are commercially available, and may be used to synthesize RNA probes in vitro by addition of labeled nucleotides and an appropriate RNA polymerase such as T7, T3, or SP6.

The type of host cell, the form of the expressed hPARP2 product, the conditions of growth, etc., can be selected by the skilled artisan according to known criteria. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms of hPARP2 polypeptides are embraced. The protein produced by a recombinant cell may be secreted or may be contained intracellularly, depending on the sequence and/or the vector used. As will be understood by those of skill in the art, expression vectors containing hparp2 can be designed with signal sequences that direct secretion of hPARP2 through a particular prokaryotic or eukaryotic cell membrane.

Expression constructs may include sequences that facilitate, and preferably promote, homologous recombination in a host cell. This can be accomplished by replacing all or part of the naturally occurring hparp2 promoter with all or part of a heterologous promoter so that the cells express hPARP2 at higher levels. The heterologous promoter should be inserted so that it is operatively linked to hPARP2-encoding sequences [see, for example, PCT International Publication Nos. WO 94/12650, WO 92/20808, and WO 91/09955].

Host cells of the invention are useful in methods for large-scale production of hPARP2 polypeptide products. For example, host cells of the invention are a valuable source of immunogen for development of antibodies that are immunoreactive with hPARP2 polypeptides. As another example, recombinant hPARP2 can be produced and isolate from host cells for use in in vitro binding assays such as drug screening assays. In such methods, the host cells are grown in a suitable culture medium and the desired polypeptide product is isolated from the cells or from the medium in which the cells are grown.

The polypeptide product can be isolated by purification methods known in the art, such as conventional chromatographic methods including immunoaffinity chromatography, receptor affinity chromatography, hydrophobic interaction chromatography, lectin affinity chromatography, size exclusion filtration, cation or anion exchange chromatography, high performance liquid chromatography (HPLC), reverse phase HPLC, and the like.

Still other methods of purification include those in which the desired protein is expressed and purified as a fusion protein in which the hPARP2 polypeptide is ligated to a heterologous amino acid sequence. Suitable heterologous sequences can include a specific tag, label, or chelating moiety that is recognized by a specific binding partner or agent. For example, for screening of peptide libraries for modulators of hPARP2 activity, it is possible to express an hPARP2 protein fused to a selected heterologous protein selected to be specifically identifiable using a probe antibody. A fusion protein may also be engineered to contain a cleavage site (e.g., a factor XA or enterokinase sensitive sequence) located between the hPARP2 sequence and the heterologous protein sequence, to permit the hPARP2 protein to be cleaved from the heterologous protein and subsequently purified. Cleavage of the fusion component may produce a form of the desired protein having additional amino acid residues resulting from the cleavage process.

Exemplary heterologous peptide domains include metal-chelating peptides such as histidine-tryptophan modules that allow purification on immobilized metals [Porath, *Protein Expr Purif* 3:263–81 (1992)], and protein A domains that allow purification on immobilized immunoglobulin. Another useful system is the divalent cation-binding domain and antibodies specific thereto used in the peptide extension/immunoaffinity purification system described in U.S. Pat. Nos. 4,703,004; 4,782,137; 4,851,431; and 5,011,912. This system is commercially available as the FLAG® system from Immunex Corp. (Seattle, Wash.). Another suitable heterologous fusion partner is glutathione S-transferase (GST), which can be affinity purified using immobilized glutathione. Other useful fusion partners include immunoglobulins and fragments thereof, e.g., Fc fragments.

Identification of host cells expressing recombinant hPARP2 may be crucial to identifying appropriate expression systems. Accordingly, expression constructs of the invention may also include sequences encoding one or more selectable markers that permit identification of host cells bearing the construct in operative condition. It is also contemplated that, in addition to the insertion of heterologous promoter DNA, amplifiable marker DNA (e.g., ada, dhfr, and the multifunctional CAD gene that encodes carbamyl phosphate synthase, aspartate transcarbamylase, and dihydroorotase) and/or intron DNA may be inserted along with the heterologous promoter DNA. If linked to the hPARP2-encoding sequence, amplification of the marker DNA by standard selection methods results in co-amplification of the hPARP2-encoding sequences in the cells. Detection of expression of the marker gene in response to induction or selection usually indicates expression of hPARP2 as well. Alternatively, if the hparp2 polynucleotide is inserted within a marker gene sequence, recombinant cells containing hparp2 can be identified by the absence of marker gene function.

Host cells that contain the coding sequence for hPARP2 and express hPARP2 may be identified by a variety of other procedures known to those of skill in the art. These procedures include, but are not limited to, DNA-DNA or DNA-RNA hybridization and protein bioassay or immunoassay techniques that include membrane-based, solution-based, or chip-based technologies for the detection and/or quantification of the nucleic acid or protein.

The presence of the hparp2 polynucleotide sequence can be detected by DNA-DNA or DNA-RNA hybridization or amplification using fragments of hparp2 disclosed in SEQ ID NO:1 as probes. Nucleic acid amplification based assays involve the use of oligonucleotides based on the hparp2 sequence to detect transformants containing hparp2 DNA or RNA. Labeled hybridization or PCR probes for detecting hparp2 polynucleotide sequences can be made by various methods, including oligolabeling, nick translation, end-labeling, or PCR amplification using a labeled nucleotide.

In an embodiment of the present invention, hPARP2 or a variant thereof and/or a host cell line that expresses the hPARP2 or variant thereof may be used to screen for antibodies, peptides, or other molecules, such as organic or inorganic molecules, that act as modulators of a biological or immunological activity of hPARP2. For example, anti-hPARP2 antibodies capable of neutralizing the polymerase or DNA-binding activity of hPARP2 may be used to inhibit hPARP2-mediated cell death. Alternatively, screening of peptide libraries or organic libraries made by combinatorial chemistry with recombinantly expressed hPARP2 or variants thereof or cell lines expressing hPARP2 or variants thereof may be useful for identification of therapeutic molecules that function by modulating a biological or immunological activity of hPARP2. Synthetic compounds, natural products, and other sources of potentially biologically active materials can be screened in a number of ways deemed routine by those of skill in the art. For example, nucleotide sequences encoding the DNA-binding domain of hPARP2 may be expressed in a host cell, which can be used for screening of allosteric modulators, either agonists or antagonists, of hPARP2 activity. Alternatively, nucleotide sequences encoding the conserved catalytic domain of hPARP2 can be expressed in host cells and used to screen for inhibitors of ADP-ribose polymerization.

hPARP2 Polypeptides

The invention also provides purified and isolated mammalian hPARP2 polypeptides. An exemplary hPARP2 polypeptide has an amino acid sequence defined in SEQ ID NO:2. hPARP2 polypeptides of the invention may be isolated from natural cell sources or may be chemically synthesized, but are preferably produced by recombinant procedures involving host cells of the invention. hPARP2 products of the invention may be full-length polypeptides, or variant polypeptide products such as fragments, truncates, deletion mutants, and other variants thereof that retain specific hPARP2 biological activity. As used herein, "biologically active" refers to an hPARP2 polypeptide having structural, regulatory or biochemical functions of the naturally occurring hPARP2 protein. Specifically, an hPARP2 protein of the present invention has the ability to bind DNA and to polymerize ADP-ribose subunits in response to DNA damage in a cell.

The protein and fragments of the present invention may be prepared by methods known in the art. Such methods include isolating the protein directly from cells, isolating or synthesizing DNA encoding the protein and using the DNA to produce recombinant protein, and synthesizing the protein chemically from individual amino acids.

The hPARP2 polypeptides can be isolated from a biological sample, such as a solubilized cell fraction, by standard methods. Some suitable methods include precipitation and liquid chromatographic protocols such as ion exchange, hydrophobic interaction, and gel filtration [see, e.g., Deutscher (Ed.), *Methods Enzymol* (*Guide to Protein Chemistry*, Section VII) 182:309 (1990); Scopes, *Protein Purification*, Springer-Verlag, New York (1987)]. Alternatively, purified material is obtained by separating the protein on preparative SDS-PAGE gels, slicing out the band of interest and electroeluting the protein from the polyacrylamide matrix by methods known in the art. The detergent SDS is removed from the protein by known methods, such as by dialysis or the use of a suitable column, such as the Extracti-Gel® column (Pierce).

The hPARP2 polypeptide of the invention may also be chemically synthesized, wholly or partly, by methods known in the art. Suitable methods for synthesizing the protein are described in the art [e.g., Stuart and Young, Solid Phase Peptide Synthesis, 2d ed., Pierce Chemical Co. (1984)]. For example, peptides can be synthesized by solid phase techniques, cleaved from the resin, and purified by preparative high performance liquid chromatography (HPLC) [see, e.g., Roberge et al., *Science* 269:202–4 (1995)]. Automated synthesis may be accomplished, for example, using the ABI 431A Peptide Synthesizer (Perkin Elmer, Norwalk, Conn.) in accordance with the instructions provided by the manufacturer. The composition of the synthetic peptides may be confirmed by amino acid analysis or sequencing (e.g., the Edman degradation procedure).

As described in greater detail above, recombinant hPARP2 protein may be produced in and isolated from a host cell transformed with an expression vector containing an hparp2 nucleotide sequence and grown in cell culture. As described herein, the host cells, either prokaryotic or eukaryotic, are either stably or transiently transfected (eukaryotic) or transformed (prokaryotic) with an hPARP2-encoding polynucleotide of the invention in a manner that permits directed expression of an hPARP2 polypeptide. In such methods, the host cells are grown in a suitable culture medium and the desired polypeptide products are isolated from the cells or from the medium in which the cells are grown. Isolation of the polypeptides can be accomplished by, for example, immunoaffinity purification. The use of transformed host cells is preferred for large-scale production of hPARP2 polypeptides.

The invention includes polypeptides comprising amino acid sequences that are substantially homologous to the sequences of hPARP2 polypeptides described herein. For example, the invention includes polypeptides whose corresponding amino acid sequences have at least 90%, preferably at least 95%, more preferably at least 98%, and still more preferably at least 99% identity with the polypeptide sequence defined in SEQ ID NO:2.

Percent sequence "identity" with respect to a preferred polypeptide of the invention can be defined as the percentage of amino acid residues in a candidate sequence that are identical to amino acid residues in the reference hPARP2 sequence after aligning the sequences and introducing gaps, if necessary, to achieve maximum percent sequence identity, and not considering any conservative substitutions as part of the sequence identity.

Percent sequence "homology" with respect to a preferred polypeptide of the invention can be defined as the percentage of amino acid residues in a candidate sequence that are identical to amino acid residues in the reference hPARP2 sequence after aligning the sequences and introducing gaps, if necessary, to achieve maximum percent sequence identity, and also considering any conservative substitutions as part of the sequence identity.

Determinations of whether two amino acid sequences are substantially homologous can also be based on FASTA searches [Pearson et al., *Proc Natl Acad Sci USA* 85:2444–8 (1988)]. Alternatively, percent homology is calculated as the percentage of amino acid residues in the smaller of the two sequences that align with identical amino acid residues in the sequence being compared, when four gaps in a length of 100 amino acids may be introduced to maximize alignment. See Dayhoff, in *Atlas of Protein Sequence and Structure*, Vol. 5, National Biochemical Research Foundation, Washington, D.C. (1972), at p. 124.

A polypeptide may be considered homologous to an hPARP2 polypeptide of the invention if polynucleotides encoding the two polypeptides hybridize with one another. A higher degree of homology is shown if the hybridization occurs under hybridization conditions of greater stringency. Control of hybridization conditions and the relationships between hybridization conditions and degree of homology are understood by those skilled in the art. See, e.g., Sambrook et al. (1989). Thus, a homologous polypeptide may be a polypeptide that is encoded by a polynucleotide that hybridizes with a polynucleotide encoding a polypeptide of the invention under hybridization conditions having a specified degree of stringency.

It may be desirable that such structurally homologous polypeptides will also exhibit functional homology, insofar as the homologous polypeptide has substantially the same function as the polypeptide of the invention. For example, structurally homologous polypeptides may be considered functionally homologous if they exhibit similar binding of a ligand, or similar immune reactivity, etc.

However, it is known that two polypeptides or two polynucleotides may be considered to be substantially homologous in structure, and yet differ substantially in function. For example, single nucleotide polymorphisms (SNPs) among alleles may be expressed as polypeptides having substantial differences in function along one or more measurable parameters such as antibody- or ligand-binding affinity or enzymatic substrate specificity, and the like. Other structural differences, such as substitutions, deletions, splicing variants, and the like, may affect the function of otherwise structurally identical or homologous polypeptides.

The hPARP2 polypeptides of the invention include functional derivatives of the hPARP2 polypeptide defined in SEQ ID NO:2. Such functional derivatives include polypeptide products that possess a structural feature or a biological activity that is substantially similar to a structural feature or a biological activity of the hPARP2 protein. Accordingly, functional derivatives include variants, fragments, and chemical derivatives of the parent hPARP2 protein.

As used herein "variant" refers to a molecule substantially similar in structure and function to either the entire hPARP2 molecule, or to a fragment thereof A molecule is said to be "substantially similar" to another if both molecules have substantially similar structures or if both molecules possess a similar biological activity. Thus, provided that two molecules possess a similar activity, they are considered variants, as that term is used herein, even if one of the molecules possesses a structure not found in the other molecule, or if the sequence of amino acid residues is not identical.

Among the variant polypeptides provided under the invention are variants that comprise one or more changes in the amino acid sequence of the hPARP2 polypeptide. Such sequence-based changes include deletions, substitutions, or insertions in the hPARP2 sequence, as well as combinations thereof.

Deletion variants of the hPARP2 polypeptides are polypeptides in which at least one amino acid residue of the sequence is removed. Deletions can be effected at one or both termini of the protein, or with removal of one or more residues within the hPARP2 amino acid sequence. Deletion variants include, for example, all incomplete fragments of the hPARP2 polypeptides of the invention. As used herein "fragment" refers to any polypeptide subset of the hPARP2 protein. A preferred fragment is a purified and isolated hPARP2 polypeptide comprising amino acids 1–49 of the amino acid sequence defined in SEQ ID NO:2. Alternative preferred fragments include purified and isolated hPARP2 polypeptides comprising at least one amino acid residue from a region consisting of amino acids 1–49 of the amino acid sequence defined in SEQ ID NO:2. Such fragments include, for example, fragments comprising amino acids 49–583 of the amino acid sequence defined by SEQ ID NO:2, as well as N-terminally extended fragments of that sequence and C-terminal truncates thereof.

Fragments of hPARP2 that exhibit a biological activity characteristic of hPARP2 and that are soluble (i.e., not membrane bound) are desirable. A soluble fragment is preferably generated by deleting any membrane-spanning region(s) of the parent molecule or by deleting or substituting hydrophilic amino acid residues for hydrophobic residues. Identification of such residues is well known in the art.

Substitution variants are provided, including polypeptides in which at least one amino acid residue of an hPARP2 polypeptide is replaced by an alternative residue. Any substitution can be made, with conservative substitutions being preferred. Directed amino acid substitutions may be made based on well defined physicochemical parameters of the canonical and other amino acids (e.g., the size, shape, polarity, charge, hydrogen-bonding capacity, solubility, chemical reactivity, hydrophobicity, hydrophilicity, or the amphipathic character of the residues.) as well as their contribution to secondary and tertiary protein structure. Substitution variants can include polypeptides comprising one or more conservative amino acid substitutions, i.e., a substitution of one amino acid by another having similar physicochemical character as desired. To illustrate, the canonical amino acids can be grouped according to the following categories:

| | |
|---|---|
| Aliphatic Side Chains | Gly, Ala; Val, Leu, Ile |
| Aromatic Side Chains | Phe, Tyr, Trp |
| Aliphatic Hydroxyl Side Chains | Ser, Thr |
| Basic Side Chains | Lys, Arg, His |
| Acidic Side Chains | Asp, Glu |
| Amide Side Chains | Asn, Gln |
| Sulfur-Containing Side Chains | Cys, Met |
| Secondary Amino Group | Pro |

Substitutions are preferably made in accordance with the following Table 1 when it is desired to controllably define the characteristics of the hPARP2 molecule.

TABLE 1

| Original Residue | Exemplary Conservative Substitutions |
|---|---|
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in functional or immunological identity are made by selecting substitutions that are more progressive than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that are in general more progressive are those in which: (a) glycine and/or proline is substituted by another amino acid or is deleted or inserted; (b) a hydrophilic residue is substituted for a hydrophobic residue; (c) a cysteine residue is substituted for (or by) any other residue; (d) a residue having an electropositive side chain is substituted for (or by) a residue having an electronegative charge; or (e) a residue having a bulky side chain is substituted for (or by) one not having such a side chain. Most preferred are amino acid substitutions that affect the solubility of hPARP2. These are most preferably generated by substituting hydrophilic for hydrophobic amino acids.

Substitution variants, however, can include non-canonical or non-naturally occurring amino acid residues substituted for amino acid residues in the principal sequence. Substitution variants include those polypeptides in which amino acid substitutions have been introduced by modification of polynucleotides encoding an hPARP2 polypeptide.

Insertion variants are provided, in which at least one amino acid residue is present in addition to an hPARP2 amino acid sequence. Insertions may be located at either or both termini of the polypeptide, or may be positioned within the hPARP2 amino acid sequence. Insertional variants also include fusion proteins in which the amino or carboxy terminus of the hPARP2 polypeptide is fused to another polypeptide. Examples of such fusion proteins include immunogenic polypeptides, proteins with long circulating half-life (e.g., immunoglobulin constant regions), marker proteins (e.g., green fluorescent protein) and proteins or polypeptides that facilitate purification of the desired hPARP2 polypeptide (e.g., FLAG® tags or polyhistidine sequences). Another example of a terminal insertion is a fusion of a signal sequence, whether heterologous or homologous to the host cell, to the N-terminus of the molecule to facilitate the secretion of the derivative from recombinant hosts. Intrasequence insertions (i.e., insertions within an hPARP2 molecule sequence) may range generally from about 1 to 10 residues, more preferably 1 to 5.

Polypeptide variants of the invention also include mature hPARP2 products, i.e., hPARP2 products wherein leader or signal sequences are removed, as well as products having additional amino terminal residues. hPARP2 products having an additional methionine residue at position-1 ($Met^{-1}$-hPARP2) are contemplated, as are hPARP2 products having additional methionine and lysine residues at positions-2 and -1, respectively ($Met^{-2}$-$Lys^{-1}$-hPARP2). Other such variants are particularly useful for recombinant protein production in bacterial host cells.

The invention also encompasses hPARP2 variants having additional amino acid residues resulting from use of specific expression systems. For example, use of commercially available vectors that express a desired polypeptide as a glutathione-S-transferase (GST) fusion product yields the desired polypeptide having an additional glycine residue at position-1 ($Gly^{-1}$-hPARP2) upon cleavage of the GST component from the desired polypeptide. Variants that result from expression in other vector systems are also contemplated.

The invention further provides hPARP2 polypeptide products that are chemical derivatives of the hPARP2 polypeptide defined in SEQ ID NO:2. As used herein, the term "chemical derivative" refers to molecules that contain additional chemical moieties that are not normally a part of the naturally occurring molecule. Such moieties may impart desirable properties to the derivative molecule, such as increased solubility, absorption, biological half-life, etc. The moieties may alternatively decrease the toxicity of the derivative molecule, or eliminate or attenuate any undesirable side effect of the derivative molecule. Thus, chemical derivatives of hPARP2 polypeptides include polypeptides bearing modifications other than (or in addition to) insertion, deletion or substitution of amino acid residues. Preferably, the modifications are covalent in nature, and include, for example, chemical bonding with polymers, lipids, non-naturally occurring amino acids, and other organic and inorganic moieties. Derivatives of the invention may be prepared to increase circulating half-life of an hPARP2 polypeptide, or may be designed to improve targeting capacity for the polypeptide to desired cells, tissues, or organs.

For example, methods are known in the art for modifying a polypeptide to include one or more water-soluble polymer attachments such as polyethylene glycol, polyoxyethylene glycol, or polypropylene glycol. Particularly preferred are hPARP2 products that have been covalently modified with polyethylene glycol (PEG) subunits. Water-soluble polymers may be bonded at specific positions, for example at the amino terminus of the hPARP2 products, or randomly attached to one or more side chains of the polypeptide. Additional derivatives include hPARP2 species immobilized on a solid support, pin microparticle, or chromatographic resin, as well as hPARP2 species modified to include one or more detectable labels, tags, chelating agents, and the like.

Derivatization with bifunctional agents can be used to cross-link TANK2 to a water-insoluble support matrix. Alternatively, reactive water-insoluble matrices such as cyanogen bromide-activated carbohydrates and reactive substrates may be employed for protein immobilization [see, e.g., U.S. Pat. Nos. 3,969,287; 3,691,016; 4,195,128; 4,247, 642; 4,229,537; and 4,330,440.]

Expression of hPARP2 variants can be expected to have utility in investigating a biological activity characteristic of a wild-type hPARP2 polypeptide. hPARP2 variants can be designed to retain all biological or immunological properties characteristic for hPARP2, or to specifically disable one or more particular biological or immunological properties of hPARP2. For example, fragments and truncates may be designed to delete a domain associated with a particular property, or substitutions and deletions may be designed to inactivate a property associated with a particular domain. Forced expression (overexpression) of such variants ("dominant negative" mutants) can be employed to study the function of the protein in vivo by observing the phenotype associated with the mutant.

Functional derivatives of hPARP2 having up to about 100 residues may be conveniently prepared by in vitro synthesis. If desired, such fragments may be modified using methods known in the art by reacting targeted amino acid residues of the purified or crude protein with an organic derivatizing agent that is capable of reacting with selected side chains or terminal residues. The resulting covalent derivatives may be used to identify residues important for biological activity.

Functional derivatives of hPARP2 having altered amino acid sequences can also be prepared by mutating the DNA encoding hPARP2. Any combination of amino acid deletion, insertion, and substitution may be employed to generate the final construct, provided that the final construct possesses the desired activity. Obviously, the mutations that will be made in the DNA encoding the functional derivative must not place the sequence out of reading frame and preferably will not create complementary regions that could produce secondary mRNA structure [see EP Patent Publication No. 75,444].

While the site for introducing a variation in the amino acid sequence is predetermined, the mutation per se need not be predetermined. For example, to optimize the performance of a mutation at a given site, random mutagenesis, such as linker scanning mutagenesis, may be conducted at a target codon or target region to create a large number of derivative which could then be expressed and screened for the optimal combination of desired activity. Alternatively, site-directed mutagenesis or other well-known technique may be employed to make mutations at predetermined sites in a DNA known sequence.

The technique of site-directed mutagenesis is well known in the art [e.g., Sambrook et al., supra, and McPherson (Ed.), *Directed Mutagenesis: A Practical Approach*, IRL Press, Oxford (1991)]. Site-directed mutagenesis allows the production of hPARP2 functional derivatives through use of specific oligonucleotide sequences that encode the DNA sequence of the desired mutation. Site-directed mutagenesis methods and materials are commercially available, e.g., the QuikChange™ kit available from Stratagene (La Jolla, Calif.). One can selectively generate precise amino acid deletions, insertions, or substitutions using this method. Amino acid sequence deletions generally range from about 1 to 30 residues, more preferably 1 to 10 residues, and typically are contiguous. The most preferred deletions are those that are performed to generate catalytic fragments or DNA-binding fragments.

Mutations designed to increase the affinity of hPARP2 may be guided by the introduction of the amino acid residues that are present at homologous positions in other poly(ADP-ribose) polymerase proteins. Similarly, such mutant hPARP2 molecules may be prepared that lack residues of a functional domain, e.g., the catalytic domain, to create a dominant negative protein.

It is difficult to predict a priori the exact effect any particular modification, e.g., substitution, deletion, insertion, etc., will have on the biological activity of hPARP2. However, one skilled in the art will appreciate that the effect will be evaluated by routine screening assays. For example, a derivative typically is made by linker scanning site-directed mutagenesis of the DNA encoding the native hPARP2 molecule. The derivative is then expressed in a recombinant host, and, optionally, purified from the cell culture, for example, by immunoaffinity chromatography. The activity of the cell lysate or the purified derivative is then screened in a suitable screening assay for the desired characteristic. For example, a change in the immunological character of the functional derivative, such as affinity for a given antibody, is measured by a competitive type immunoassay. Changes in other parameters of the expressed product may be measured by the appropriate assay.

Antibodies

The present invention provides antibodies that bind with specificity to an hPARP2 polypeptide. An "antibody" as used herein is defined broadly as a protein that characteristically immunoreacts with an epitope (antigenic determinant) that is characteristic of the hPARP2 polypeptide. As used herein, an antibody is said to "immunoreact" with an antigen such as a polypeptide if the antibody specifically recognizes and binds an epitope that is characteristic of the antigen by way of one or more variable regions or one or more of the complementarity determining regions (CDRs) of the antibody.

An antibody that is immunoreactive with a given polypeptide may exhibit cross-reactivity to another polypeptide if the two polypeptides each comprise a common structural feature that defines the same characteristic epitope. In the case of related polypeptides, cross-reactivity can correlate to common structural features such as sequence identity, homology, or similarity found among the related polypeptides. Accordingly, families of polypeptides can often be identified by a cross-reactive antibody, i.e., an antibody that immunoreacts with some or all of the members of the polypeptide family sharing the common epitope. Thus, the invention encompasses antibodies that immunoreact with a particular member of the hPARP2 family of polypeptides, e.g., a polypeptide comprising the amino acid sequence defined by SEQ ID NO:2 or comprising amino acid residues 1 to 49 of SEQ ID NO:2. The invention further encompasses antibodies that immunoreact with some or all members of the hPARP2 family of polypeptides. Screening assays to determine the binding specificity of an antibody are well known and routinely practiced in the art [see Harlow et al. (Eds.), *Antibodies: A Laboratory Manual*, Ch. 6, Cold Spring Harbor Laboratory, Cold Spring Harbor N.Y. (1988)]. The immunoreactive specificity with which an antibody binds to a given polypeptide antigen is to be distinguished from interactions with other proteins, e.g., *Staphylococcus aureus* protein A or other antibodies in ELISA techniques; that are mediated through parts of the antibody other than the variable regions, in particular the constant regions of the antibody.

Antibodies include, for example, monoclonal antibodies, polyclonal antibodies, single chain antibodies (scFv antibodies), chimeric antibodies, multifunctional/multispecific (e.g., bifunctional or bispecific) antibodies, humanized antibodies, human antibodies, and CDR-grafted antibodies (including moieties that include CDR sequences that specifically immunoreact with a polypeptide of the invention). Antibodies according to the invention also include antibody fragments, so long as they exhibit the desired biological activity. "Antibody fragments" comprise a portion of a full-length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

Antibodies of the invention can be produced by any method known in the art. For example, polyclonal antibodies are isolated from mammals that have been immunized against the protein or a functional analog in accordance with methods known in the art. Briefly, polyclonal antibodies may be produced by injecting an immunogenic hPARP2 polypeptide (immunogen) into a host mammal (e.g., rabbit, mouse, rat, or goat). Adjuvants may be employed to increase the immune response. Sera from the host mammal are extracted and screened to obtain polyclonal antibodies that are specific for (immunoreact with) the hPARP2 polypeptide.

Monoclonal antibodies (also referred to herein as "mAbs") are preferred. As used herein "monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific ("monospecific"), being directed against a single antigenic site. Furthermore, in contrast to conventional (polyclonal) antibody preparations, which typically include different antibodies directed against different determinants (epitopes), each monoclonal antibody is directed against a single determinant on the antigen.

The modifier "monoclonal" indicates the character of the antibody as being obtained from a substantially homogeneous population of antibodies, and is not to be construed as requiring production of the antibody by any particular method. Monoclonal antibodies may be prepared using any suitable technique capable of yielding a continuous cell line producing a homogeneous antibody. Such methods include the immunological method [Köhler and Milstein, *Nature* 256:495–497 (1975); Campbell, "Monoclonal antibody technology, the production and characterization of rodent and human hybridomas" in Burdon et al. (Eds.), *Laboratory Techniques in Biochemistry and Molecular Biology*, Vol. 13, Elsevier Science Publishers, Amsterdam (1985)] or any similar method. Monoclonal antibodies may also be isolated from phage antibody libraries [Clackson et al., *Nature* 352:624–8 (1991); Marks et al., *J Mol Biol* 222:581–97 (1991)].

To illustrate, to produce monoclonal antibodies a host mammal is immunized by injection of an immunogenic hPARP2 polypeptide, and then boosted. Spleens are collected from immunized mammals a few days after the final boost. Cell suspensions from the spleens are fused with a tumor cell line to create immortalized hybrid cell lines or "hybridomas." Individual clones can be isolated by limiting dilution and then tested for the specificity of the antibodies they produce. Selected cells can then be grown, e.g., by the ascites method, to provide a continuous source of the desired homogeneous antibody.

Antibodies can be engineered using genetic techniques to produce chimeric antibodies including protein components from two or more species. For use in in vivo applications with a human subject, the antibody can be "humanized," i.e., modified to contain an antigen binding region from one species, e.g., a rodent, with the bulk of the antibody replaced with sequences derived from human immunoglobulin. In one method, the non-human CDRs of one species e.g., a mouse or rabbit, are inserted into a framework sequence of another species, e.g., a human, or into a consensus framework sequence. Further changes can then be introduced into the antibody framework to modulate affinity or immunogenicity of the engineered antibody. Methods are also known for inducing expression of engineered antibodies in various cell types, such as mammalian and microbial cell types. Numerous techniques for preparing engineered antibodies are described in the art [e.g., Owens and Young, *J Immunol Meth* 168:149–65 (1994)].

Antibodies further include recombinant polyclonal or monoclonal Fab fragments [e.g., Huse et al., *Science* 246:1275–81 (1989)]. Alternatively, techniques described for the production of single chain antibodies (e.g., U.S. Pat. No. 4,946,778) can be adapted to produce hPARP2-specific single chain antibodies (e.g., single chain Fv fragments; abbreviated "scFv"). Rapid, large-scale recombinant methods for generating antibodies may be employed, such as phage display or ribosome display methods, optionally followed by affinity maturation [see, e.g., Ouwehand et al., *Vox Sang* 74(Suppl 2):223–232 (1998); Rader et al., *Proc Natl Acad Sci USA* 95:8910–8915 (1998); Dall' Acqua et al., *Curr Opin Struct Biol* 8:443–450 (1998)].

Fully human antibodies are especially preferred for therapeutic use in humans, but they are typically difficult to produce. For example, when the immunogen is a human self-antigen, a human will typically not produce any immune response to the antigen. Methods for making fully human antibodies have been developed and are known in the art. Accordingly, fully human antibodies can be produced by using an immunogenic hPARP2 polypeptide to immunize an animal (e.g., mouse) that has been transgenically modified to express at least a significant fraction of the human repertoire of immunoglobulin genes [see e.g., Bruggemann et al., *Immunol Today* 17:391–7 (1996)].

As noted herein, host cells of the invention are a valuable source of immunogen for development of antibodies specifically immunoreactive with hPARP2. To be useful as an immunogen for the preparation of polyclonal or monoclonal antibodies, an hPARP2 peptide fragment must contain sufficient amino acid residues to define an immunogenic epitope. If the fragment is too short to be immunogenic per se, it may be conjugated to a carrier molecule. Suitable carrier molecules include, for example, keyhole limpet hemocyanin (KLH) and bovine serum albumin (BSA). Conjugation may be carried out by methods known in the art. One such method is to combine a cysteine residue of the fragment with a cysteine residue on the carrier molecule.

Antibodies of the invention are useful for therapeutic methods (by modulating activity of hPARP2), diagnostic methods (by detecting hPARP2 in a sample), as well as purification of hPARP2. The antibodies are particularly useful for detecting and/or quantitating hPARP2 expression in cells, tissues, organs, and lysates and extracts thereof, as well as in fluids such as serum, plasma, cerebrospinal fluid, urine, sputum, peritoneal fluid, pleural fluid, or bronchoalveolar lavage fluid. Kits comprising an antibody of the invention for any of the purposes described herein are also contemplated. In general, a kit of the invention also includes a control antigen with which the antibody immunoreacts, and may further include other reagents, containers, and package inserts.

Further, the invention includes neutralizing antibodies, i.e., antibodies that significantly inhibit or impair a biological activity of the proteins or functional analogs of the invention. In particular, neutralizing antibodies inhibit or impair the poly(ADP-ribose) polymerase activity of hPARP2. Neutralizing antibodies may be especially desirable for therapeutic and diagnostic applications.

Functional equivalents further include fragments of antibodies that have the same binding characteristics as, or that have binding characteristics comparable to, those of the whole antibody. Such fragments may contain one or both Fab fragments or the F(ab')$_2$ fragment. Preferably, the antibody fragments contain all six complement determining regions ("CDRs") of the whole antibody, although fragments containing fewer than all of such regions, such as three, four, or five CDRs, may also be functional. Fragments may be prepared by methods described in the art [e.g., Lamoyi et al., *J Immunol Meth* 56:235–43 (1983); Parham, *J Immunol* 131:2895–902 (1983)].

Moreover, specific binding proteins can be developed using isolated or recombinant hPARP2 products, hPARP2 variants, or cells expressing such products. Binding proteins are useful for purifying hPARP2 products and detection or quantification of hPARP2 products in fluid and tissue samples using known immunological procedures. Binding proteins are also manifestly useful in modulating (i.e., blocking, inhibiting, or stimulating) biological activities of hPARP2 polypeptides, especially those activities involved in signal transduction. Thus, neutralizing antibodies that inhibit the activity of hPARP2 polypeptides are provided. Anti-idiotypic antibodies specific for anti-hPARP2 antibodies are also contemplated.

Detectable Polynucleotide and Polypeptide Probes

The present invention further provides a method of detecting the presence of an hPARP2-encoding polynucleotide or an hPARP2 polypeptide in a sample. The method involves use of a labeled probe that recognizes the presence of a defined target in the sample. The probe may be an antibody that recognizes an hPARP2 polypeptide, or an oligonucleotide that recognizes a polynucleotide encoding hPARP2 polypeptide.

The probes of the invention can be detectably labeled in accordance with methods known in the art. In general, the probe can be modified by attachment of a detectable label (reporter) moiety to the probe, or a detectable probe can be manufactured with a detectable label moiety incorporated therein. The detectable label moiety can be any detectable moiety, many of which are known in the art, including radioactive atoms, electron dense atoms, enzymes, chromogens and colored compounds, fluorogens and fluorescent compounds, members of specific binding pairs, and the like.

Methods for labeling oligonucleotide probes have been described in the art [see, e.g., Leary et al., *Proc Natl Acad Sci USA* 80:4045–49 (1983); Renz and Kurz, *Nucleic Acids Res* 12:3435–44 (1984); Richardson and Gumport, *Nucleic Acids Res* 11:6167–84 (1983); Smith et al., *Nucleic Acids*

Res 13:2399–412 (1985); Meinkoth and Wahl, Anal Biochem 138:267–84 (1984); and U.S. Pat. Nos. 4,711,955; 4,687,732; 5,241,060; 5,244,787; 5,328,824; 5,580,990; and 5,714,327].

Methods for labeling antibodies have been also been described [see, e.g., Hunter et al., Nature 144:495–6 (1962); David et al., Biochemistry 13:1014–21:(1974); and U.S. Pat. Nos. 3,940,475 and 3,645,090].

The label moiety may be radioactive. Some examples of useful radioactive labels include $^{32}P$, $^{125}I$, $^{131}I$, and $^{3}H$. Use of radioactive labels has been described [e.g., UK patent document 2,034,323 and U.S. Pat. Nos. 4,358,535 and 4,302,204].

Some examples of non-radioactive labels include enzymes, chromogens, atoms and molecules detectable by electron microscopy, and metal ions detectable by their magnetic properties.

Some useful enzymatic labels include enzymes that cause a detectable change in a substrate. Some useful enzymes (and their substrates) include, for example, horseradish peroxidase (pyrogallol and o-phenylenediamine), beta-galactosidase (fluorescein beta-D-galactopyranoside), and alkaline phosphatase (5-bromo-4-chloro-3-indolyl phosphate/nitro blue tetrazolium). The use of enzymatic labels has been described in the art [see, e.g., UK patent document 2,019,404, European patent document EP 63,879, and Rotman, Proc Natl Acad Sci USA 47:1981–91 (1961)].

Useful reporter moieties include, for example, fluorescent, phosphorescent, chemiluminescent, and bioluminescent molecules, as well as dyes. Some specific colored or fluorescent compounds useful in the present invention include, for example, fluoresceins, coumarins, rhodamines, Texas red, phycoerythrins,. umbelliferones, Luminol®, and the like. Chromogens or fluorogens, i.e., molecules that can be modified (e.g., oxidized) to become colored or fluorescent or to change their color or emission spectra, are also capable of being incorporated into probes to act as reporter moieties under particular conditions.

The label moieties may be conjugated to the probe by methods that are well known in the art. The label moieties may be directly attached through a functional group on the probe. The probe either contains or can be caused to contain such a functional group. Some examples of suitable functional groups include, for example, amino, carboxyl, sulfhydryl, maleimide, isocyanrate, isothiocyanate.

Alternatively, label moieties such as enzymes and chromogens may be conjugated to antibodies or nucleotides by means of coupling agents, such as dialdehydes, carboduimides, dimaleimides, and the like.

The label moiety may also be conjugated to the probe by means of a ligand attached to the probe by a method-described above and a receptor for that ligand attached to the label moiety. Any of the known ligand-receptor binding pair combinations is suitable. Some suitable ligand-receptor pairs include, for example, biotin-avidin or -streptavidin, and antibody-antigen. The biotin-streptavidin combination may be preferred.

Methods of Using hparp2 Polynucleotides and hPARP2 Polypeptides

The scientific value of the information contributed through the disclosures of DNA and amino acid sequences of the present invention is manifest. As one series of examples, knowledge of the sequence of a cDNA for hparp2 makes possible through use of Southern hybridization or polymerase chain reaction (PCR) the identification of genomic DNA sequences encoding hPARP2 and hPARP2 expression control regulatory sequences. DNA/DNA hybridization procedures carried out with DNA sequences of the invention under moderately to highly stringent conditions are also expected to allow the isolation of DNAs encoding allelic variants of hPARP2. Similarly, non-human species genes encoding proteins homologous to hPARP2 can also be identified by Southern and/or PCR analysis. As an alternative, complementation studies can be useful for identifying other human hPARP2 products as well as non-human proteins, and DNAs encoding the proteins, sharing one or more biological properties of hPARP2. Oligonucleotides of the invention are also useful in hybridization assays to detect the capacity of cells to express hPARP2. Polynucleotides of the invention may also be the basis for diagnostic methods useful for identifying a genetic alteration in the hparp2 locus that underlies a disease state.

Oligonucleotides of the invention, as described herein, may be used in methods to amplify DNA for various purposes. "Amplification" according to the method of the invention refers to any molecular biology technique for detection of trace levels of a specific nucleic acid sequence by exponentially amplifying a template nucleic acid sequence. In particular, suitable amplification techniques include such techniques as the polymerase chain reaction (PCR), the ligase chain reaction (LCR) and variants thereof. PCR is known to be a highly sensitive technique, and is in wide use [see, for example, Innis et al., PCR Protocols: A Guide to Methods and Applications, Academic Press, Inc., San Diego (1990); Dieffenbach and Dveksler, PCR Primer: A Laboratory Manual, Cold Spring Harbor Laboratory Press, Plainview N.Y (1995); and U.S. Pat. Nos. 4,683,195; 4,800,195; and 4,965,188]. LCR is more recently developed [Landegren et al., Science 241:1077–80 (1988) and Barany et al., PCR Methods and Applications 1:5–16 (1991); an LCR kit is available from Stratagene]. LCR is known to be highly specific, and is capable of detecting point mutations. In certain circumstances, it is desirable to couple the PCR and LCR techniques to improve precision of detection. Other amplification techniques may be employed in accordance to the invention.

Oligonucleotide amplification primers are often provided as matched pairs of single-stranded oligonucleotides; one with sense orientation (5'43 3') and one with antisense (3'←5') orientation. Such specific primer pairs can be employed under optimized conditions for identification of a specific gene or condition. Alternatively, the same primer pair, nested sets of oligomers, or even a degenerate pool of oligomers, may be employed under less stringent conditions for detection and/or quantitation of closely related DNA or RNA sequences.

Such oligonucleotides can be used in various methods known in the art to extend the specified nucleotide sequences. These methods permit use of a known sequence to determine unknown adjacent sequence, thereby enabling detection and determination of upstream sequences such as promoters and regulatory elements.

For example, restriction-site polymerase chain reaction is a direct method that uses universal primers to retrieve unknown sequence adjacent to a known locus [see, e.g., Gobinda et al., PCR Methods Applic 2:318–22 (1993)]. In this method, genomic DNA is first amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region [Triglia et al., *Nucleic Acids Res* 16:8186 (1988)]. The primers may be designed using Oligo 4.0 (National Biosciences, Inc., Plymouth Minn.), or another appropriate program, to be 22–30 nucleotides in length, to have a GC content of 50% or more, and to anneal to the target sequence at temperatures about 68°–72° C. This method uses several restriction enzymes to generate a suitable fragment in the known region of a gene. The fragment is then circularized by intermolecular ligation and used as a PCR template.

Capture PCR is a method for PCR amplification of DNA fragments adjacent to a known sequence in human and yeast artificial chromosome (YAC) DNA [Lagerstrom et al., *PCR Methods Applic* 1:111–9 (1991)]. Capture PCR also requires multiple restriction enzyme digestions and ligations to place an engineered double-stranded sequence into an unknown portion of the DNA molecule before PCR. Walking PCR is a method for targeted gene walking that permits retrieval of unknown sequence [Parker et al., *Nucleic Acids Res* 19:3055–60 (1991)]. The PromoterFinder™ kit (Clontech, Palo Alto, Calif.) uses PCR, nested primers, and special libraries to "walk in" genomic DNA. This process avoids the need to screen libraries and is useful in finding intron/exon junctions.

Such methods can be used to explore genomic libraries to extend 5' sequence and to obtain endogenous hparp2 genomic sequence, including elements such as promoters, introns, operators, enhancers, repressors, and the like. Preferred libraries for screening for full-length cDNAs are ones that have been size-selected to include larger cDNAs. In addition, randomly primed libraries are preferred in that they will contain more sequences that contain the 5' and upstream regions of genes.

The oligonucleotide probes may also be used for mapping the endogenous genomic sequence. The sequence may be mapped to a particular chromosome or to a specific region of the chromosome using well known techniques. These include in situ hybridization to chromosomal spreads [Venna et al., *Human Chromosomes: A Manual of Basic Technique*, Pergamon Press, N.Y. (1988)], flow-sorted chromosomal preparations, or artificial chromosome constructions such as YACs, bacterial artificial chromosomes (BACS); bacterial P1 constructions, or single chromosome cDNA libraries.

Hybridization of chromosomal preparations and physical mapping techniques such as linkage analysis using established chromosomal markers are invaluable in extending genetic maps. Examples of genetic maps can be found in *Science* 270:410f (1995) and *Science* 265:1981f (1994). Often the placement of a gene on the chromosome of another mammalian species may reveal associated markers even if the number or arm of a particular human chromosome is not known. Such sequences can be assigned to particular structural features of chromosomes by physical mapping. This provides valuable information to investigators searching for disease genes using positional cloning or other gene discovery techniques. Once a disease or syndrome has been crudely localized by genetic linkage to a particular genomic region, any sequences mapping to that area may represent associated or regulatory genes for further investigation [see, e.g., Gatti et al., *Nature* 336:577–80 (1988)]. The polynucleotides of the invention may also be used to detect differences in the chromosomal location due to translocation, inversion, etc., between normal, carrier, or affected individuals.

The DNA sequence information provided by the present invention also makes possible the development, e.g., through homologous recombination or "knock-out" strategies [Capecchi, *Science* 244:1288–92 (1989)], of animals that fail to express functional hPARP2 or that express a variant of hPARP2. Such animals are useful as models for studying the in vivo activities of hPARP2 and modulators thereof.

As described herein, the invention provides antisense nucleic acid sequences that recognize and hybridize to polynucleotides encoding hPARP2. Modifications of gene expression can be obtained by designing antisense sequences to the control regions of the hparp2 gene, such as the promoters, enhancers, and introns. Oligonucleotides derived from the transcription initiation site, e.g., between −10 and +10 regions of the leader sequence, are preferred. Antisense RNA and DNA molecules may also be designed to block translation of mRNA by preventing the transcript from binding to ribosomes. The worker of ordinary skill will appreciate that antisense molecules of the invention include those that specifically recognize and hybridize to hparp2 DNA (as determined by sequence comparison of hparp2 DNA to DNA encoding other known molecules). The antisense molecules of the invention also include those that recognize and hybridize to DNA encoding other members of the hPARP2 family of proteins. Antisense polynucleotides that hybridize to multiple DNAs encoding other members of the hPARP2 family of proteins are also identifiable through sequence comparison to identify characteristic or signature sequences for the family of hPARP2 proteins. Accordingly, such antisense molecules preferably have at least 95%, more preferably at least 98%, and still more preferably at least 99% identity to the target hparp2 sequence.

Antisense polynucleotides are particularly relevant to regulating expression of hPARP2 by those cells expressing hparp2 mRNA. Antisense polynucleotides (preferably 10 to 20 bp oligonucleotides) capable of specifically binding to hparp2 expression control sequences or hparp2 RNA are introduced into cells, e.g., by a viral vector or a colloidal dispersion system such as a liposome. The antisense oligonucleotide binds to the hparp2 target nucleotide sequence in the cell and prevents transcription or translation of the target sequence. Phosphorothioate and methylphosphonate antisense oligonucleotides are specifically contemplated for therapeutic use under the invention. The antisense oligonucleotides may be further modified by poly-L-lysine, transferrin polylysine, or cholesterol moieties at their 5' ends [for a recent review of antisense technology, see Delihas et al., *Nature Biotechnology* 15:751–3 (1997)].

The invention further comprises methods to modulate hPARP2 expression by means of ribozyme technology [for a review, see Gibson and Shillitoe, *Mol Biotechnol* 7:125–37 (1997)]. Ribozyme technology can be used to inhibit translation of hparp2 mRNA in a sequence specific manner through (i) the hybridization of a complementary RNA to a target mRNA and (ii) cleavage of the hybridized mRNA through endonuclease activity inherent to the complementary RNA. Ribozymes can be identified by empirical methods such as using complementary oligonucleotides in ribonuclease protection assays, but more preferably are specifically designed based on scanning the target molecule for accessible ribozyme cleavage sites [Bramlage et al., *Trends Biotechnol* 16:434–8 (1998)]. Delivery of ribozymes to target cells can be accomplished using either exogenous or endogenous delivery techniques well known and practiced in the art. Exogenous can include use of targeting liposomes or direct local injection. Endogenous methods include use of viral vectors and non-viral plasmids.

Ribozymes can specifically modulate expression of hPARP2 when designed to be complementary to regions unique to a polynucleotide encoding hPARP2. "Specifically modulate," therefore is intended to mean that ribozymes of the invention recognize only a polynucleotide encoding hPARP2. Similarly, ribozymes can be designed to modulate expression of all or some of the hPARP2 family of proteins. Ribozymes of this type are designed to recognize nucleotide sequences conserved all or some of the polynucleotides encoding the hPARP2 family members.

The invention further embraces methods to modulate transcription of hparp2 through use of oligonucleotide-directed triple helix formation (also known as Hogeboom base-pairing methodology) [for a review, see Lavrovsky et al., *Biochem Mol Med* 62:11–22 (1997)]. Triple helix formation is accomplished using sequence-specific oligonucleotides that hybridize to double stranded DNA in the major groove as defined in the Watson-Crick model. This triple helix hybridization compromises the ability of the original double helix to open sufficiently for the binding of polymerases, transcription factors, or regulatory molecules. Preferred target sequences for hybridization include promoter and enhancer regions to permit transcriptional regulation of hPARP2 expression. Oligonucleotides that are capable of triple helix formation can alternatively be coupled to DNA damaging agents, which can then be used for site-specific covalent modification of target DNA sequences. See Lavrovsky et al. supra.

Both antisense RNA and DNA molecules and ribozymes of the invention may be prepared by any method known in the art for the synthesis of RNA molecules. These include techniques for chemically synthesizing oligonucleotides such as solid-phase phosphoramidite chemical synthesis. Alternatively, RNA molecules may be generated by in vitro or in vivo transcription of DNA sequences encoding the antisense RNA molecule. Such DNA sequences may be incorporated into a variety of vectors with suitable RNA polymerase promoters such as T7 or SP6. Alternatively, antisense cDNA constructs that synthesize antisense RNA constitutively or inducibly can be introduced into cell lines, cells, or tissues.

Mutations in a gene that result in loss of normal function of the gene product may underlie hPARP2-related disease states. The invention comprehends gene therapy to restore hPARP2 activity as indicated in treating those disease states characterized by a deficiency or absence of poly(ADP-ribose) polymerase activity associated with the hPARP2 enzyme. Delivery of functional hparp2 gene to appropriate cells is effected ex vivo, in situ, or in vivo by use of vectors, and more particularly viral vectors (e.g., adenovirus, adeno-associated virus, or retrovirus), or ex vivo by use of physical DNA transfer methods (e.g., liposomes or chemical treatments) [see, e.g., Anderson, *Nature* 392(6679 Suppl):25–30 (1998)]. Alternatively, it is contemplated that in other disease states, preventing the expression or inhibiting the activity of hPARP2 will be useful in treating those disease states. Antisense therapy or gene therapy can be applied to negatively regulate the expression of hPARP2.

The DNA and amino acid sequence information provided by the present invention also makes possible the systematic analysis of the structure and function of hPARP2 proteins. DNA and amino acid sequence information for hPARP2 also permits identification of molecules with which an hPARP2 polypeptide will interact. Agents that modulate (i.e., increase, decrease, or block) hPARP2 activity may be identified by incubating a putative modulator with hPARP2 and determining the effect of the putative modulator on hPARP2 activity. The selectivity of a compound that modulates the activity of the hPARP2 can be evaluated by comparing its activity on the hPARP2 to its activity on other proteins. Cell-based methods, such as dihybrid or trihybrid assays (to identify DNAs encoding binding partners) and split hybrid assays (to identify inhibitors of hPARP2.polypeptide interaction with a known binding partner), as well as in vitro methods, including assays in which an hPARP2 polypeptide, hparp2 polynucleotide, or a binding partner thereof is immobilized, and solution assays are contemplated under the invention.

Selective modulators may include, for example, antibodies and other proteins or peptides that-specifically bind to an hPARP2 polypeptide or an hPARP2-encoding polynucleotide, oligonucleotides that specifically bind to hPARP2 polypeptides or hPARP2-encoding polynucleotides, and other non-peptide compounds (e.g., isolated or synthetic organic molecules) that specifically react with hPARP2 polypeptides or hPARP2-encoding polynucleotides. Modulators also include compounds as described above but which interact with a specific binding partner of hPARP2 polypeptides. Mutant forms of hPARP2, such as those that affect the biological activity or cellular location of the wild-type hPARP2, are also contemplated under the invention. Presently preferred targets for the development of selective modulators include, for example:

(1) cytoplasmic or transmembrane regions of hPARP2 polypeptides that contact other proteins and/or localize hPARP2 within a cell;
(2) extracellular regions of hPARP2 polypeptides that bind specific binding partners;
(3) regions of the hPARP2 polypeptides that bind substrate;
(4) allosteric regulatory sites of the hPARP2 polypeptides;
(5) regions of the hPARP2 polypeptides that mediate multimerization.

Still other selective modulators include those that recognize specific regulatory or hPARP2-encoding nucleotide sequences. Modulators of hPARP2 activity may be therapeutically useful in treatment of a wide range of diseases and physiological conditions in which aberrant hPARP2 activity is involved.

An hPARP2-coding polynucleotide sequence may be used for the diagnosis of diseases resulting from or associated with hPARP2 expression or activity. For example, polynucleotide sequences encoding hPARP2 may be used in hybridization or PCR assays of biological samples, e.g., samples or extracts of fluids or tissues from biopsies or autopsies, to detect abnormalities in hPARP2 expression. Such qualitative or quantitative methods may include Southern or northern analysis, dot blot, or other membrane-based technologies; PCR technologies; dipstick, pin or chip technologies; and ELISA or other multiple-sample format technologies. These types of techniques are well known in the art and have been employed in commercially available diagnostic kits.

Such assays may be tailored to evaluate the efficacy of a particular therapeutic treatment regimen and may be used in animal studies, in clinical trials, or in monitoring the treatment of an individual patient. To provide a basis for the diagnosis of disease, a normal or standard profile for hPARP2 expression must be established. This is accomplished by combining a biological sample taken from a normal subject with an hparp2 polynucleotide, under conditions suitable for hybridization or amplification. Standard hybridization may be quantified by comparing the values obtained for normal subjects with a dilution series of positive controls run in the same experiment where a known amount of a purified hparp2 polynucleotide is used. Standard values obtained from normal samples may be compared with values obtained from samples from subjects potentially affected by a disorder or disease related to hPARP2 expression. Deviation between standard and subject values establishes the presence of the disease state. If disease is established, an existing therapeutic agent is administered, and treatment profile or values may be generated. The assay may be repeated on a regular basis to evaluate whether the values progress toward or return to the normal or standard pattern. Successive treatment profiles may be used to show the efficacy of treatment over a period of several days or several months.

Anti-hPARP2 antibodies are useful for the diagnosis of conditions, disorders, or diseases characterized by or associated with abnormal expression of an hPARP2 polypeptide. Diagnostic assays for hPARP2 polypeptides include methods that employ a labeled antibody to detect an hPARP2 polypeptide in a biological sample such as a body fluid, cells, tissues, sections, or extracts of such materials. The polypeptides and antibodies of the present invention may be used with or without modification. Preferably, the polypeptide or the antibody will be labeled by linking them, either covalently or non-covalently, with a detectable label moiety as described herein.

Antibody-based methods for detecting the presence of hPARP2 polypeptides in biological samples are enabled by virtue of the present invention. Assays for detecting the presence of proteins with antibodies have been previously described, and follow known formats, such as enzyme-linked immunosorbent assay (ELISA), radioimmunoassay (RIA), and fluorescence activated cell sorting (FACS) and flow cytometry, western blots, sandwich assays, and the like. These formats are normally based on incubating an antibody with a sample suspected of containing the hPARP2 protein and detecting the presence of a complex between the antibody and the protein. The antibody is labeled either before, during, or after the incubation step. The specific concentrations of antibodies, the temperature and time of incubation, as well as other such assay conditions, can be varied, depending upon various factors including the concentration of antigen in the sample, the nature of the sample, etc. Those skilled in the art will be able to determine operative and optimal assay conditions for each determination by employing routine experimentation [see, e.g., Hampton et al., *Serological Methods: A Laboratory Manual*, APS Press, St Paul, Minn. (1990)].

To provide a basis for the quantitation of hPARP2 protein in a sample or for the diagnosis of disease, normal or standard values of hPARP2 polypeptide expression must be established. This is accomplished by combining body fluids or cell extracts taken from a normal sample or from normal subjects, either animal or human, with antibody to an hPARP2 polypeptide. The amount of standard complex formation may be quantified by comparing it with a dilution series of positive controls where a known amount of antibody is combined with known concentrations of a purified hPARP2 polypeptide. Then, standard values obtained from normal samples may be compared with values obtained from samples from test sample, e.g., subjects potentially affected by a disorder or disease related to an hPARP2 expression. Deviation between standard and test values establishes the presence of the disease state.

Methods for Identifying Modulators of hPARP2 Activity

The hPARP2 protein, as well as fragments thereof possessing biological activity can be used for screening putative modulator compounds in any of a variety of drug screening techniques. The term "modulator" as used herein refers to a compound that acts as an agonist or as an antagonist of hPARP2 activity. Modulators according to the invention include allosteric modulators of activity as well as inhibitors of activity. An "agonist" of hPARP2 is a compound that enhances or increases the ability of hPARP2 to carry out any of its biological functions. An example of such an agonist is an agent that increases the ability of hPARP2 to bind to damaged DNA or to polymerize ADP-ribose. An "antagonist" of hPARP2 is a compound that diminishes or abolishes the ability of hPARP2 to carry out any of its biological functions. An example of such antagonists is an anti-hPARP2 antibody.

Accordingly, the invention provides a method for screening a plurality of test compounds for specific binding affinity with an hPARP2 polypeptide, comprising providing a plurality of test compounds; combining an hPARP2 polypeptide with each of the plurality of test compounds for a time sufficient to allow binding under suitable conditions; and detecting binding of the hPARP2 polypeptide to each of the plurality of test compounds, thereby identifying those test compounds that specifically bind the hPARP2 polypeptide.

The present invention also provides a method of identifying a modulator of a biological activity of an hPARP2 polypeptide, comprising the steps of a) contacting the compound with an hPARP2 polypeptide, b) incubating the mixture of step a) with a substrate under conditions suitable for the biological activity, c) measuring the amount of the biological activity; and d) comparing the amount of biological activity of step c) with the amount of biological activity obtained with the hPARP2 polypeptide, incubated without the compound, thereby determining whether the compound stimulates or inhibits the biological activity. In one embodiment of the method, the hPARP2 polypeptide is a fragment from the non-catalytic region of the hPARP2 and provides a method to identify allosteric modulators of hPARP2. In another embodiment, the hPARP2 polypeptide is a fragment from the catalytic region of hPARP2 and provides a method to identify inhibitors of the biological activity.

Accordingly, the polypeptide employed in such methods may be free in solution, affixed to a solid support, displayed on a cell surface, or located intracellularly. The modulation of activity or the formation of binding complexes between the hPARP2 polypeptide and the agent being tested may be measured. hPARP2 polypeptides are amenable to biochemical or cell-based high throughput screening (HTS) assays according to methods known and practiced in the art, including melanophore assay systems to investigate receptor-ligand interactions, yeast-based assay systems, and mammalian cell expression systems [for a review, see Jayawickreme and Kost, *Curr Opin Biotechnol* 8:629–34 (1997)]. Automated and miniaturized HTS assays are also comprehended [e.g., Houston and Banks, *Curr Opin Biotechnol* 8:734–40 (1997)].

Such HTS assays are used to screen libraries of compounds to identify particular compounds that exhibit a desired property. Any library of compounds may be used, including chemical libraries, natural product libraries, combinatorial libraries comprising random or designed oligopeptides, oligonucleotides, or other organic compounds.

Chemical libraries may contain known compounds, proprietary structural analogs of known compounds, or compounds that are identified from natural product screening.

Natural product libraries are collections of materials isolated from naturals sources, typically, microorganisms, animals, plants, or marine organisms. Natural products are isolated from their sources by fermentation of microorganisms followed by isolation and extraction of the fermentation broths or by direct extraction from the microorganisms or tissues (plants or animal) themselves. Natural product libraries include polyketides, non-ribosomal peptides, and variants (including non-naturally occurring variants) thereof [for a review, see Cane et al., *Science* 282:63–8 (1998)].

Combinatorial libraries are composed of large numbers of related compounds, such as peptides, oligonucleotides, or other organic compounds as a mixture. Such compounds are relatively straightforward to design and prepare by traditional automated synthesis protocols, PCR, cloning or proprietary synthetic methods. Of particular interest are peptide and oligonucleotide combinatorial libraries.

Still other libraries of interest include peptide, protein, peptidomimetic, multiparallel synthetic collection, recombinatorial, and polypeptide libraries [for a review of combinatorial chemistry and libraries created thereby, see Myers, *Curr Opin Biotechnol* 8:701–7 (1997)].

Once compounds have been identified that show activity as modulators of hPARP2 function, a program of optimization can be undertaken in an effort to improve the potency and or selectivity of the activity. This analysis of structure-activity relationships (SAR) typically involves of iterative series of selective modifications of compound structures and their correlation to biochemical or biological activity. Families of related compounds can be designed that all exhibit the desired activity, with certain members of the family potentially qualifying as therapeutic candidates.

The invention also encompasses the use of competitive drug screening assays in which neutralizing antibodies capable of binding an hPARP2 polypeptide specifically compete with a test compound for binding to the hPARP2 polypeptide. In this manner, the antibodies can be used to detect the presence of any compound, e.g., another peptide that shares one or more antigenic determinants with the hPARP2 polypeptide.

Therapeutic Uses of hPARP2-Encoding Polynucleotides and hPARP2 Polypeptides

The invention provides a method for inhibiting the expression or activity of hPARP2 therapeutically or prophylactically. The method comprises administering an hPARP2 antagonist in an amount effective for inhibiting hPARP2 expression or activity. The invention thus provides a method for treating tissue damage resulting from cell damage or death due to necrosis or apoptosis, comprising administering to the animal an effective amount of a compound that inhibits hPARP2 activity. This method may be employed in treating persons who are or may be subject to any condition whose symptoms or pathology is mediated by hPARP2 expression or activity.

The method may further involve administering an antagonist of another poly(ADP-ribose) polymerase activity, such as activity associated with the enzymes PARP1, tankyrase, and the like. Exemplary PARP1 antagonists suitable for use in this embodiment include, for example, the compounds described in Banasik et al., *J Biol Chem* 267:1569–75 (1992); and in PCT patent publications WO 99/11623 and WO 99/11649. Alternatively, the hPARP2 inhibitory method may entail use of a compound that antagonizes both hPARP2 and another enzyme having PARP activity.

"Treating" as used herein refers to preventing a disorder from occurring in an animal that may be predisposed to the disorder, but has not yet been diagnosed as having it; inhibiting the disorder, i.e., arresting its development; relieving the disorder, i.e., causing its regression, or ameliorating the disorder, i.e., reducing the severity of symptoms associated with the disorder. "Disorder" is intended to encompass medical disorders, diseases, conditions, syndromes, and the like, without limitation.

In particular, the method of the invention may be employed to treat humans therapeutically or prophylactically who are or may subject to an inflammatory disorder. One aspect of the present invention derives from the ability of hPARP2 and its functional derivatives to interact with damaged DNA and to signal or induce cell death. Without intending to be bound by any one theory, it is believed that, because inflammation involves processes that may be injurious to DNA, and because hPARP2 may inappropriately induce cell death under such conditions, antagonists of hPARP2 may be used to suppress injury associated with inflammation.

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorders" can also refer to pathological states mediated by influx of leukocytes and or neutrophil chemotaxis.

"Inflammation" as used herein refers to a localized, protective response elicited by injury or destruction of tissues, which serves to destroy, dilute or wall off (sequester) both the injurious agent and the injured tissue. Inflammation is notably associated with influx of leukocytes and or neutrophil chemotaxis. Inflammation may result from infection with pathogenic organisms and viruses and from noninfectious means such as trauma or reperfusion following myocardial infarction or stroke, immune response to foreign antigen, and autoimmune responses. Accordingly, inflammatory disorders amenable to the invention encompass disorders associated with reactions of the specific defense system as well as with reactions of the non-specific defense system.

As used herein, the term "specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "non-specific defense system" as used herein refers to inflammatory disorders that are mediated by leukocytes that are incapable of immunological memory (e.g., granulocytes, macrophages). Examples of inflammation that result, at least in part, from a reaction of the non-specific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents. "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue (including organs or cells (e.g., bone marrow)), characterized by a loss of function of the grafted and surrounding tissues, pain, swelling, leukocytosis, and thrombocytopenia.

The therapeutic methods of the present invention include methods for the amelioration of disorders associated with inflammatory cell activation. "Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T Iymphocytes, B lymnphocytes, granulocytes (polymorphonuclear leukocytes including neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The present invention enables methods of treating such diseases as arthritic diseases, such as rheumatoid arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as Crohn's disease, ulcerative colitis and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion associated syndromes; and cytokine-induced toxicity.

The method has particular utility in treating humans who are or may be subject to reperfusion injury, i.e., injury resulting from situations in which a tissue or organ experiences a period of ischemia followed by reperfusion. The term "ischernia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of hPARP2 expression or activity will result in reduced amounts of reperfusion injury in such situations.

With respect to the nervous system, global ischemia occurs when blood flow to the entire brain ceases for a period. Global ischemia may result from cardiac arrest. Focal ischemia occurs when a portion of the brain is deprived of its normal blood supply. Focal ischemia may result from thromboembolytic occlusion of a cerebral vessel, traumatic head injury, edema, or brain tumor. Even if transient, both global and focal ischemia can cause widespread neuronal damage. Although nerve tissue damage occurs over hours or even days following the onset of ischemia, some permanent nerve tissue damage may develop in the initial minutes following the cessation of blood flow to the brain. Much of this damage has been attributed to glutamate toxicity and to the secondary consequences of tissue reperfusion, such as the release of vasoactive products by damaged endothelium and the release of cytotoxic products, such as free radicals and leukotrienes, by the damaged tissue.

Ischemia can also occur in the heart in myocardial infarction and other cardiovascular disorders in which the coronary arteries have been obstructed as a result of atherosclerosis, thrombus, or spasm. For example, the method of the invention is believed to be useful for treating cardiac tissue damage, particularly damage resulting from cardiac ischemia or caused by reperfusion injury in mammals.

The invention further provides a method for treating a neurological disorder, comprising administering an neuroprotective amount of an hPARP2 antagonist. Neurological disorders that are treatable by the method the present invention encompass disorders such as peripheral neuropathy caused by physical injury or disease state; head trauma such as traumatic brain injury, physical damage to the spinal cord, stroke associated with brain damage, such as vascular stroke associated with hypoxia and brain damage, global or focal cerebral ischemia; and cerebral reperfusion injury; demyelinating diseases such as multiple sclerosis, and neurological disorders relating to neurodegeneration. Examples of neurological disorders further include, without limitation, trigeminal neuralgia; glossopharyngeal neuralgia; Bell's palsy; myasthenia gravis; muscular dystrophy; amyotrophic lateral sclerosis (ALS); progressive muscular atrophy; progressive bulbar inherited muscular atrophy; herniated, ruptured or prolapsed invertebrate disk syndromes; cervical spondylosis; plexus disorders; thoracic outlet destruction syndromes; peripheral neuropathies such as those caused by lead, dapsone, ticks, porphyria, or Guillain-Barre syndrome; Alzheimer's disease; Huntington's Disease and Parkinson's disease. The term "neurodegenerative diseases" includes Alzheimer's disease, Parkinson's disease, Huntington's disease, and ALS.

"Neuroprotective" as used herein refers to the effect of reducing, arresting, or ameliorating nervous insult, or to the effect of protecting, resuscitating, or reviving nervous tissue that has suffered nervous insult.

"Nervous tissue" as used herein refers to the various components that make up the nervous system including, without limitation, neurons, neural support cells, glia Schwann cells, vasculature contained within and supplying these structures, the central nervous system, the brain, the brain stem, the spinal cord, the junction of the central nervous system with the peripheral nervous system, the peripheral nervous system, and allied structures.

As used herein, "nervous insult" refers to any damage to nervous tissue and any disability or death resulting therefrom. The cause of nervous insult may be metabolic, toxic, neurotoxic, iatrogenic, thermal or chemical, and includes without limitation, vascular stroke, global and focal ischemia, hypoxia, cerebrovascular accident, trauma, surgery, pressure, mass effect, hemorrhage, radiation, vasospasm, neurodegenerative disease, infection, Parkinson's disease, ALS, myelination/demyelination process, epilepsy, cognitive disorder, glutamate abnormality and secondary effects thereof.

"Preventing neurodegeneration" includes the ability to prevent neurodegeneration in patients who have been diagnosed as having a neurodegenerative disease or who are at risk of developing a neurodegenerative disease. The term also encompasses preventing further neurodegeneration in patients who are already suffering from or have symptoms of a neurodegenerative disease.

As used herein "nervous function" refers to the various functions of the nervous system, which among other things provide an awareness of the internal and external environments of the body, make possible voluntary and reflex activities between the various. Structural elements of the organism, and balance the organisms response to environmental changes.

Further, according to the invention, there is provided a method of administering an hPARP2 antagonist to a human in an amount sufficient to effect a neuronal activity, particularly one that is not mediated by NMDA neurotoxicity. Such neuronal activity may consist of stimulation of damaged neurons, promotion of neuronal regeneration, prevention of neurodegeneration and treatment of a neurological disorder.

The present invention also relates to a method of treating a cardiovascular disorder in an animal, comprising administering to the animal an effective amount of a compound that inhibits hPARP2 activity. "Cardiovascular disorders" as used herein refers to those disorders that can either cause ischemia or are caused by reperfusion of the heart. Examples include, but are not limited to, coronary artery disease, angina pectoris myocardial infarction, cardiovascular tissue damage caused by cardiac arrest, cardiovascular tissue damage caused by cardiac bypass, cardiogenic shock, and related conditions that would be known by those of ordinary skill in the art or that involve dysfunction of or tissue damage to the heart or vasculature, especially, but not limited to, tissue damage related to PARP activation. The methods of the invention are especially helpful in treating the acute forms of the above cardiovascular disorders.

The invention also relates to a method of treating neoplastic tissue growth, e.g., cancer, in an animal, comprising administering to the animal an effective amount of a compound that inhibits hPARP2 activity. In this embodiment, the method may further comprise adjuvant administration of a chemotherapeutic or anti-cancer drug and/or radiation therapy.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, cancers invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Neoplasms treatable by the present invention include solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas and other cancers that typically do not present as a tumor mass, but are distributed in the vascular or lymphoreticular systems.

The type of cancer or tumor cells amenable to treatment according to the invention include, for example, ACTH-producing tumor, acute lymphocytic leukemia, acute non-lymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head and neck cancer, Hodgkin's lymphoma, Kaposi's sarcoma, kidney cancer, liver cancer, lung cancer (small and non-small cell), malignant peritoneal effusion, malignant pleural effusion, melanoma, mesothelioma, multiple myeloma, neuroblastoma, glioma, non-Hodgkin's lymphoma, osteosarcoma, ovarian cancer, ovarian (germ cell) cancer, pancreatic cancer, penile cancer, prostate cancer, retinoblastoma, skin cancer, soft tissue sarcoma, squamous cell carcinomas, stomach cancer, testicular cancer, thyroid cancer, trophoblastic neoplasms, uterine cancer, vaginal cancer, cancer of the vulva, and Wilm's tumor.

The invention further relates to radiosensitizing tumor cells. The term "radiosensitizer" as used herein is defined as a molecule,preferably a low molecular weight molecule, administered to a human or other animal in therapeutically effective amounts to increase the sensitivity of the cells to electromagnetic radiation and/or to promote the treatment of diseases that are treatable with electromagnetic radiation. Diseases that are treatable with electromagnetic radiation include neoplastic diseases, benign and malignant tumors, and cancerous cells. Electromagnetic radiation treatment of other diseases not listed herein is also contemplated by the present invention. The term "radiation" as used herein includes, but is not limited to, electromagnetic radiation having wavelengths in the range of $10^{-20}$ to $10^0$ meters. Preferred embodiments of the present invention employ gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1.0 mm), or microwave radiation (1 mm to 30 cm).

Radiosensitizers are known to increase the sensitivity of cancerous cells to the toxic effects of electromagnetic radiation. Several mechanisms for the mode of action of radiosensitizers have been suggested in the literature including: hypoxic cell radiosensitizers, e.g., 2-nitroimidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation ion-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of X-rays. Examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives thereof.

Photodynamic therapy (PDT) of cancers employs visible light as the radiation activator of the sensitizing agent. Examples of photodynamic radiosensitizers include, but are not limited to: hematoporphyrin derivatives, Photofrin, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives thereof.

Radiosensitizers may be administered in conjunction with a therapeutically effective amount of one or more other compounds, including but not limited to: compounds that promote the incorporation of radiosensitizers to the target cells; compounds that control the flow of therapeutics, nutrients, and/or oxygen to the target cells; chemotherapeutic agents that act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'-deoxythymidine oxygen, carbogen, red cell transfusions, perfluorocarbons (e.g., Fluosol-DA), 2,3-DPG, BW12C, calcium channel blockers, pentoxyfylline, anti-angiogenesis compounds, hydralazine, and L-BSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives thereof.

The present invention further relates to use of hPARP2 antagonists in methods of:

a) treating or preventing tissue damage resulting from cell damage or death due to necrosis or apoptosis, and conditions and diseases related thereto including, but not limited to, renal failure, cachexia, retinal ischemia, skin aging, osteoarthritis, osteoporosis, chronic pain, acute pain, neuropathic pain, muscular dystrophy or other degenerative diseases of skeletal muscle involving replicative senescence, age-related macular degeneration, AIDS and other immune senescence diseases, and cancer;

b) extending the lifespan and proliferative capacity of cells;

c) altering gene expression in senescent cells by increasing expression of young cell-specific genes and/or decreasing expression of senescent cell-specific genes and to extend or increase the lifespan or proliferative capacity of cells; and d) treating disease or disease conditions induced or exacerbated by cellular senescence such as skin aging.

The hparp2 polynucleotides provided by the invention also enable therapeutic applications of these polynucleotides in treating the diseases and disorders described herein whose etiology involves hPARP2 expression or activity. For example, an hparp2 antisense molecule may provide the basis for treatment of various abnormal conditions related to excessive or undesirable levels of poly(ADP-ribose) polymerase activity. Alternatively, polynucleotide sequences encoding hparp2 may provide the basis for the treatment of various abnormal conditions related to deficiency of poly (ADP-ribose) polymerase activity.

Expression vectors derived from retroviruses, adenovirus, herpes, or vaccinia viruses, or from various bacterial plasmids, may be used for delivery of recombinant hparp2 sense or antisense molecules to the targeted cell population. Methods that are well known to those skilled in the art can be used to construct recombinant vectors containing hparp2 [see, e.g., Sambrook et al., supra, and Ausubel et al., supra]. Alternatively, recombinant hparp2 can be delivered to target cells in liposomes.

The full-length cDNA sequence, and/or its regulatory elements, enables researchers to use an hparp2 polynucleotide as a tool in sense [Youssoufian and Lodish, *Mol Cell Biol* 13:98–104 (1993)] or antisense [Eguchi et al., *Annu Rev Biochem* 60:631–52 (1991)] investigations of gene function. Oligonucleotides, designed from the cDNA or control sequences obtained from the genomic DNA, can be used in vitro or in vivo to inhibit expression. Such technology is now well known in the art, and sense or antisense oligonucleotides or larger fragments can be designed from various locations along the coding or control regions.

Additionally, hPARP2 expression can be modulated by transfecting a cell or tissue with expression vectors that express high levels of an hparp2 polynucleotide fragment in conditions where it would be preferably to block a biological activity of hPARP2. Such constructs can flood cells with untranslatable sense or antisense sequences. Even in the absence of integration into the DNA, such vectors may continue to transcribe RNA molecules until all copies of the vector are disabled by endogenous nucleases. Such transient expression may be accomplished using a non-replicating vector or a vector incorporating appropriate replication elements.

Methods for introducing vectors into cells or tissue include those methods discussed herein. In addition, several of these transformation or transfection methods are equally suitable for ex vivo therapy. Furthermore, the hparp2 polynucleotide sequences disclosed herein may be used in molecular biology techniques that have not yet been developed, provided the new techniques rely on properties of nucleotide sequences that are currently known, including but not limited to such properties as the triplet genetic code and specific base pair interactions.

Pharmaceutical Compositions

The present invention further relates to pharmaceutical compositions that comprise a chemical or biological compound ("agent") that is active as a modulator of hPARP2 expression or activity and a biocompatible pharmaceutical carrier, adjuvant, or vehicle. The active agent in the pharmaceutical compositions may be selected from among all or portions of hparp2 polynucleotide sequences, hparp2 antisense molecules, hPARP2 polypeptides, protein, peptide, or organic modulators of hPARP2 bioactivity, such as inhibitors, antagonists (including antibodies) or agonists. Preferably, the agent is active in treating a medical condition that is mediated by or characterized by hPARP2 expression or activity. The composition can include the agent as the only active moiety or in combination with other nucleotide sequences, polypeptides, drugs, or hormones mixed with excipient(s) or other pharmaceutically acceptable carriers.

Techniques for formulation and administration of pharmaceutical compositions may be found in *Remington's Pharmaceutical Sciences*, 18$^{th}$ Ed., Mack Publishing Co, Easton Pa., 1990. The pharmaceutical compositions of the present invention may be manufactured using any conventional method, e.g., mixing, dissolving, granulating, dragée-making, levigating, emulsifying, encapsulating, entrapping, melt-spinning, spray-drying, or lyophilizing processes. However, the optional pharmaceutical formulation will be determined by one of skill in the art depending on the route of administration and the desired dosage. Such formulations may influence the physical state, stability, rate of in vivo release, and rate of in vivo clearance of the administered agent. Depending on the condition being treated, these pharmaceutical compositions may be formulated and administered systemically or locally.

The pharmaceutical compositions may be administered to the subject by any conventional method, including parenteral and enteral techniques. Parenteral administration modalities include those in which the composition is administered by a route other than through the gastrointestinal tract, for example, intravenous, intraarterial, intraperitoneal, intramedullary, intramuscular, intraarticular, intrathecal, and intraventricular injections. Enteral administration modalities include, for example, oral (including buccal and sublingual) and rectal administration. Transepithelial administration modalities include, for example, transmucosal administration and transdermal administration. Transmucosal administration includes, for example, enteral administration as well as nasal, inhalation, and deep lung administration; vaginal administration; and rectal administration. Transdermal administration includes passive or active transdermal or transcutaneous modalities, including, for example, patches and iontophoresis devices, as well as topical application of pastes, salves, or ointments. Surgical techniques include implantation of depot (reservoir) compositions, osmotic pumps, and the like. A preferred route of administration for treatment of inflammation would be local or topical delivery for localized inflammation such as arthritis, and intravenous delivery for reperfusion injury or for systemic conditions such as septicemia.

The pharmaceutical compositions are formulated to contain suitable pharmaceutically acceptable carriers, and may optionally comprise excipients and auxiliaries that facilitate processing of the active compounds into preparations that can be used pharmaceutically. The administration modality will generally determine the nature of the carrier. For example, formulations for parenteral administration may comprise aqueous solutions of the active compounds in water-soluble form. Carriers suitable for parenteral administration can be selected from among saline, buffered saline, dextrose, water, and other physiologically compatible solutions. Preferred carriers for parenteral administration are physiologically compatible buffers such as Hank's solution, Ringer's solutions, or physiologically buffered saline. For tissue or cellular administration, penetrants appropriate to the particular barrier to be permeated are used in the formulation. Such penetrants are generally known in the art. For preparations comprising proteins, the formulation may include stabilizing materials, such as polyols (e.g., sucrose) and/or surfactants (e.g., nonionic surfactants), and the like.

Alternatively, formulations for parenteral use may comprise suspensions of the active compounds prepared as appropriate oily injection suspensions. Suitable lipophilic solvents or vehicles include fatty oils, such as sesame oil, and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Emulsions, e.g., oil-in-water and water-in-oil dispersions, can also be used, optionally stabilized by an emulsifying agent or dispersant (surface-active materials; surfactants). Liposomes containing the active agent may also be employed for parenteral administration.

Alternatively, the pharmaceutical compositions comprising the agent in dosages suitable for oral administration can be formulated using pharmaceutically acceptable carriers well known in the art. The preparations formulated for oral administration may be in the form of tablets, pills, capsules, cachets, dragées, lozenges, liquids, gels, syrups, slurries, suspensions, or powders. To illustrate, pharmaceutical preparations for oral use can be obtained by combining the active compounds with a solid excipient, optionally grinding the resulting mixture, and processing the mixture of granules, after adding suitable auxiliaries if desired, to obtain tablets or dragée cores. Note that oral formulations may employ liquid carriers similar in type to those described for parenteral use, e.g., buffered aqueous solutions, suspensions, and the like.

Preferred oral formulations include tablets, dragées, and gelatin capsules. These preparations may contain one or excipients, which include, without limitation:

a) diluents such as sugars, including lactose, dextrose, sucrose, mannitol, or sorbitol;

b) binders such as magnesium aluminum silicate, starch from corn, wheat, rice, potato, etc.;

c) cellulose materials such as methyl cellulose, hydroxypropylmethyl cellulose, and sodium carboxymethyl cellulose, polyvinyl pyrrolidone, gums such as gum arabic and gum tragacanth, and proteins such as gelatin and collagen;

d) disintegrating or solubilizing agents such as cross-linked polyvinyl pyrrolidone, starches, agar, alginic acid or a salt thereof such as sodium alginate, or effervescent compositions;

e) lubricants such as silica, talc, stearic acid or its magnesium or calcium salt, and polyethylene glycol;

f) flavorants, and sweeteners;
g) colorants or pigments, e.g., to identify the product or to characterize the quantity (dosage) of active compound; and
h) other ingredients such as preservatives, stabilizers, swelling agents, emulsifying agents, solution promoters, salts for regulating osmotic pressure, and buffers.

Gelatin capsules include push-fit capsules made of gelatin, as well as soft, sealed capsules made of gelatin and a coating such as glycerol or sorbitol. Push-fit capsules can contain the active ingredient(s) mixed with fillers, binders, lubricants, and/or stabilizers, etc. In soft capsules, the active compounds may be dissolved or suspended in suitable fluids, such as fatty oils, liquid paraffin, or liquid polyethylene glycol with or without stabilizers.

Dragée cores can be provided with suitable coatings such as concentrated sugar solutions, which may also contain gum arabic, talc, polyvinyl pyrrolidone, carbopol gel, polyethylene glycol, and/or titanium dioxide, lacquer solutions, and suitable organic solvents or solvent mixtures.

The pharmaceutical composition may be provided as a salt of the active agent, which can be formed with many acids, including but not limited to hydrochloric, sulfuric, acetic, lactic, tartaric, malic, succinic, etc. Salts tend to be more soluble in aqueous or other protonic solvents that are the corresponding free base forms.

To be effective therapeutically in modulating central nervous system targets, the agents used in the methods of the invention should readily penetrate the blood brain barrier when peripherally administered. Compounds that cannot penetrate the blood brain barrier, however, can still be effectively administered by an intravenous route.

As noted above, the characteristics of the agent itself and the formulation of the agent can influence the physical state, stability, rate of in vivo release, and rate of in vivo clearance of the administered agent. Such pharmacokinetic and pharmacodynamic information can be collected through preclinical in vitro and in vivo studies, later confirmed in humans during the course of clinical trials. Thus, for any compound used in the method of the invention, a therapeutically effective dose can be estimated initially from biochemical and/or cell-based assays. Then, dosage can be formulated in animal models to achieve a desirable circulating concentration range that modulates hPARP2 expression or activity. As human studies are conducted, further information will emerge regarding the appropriate dosage levels and duration of treatment for various diseases and conditions.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the "therapeutic index," which is typically expressed as the ratio $LD_{50}/ED_{50}$. Compounds that exhibit large therapeutic indices are preferred. The data obtained from such cell culture assays and additional animal studies can be used in formulating a range of dosage for human use. The dosage of such compounds lies preferably within a range of circulating concentrations that include the $ED_{50}$ with little or no toxicity.

For the method of the invention, any effective administration regimen regulating the timing and sequence of doses may be used. Doses of the agent preferably include pharmaceutical dosage units comprising an effective amount of the agent. As used herein, "effective amount" refers to an amount sufficient to modulate hPARP2 expression or activity and/or derive a measurable change in a physiological parameter of the subject through administration of one or more of the pharmaceutical dosage units.

Exemplary dosage levels for a human subject are of the order of from about 0.001 milligram of active agent per kilogram body weight (mg/kg) to about 100 mg/kg. Typically, dosage units of the active agent comprise from about 0.01 mg to about 10,000 mg, preferably from about 0.1 mg to about 1,000 mg, depending upon the indication, route of administration, etc. Depending on the route of administration, a suitable dose may be calculated according to body weight, body surface area, or organ size. The final dosage regimen will be determined by the attending physician in view of good medical practice, considering various factors that modify the action of drugs, e.g., the agent's specific activity, the severity of the disease state, the responsiveness of the patient, the age, condition, body weight, sex, and diet of the patient, the severity of any infection, etc. Additional factors that may be taken into account include time and frequency of administration, drug combination(s), reaction sensitivities, and tolerance/response to therapy. Further refinement of the dosage appropriate for treatment involving any of the formulations mentioned herein is done routinely by the skilled practitioner without undue experimentation, especially in light of the dosage information and assays disclosed, as well as the pharmacokinetic data observed in human clinical trials. Appropriate dosages may be ascertained through use of established assays for determining concentration of the agent in a body fluid or other sample together with dose response data.

The frequency of dosing will depend on the pharmacokinetic parameters of the agent and the route of administration. Dosage and administration are adjusted to provide sufficient levels of the active moiety or to maintain the desired effect. Accordingly, the pharmaceutical compositions can be administered in a single dose, multiple discrete doses, continuous infusion, sustained release depots, or combinations thereof, as required to maintain desired minimum level of the agent. Short-acting pharmaceutical compositions (i.e., short half-life) can be administered once a day or more than once a day (e.g., two, three, or four times a day). Long acting pharmaceutical compositions might be administered every 3 to 4 days, every week, or once every two weeks. Pumps, such as subcutaneous, intraperitoneal, or subdural pumps, may be preferred for continuous infusion.

Compositions comprising a compound of the invention formulated in a pharmaceutical acceptable carrier may be prepared, placed in an appropriate container, and labeled for treatment of an indicated condition. Conditions indicated on the label may include treatment of inflammatory disorders, cancer, nervous tissue injury, etc. Kits are also contemplated, wherein the kit comprises a dosage form of a pharmaceutical composition and a package insert containing instructions for use of the composition in treatment of a medical condition.

The following Examples are provided to further aid in understanding the invention. The particular materials and conditions employed are intended to exemplify particular aspects of the invention and should not be construed to limit the reasonable scope thereof.

The Examples presuppose an understanding of conventional methods well-known to those persons having ordinary skill in the art to which the examples pertain, e.g., the construction of vectors and plasmids, the insertion of genes encoding polypeptides into such vectors and plasmids, or the introduction of vectors and plasmids into host cells. Such methods are described in detail in numerous publications including, for example, Sambrook et al., *Molecular Cloning: A Laboratory Manual*, Cold Spring Harbor Laboratory Press (1989); Ausubel et al. (Eds.), *Current Protocols in Molecular Biology*, John Wiley & Sons, Inc. (1994); and Ausubel et al. (Eds.), *Short Protocols in Molecular Biology*, 4th ed., John Wiley & Sons, Inc. (1999).

EXAMPLE 1

Identification of a Human EST Related to Mouse parp2

Using the nucleotide sequence of mouse parp2 [National Center for Biotechnology Information (NCBI) GenBank® Accession number AJ007780 (SEQ ID NO:22)], a search of NCBI Expressed Sequence Tags (EST) database was performed to investigate the possibility that a human homologue of the mouse PARP2 gene might exist. The EST database provides 5' and/ or 3' nucleotide sequences for cDNA clones from a variety of tissue sources. The NCBI BLASTn (Basic Local Alignment Search Tool—nucleotide) program was used to compare the nucleotide query sequence of mouse PARP2 against a nucleotide sequence database and to identify DNA sequences in the human EST sequence database that have significant homology to mouse PARP2. This BLASTn search identified an EST sequence designated AA568817 (SEQ ID NO:3), cloned from human colon. Regions of homology of the EST to the mouse parp2 nucleic acid sequence were identified. Specifically, nucleotides 119 to 284 (nt 119–284) of AA568817 shared substantial homology with the antisense complement nt 1536–1701 of mouse parp2, being identical at 150 of 166 nucleotides (90% identity). Moreover, the amino acid sequence predicted from nt 128–283 of the antisense strand of AA568817 corresponded to a region consisting of amino acids 508 to 559 (aa 508–559) of the mouse PARP2 protein (SEQ ID NO:23), wherein the proteins were identical at 48 of the 52 amino acid positions (92% identity).

AA568817 was used in a search of the GenBank® database using the NCBI UniGene® program in order to identify other human EST sequences originating from the same gene. The UniGene® program assembles GenBank® sequences into a non-redundant set of gene-oriented clusters, with each cluster containing a group of sequences from the same gene. The UniGene® search of the human GenBank® database with AA568817 identified thirty-four human EST sequences belonging in the same gene cluster as AA568817. One of these human ESTs, designated R28358, (SEQ ID NO:4), was cloned from human placenta and contained 3' sequence from an I.M.A.G.E (Integrated Molecular Analysis of Genome.Expression Consortium) clone, designated 133650. I.M.A.G.E is a consortium coordinated by Lawrence Livermore National Laboratory (Livermore, Calif.) that sequences cDNAs and makes them publicly available through the American Type Culture Collection (ATCC; Rockville, Md.). R28358 was used in a search of the ATCC database to identify EST R28562 (SEQ ID NO:5) as the 5' sequenced end of I.M.A.G.E clone 133650.

R28358 was compared to the antisense sequence of mouse parp2. It was found that nt 110–240 of R28358 shared significant homology with nt 1563–1692 of mouse parp2 (108 of 128 nucleotides were identical; 84% identity). The antisense strand of R28358 (nt 110–160) was translated and the predicted protein was compared with mouse PARP2 protein (nt 1642–1692 translated to aa 543–559). This comparison revealed that the proteins were the same at 16 of the 17 corresponding amino acid positions (94% identity). R28562 was compared to mouse parp2. Nucleotides 4–186 of R28562 were found to share homology with nt 952–1134 of mouse parp2 (159 of 183 nucleotides were identical; 84% identity). When nt 4–186 of R28562 were translated and the predicted protein compared with the corresponding region of mouse PARP2 protein (nt 952–1134 translated to aa 313–373), the proteins were found to be the same at 54 of 61 corresponding amino acid positions (89% identity).

EXAMPLE 2

Isolation of Full-Length hPARP2-Encoding Polynucleotide

To clone the 5' end of human hparp2, 5' RACE analysis was performed using human Marathon™-Ready spleen and testis cDNA libraries (Clontech) as the templates. A primer corresponding to the antisense strand of EST R28562 (SEQ ID NO:6) was synthesized for use in a polymerase chain reaction with the AP1 primer (Clontech; SEQ ID NO:7) that was designed to anneal to the Marathon™ cDNA Adapters ligated to the ends of the cDNA libraries.

R28562 Antisense GTGTTGGTCCAATGGGTGT-TCTGGGCTTTGTAGCTCTG (SEQ ID NO:6)

AP1 CCATCCTAATACGACTCACTATAGGGC (SEQ ID NO:7)

The PCR reaction contained 5 μL human spleen or testis Marathon™-Ready cDNA, 0.20 μM each primer, 0.20 mM dNTPs, 1×PCR buffer, and 1 μL of Advantage® cDNA Taq Polymerase mix (Clontech). The reaction was performed in a GeneAmp® PCR System 9700 machine (PE Applied Biosystems, Norwalk, Conn.) with the following four steps: 1) 1 cycle at 94° C. for 1 min; 2) 5 cycles of 94° C. for 30 sec and 72° C. for 4 min; 3) 5 cycles of 94° C. for 30 sec and 70° C. for 4 min; and 4) 25 cycles of 94° C. for 30 sec, and 60° C. for 4 min. The PCR fragment, designated 5'-hPARP2, was isolated using gel electrophoresis and a QIAquick® Gel Extraction Kit (QIAGEN, Valencia, Calif.) according to the manufacturer's instructions.

5'-hPARP2 was cloned directly into pCR®2.1-TOPO vector (Invitrogen, Carlsbad, Calif.), according to the manufacturer's instructions. Because Taq polymerase has an error rate of $8.0 \times 10^{-6}$ mutation/base pair [Cline et al., *Nucleic Acids Res* 24(18):3546–51 (1996)], four unique clones were sequenced and compared to eliminate the possibility of Taq polymerase-induced errors in the sequence of 5'-hPARP2. The four clones were determined to be unique by their different lengths. The differences in the lengths of the four clones indicated that they were amplified from unique clones in the Marathon™ libraries.

The four unique clones of 5'-hPARP2 were sequenced with primers that hybridized to the vector DNA:

M13 Forward   TGTAAAACGACGGCCAGT   (SEQ ID NO:8)

M13 Reverse   GGAAACAGCTATGACCATG   (SEQ ID NO:9)

and primers designed to anneal to the cDNA sequence:

3-P2-SEQ1   GGCTGTACACTCTGGGTCCACAGGAGC   (SEQ ID NO:10)

3-P2-SEQ2   CTTCCATGAGAGCTCGTCCATGCTGGCC   (SEQ ID NO:11)

5-P2-SEQ2   GGCCAGCATGGACGAGCTCTCATGGAAG   (SEQ ID NO:12).

The four individual nucleotide sequences were compiled into a consensus nucleotide sequence designated 5'-hPARP2 (SEQ ID NO:13). In the consensus nucleotide sequence of 5'-hPARP2, every base pair was present at the corresponding position in three of the four unique clones, except consensus sequence nucleotides 625, 632, and 881, which were present in two of the four unique clones.

To confirm that nucleotides 625, 632, and 881 of the 5'-hPARP2 consensus sequence were correct, two separate PCR reactions were performed using the Marathon™-Ready human testis cDNA library (Clontech) as the template. A primer corresponding to the sense strand of 5'-hPARP2 (5-P2-SEQ1; SEQ ID NO:14) and primers corresponding to the antisense strand of EST R28358 (designated hPARP2 L1 (SEQ ID NO:15) and hPARP2 L2 (SEQ ID NO:16)) were used in PCR reactions under the conditions described previously.

5-P2-SEQ1 GCTCCTGTGGACCCAGAGTGTA-CAGCC (SEQ ID NO:14)

hPARP2 L1 ACATTCACCACAGCTGAAGG (SEQ ID NO:15)

hPARP2 L2 CCACAGCTGAAGGAAATTAAAC (SEQ ID NO:16)

The PCR fragments, designated P2-1 (amplified with 5-P2-SEQ1 and hPARP2 L1) and P2-9 (amplified with 5-P2-SEQ1 and hPARP2 L2), were isolated using gel electrophoresis and a QIAquick®. Gel Extraction Kit (QIAGEN) according to the manufacturer's instructions. P2-1 and P2-9 were cloned directly into the pCR®2.1-TOPO vector (Invitrogen) according to the manufacturer's instructions. P2-1 and P2-9 were sequenced with the M13 Forward and M13 Reverse primers that hybridize to the vector DNA (SEQ ID NOs:8 and 9, respectively) and the partial nucleotide sequences of P2-1 and P2-9 are set out in SEQ ID NO:17 and SEQ ID NO:18, respectively. Nucleotides 625, 632, and 881 of the 5'-hPARP2 consensus sequence were determined to be present in clones P2-1 and P2-9 (nucleotides 267, 274, and 523, respectively), and thus, determined to be correct. 5'-hPARP2 was determined to have an open reading frame (ORF) of 1080 nucleotides beginning at nucleotide 63. The deduced amino acid sequence from nucleotides 63–1142 of 5'-hPARP2 is set out in SEQ ID NO:19.

To clone the 3' end of human hparp2, two separate PCR reactions were performed using the Marathon™-Ready human testis cDNA library (Clontech) as the template. A primer corresponding to the sense strand of 5'-hPARP2 (5-P2-SEQ2; SEQ ID NO:14) and primers corresponding to the antisense strand of EST R28358 (hPARP2 L1, SEQ ID NO:15; hPARP2 L2, SEQ ID NO:16) were used in PCR reactions under the conditions described previously. The PCR fragments, designated 3'-hPARP2-L1 (amplified with 5-P2-SEQ2 and hPARP2 L1) and 3'-hPARP2-L2 (amplified with 5-P2-SEQ2 and hPARP2 L2), were isolated using gel electrophoresis and a QIAquick® Gel Extraction Kit (QIAGEN) according to the manufacturer's instructions.

3'-hPARP2-L1 and 3'-hPARP2-L2 were cloned directly into the pCR®2.1-TOPO vector (Invitrogen) according to the manufacturer's instructions. Four clones of 3'-hPARP2-L1 and three clones of 3'-hPARP2-L2 were sequenced with primers that hybridized to the vector DNA (SEQ ID NO:8 and SEQ ID NO:9) to eliminate the possibility of Taq polymerase-induced errors in the sequence of 3'-hPARP2 as discussed above. The seven nucleotide sequences were compiled into a consensus nucleotide sequence, designated 3'-hPARP2, which is set out in SEQ ID NO:20.

Every base pair in the consensus nucleotide sequence of 3'-hPARP2 was present at the corresponding position in at least six of the seven clones used to compile the consensus, except nt 856–864, which were present in at least three of the 7 clones. However, the consensus sequence of nt 856–864 of 3'-hPARP2 was present in EST R28358, and thus, was determined to be correct. Nucleotides 1–193 of 3'-hPARP2 were determined to overlap with 5'-hPARP2 (nt 951–1143). 3'-hPARP2 had 671 additional nucleotides located 3' to the overlapping region (nt 194–864). 3'-hPARP2 was determined to have an ORF of 861 nucleotides beginning at nt 1, with a stop codon beginning at nt 862. The amino acid sequence deduced from nt 1–861 of 3'-hPARP2 is set out in SEQ ID NO:21.

5'-hPARP2 (nt 1–1143) was joined with 3'-hPARP2(nt 194–864), and the resultant polynucleotide sequence was designated "hparp2" (human parp2) and is set out in SEQ ID) NO:1. A comparison of the hparp2 and mouse parp2 (SEQ ID NO:22) sequences revealed that nt 306–728 of hparp2 shared substantial homology with nt 199–621 of mouse parp2 (374 of 423 nucleotides were identical; 88% identity). In addition, nt 744–1814 of hparp2 shared substantial homology with nt 625–1695 of mouse parp2 (943 of 1071 nucleotides were identical; 88% identity).

hparp2 was determined to have an ORF of 1789 nucleotides beginning at nt 63 and to have a stop codon beginning at nt 1812. The ATG beginning at nt 63 was determined to be the initiating methionine codon by the presence of upstream in frame stop codons. The deduced amino acid sequence from nt 63–1811 of hparp2 is set out in SEQ ID NO:2. hPARP2 and mouse PARP2 (SEQ ID NO:23) were the same at 489 of 558 amino acid residues (88% identity). Twenty-six amino acid residue gaps in the alignment were present: hPARP2 amino acid residues 8, 14, 45–48, 58, 68–81, and 223–226 did not align with mouse PARP2; and mouse PARP2 residue 34 did not align with hPARP2.

The human parp1 gene (SEQ ID NO:24) encodes a protein hPARP1 (SEQ ID NO:25) containing a 46 kDa amino-terminal DNA binding domain (aa 1–373 of SEQ ID NO:25) that includes two zinc-finger motifs and a nuclear localization signal [see Molinete et al., "Structure and function of the human poly(ADP-ribose) polymerase," *ADP-Ribosylation Reactions*, Poirier and Moreau (Eds.), Springer-Verlag, New York, 1992, at pp. 3–13]. hPARP2 does not contain an obvious zinc-finger DNA binding domain, but it may contain a different, yet unidentified, DNA binding domain. hPARP2 may also interact with DNA indirectly by binding to a DNA binding protein. It is also possible that hPARP2 does not interact directly or indirectly with DNA.

hPARP1 contains a central 22 kDa automodification domain (aa 373–525 of SEQ ID NO:25) that contains 15 glutamic acid residue sites, of which some or all maybe sites for automodification [Pieper et al., *Trends Pharmacol Sci* 20:171–81 (1999)]. The automodification domain of hPARP1 does not align with hPARP2, but hPARP2 does contain 44 glutamic acid residues that may be sites for automodification.

hPARP1 contains a carboxyl terminal 40 kDa catalytic domain (aa 655–1014 of SEQ ID NO:25) [Molinete et al., supra]. When aa 224–583 of hPARP2 (SEQ ID NO:2) are aligned with aa 655–1014 of hPARP1, 145 of 364 amino acids are the same (40% identity). A "G-X-X-X-G-K-G" motif (SEQ ID NO:68) involved in catalytic activity also is conserved between hPARP1 (aa 888–894 of SEQ ID NO:25) and hPARP2 (aa 454–460 of SEQ ID NO:2).

EXAMPLE 3

Measurement of hPARP2 Biological Activity

PARP1 has endogenous poly(ADP) polymerase activity that is activated when PARP1 is bound to damaged DNA. This activation can be readily assayed due to the presence of an automodification domain in hPARP1 [see, e.g., Nishikimi et al., *J Biol Chem* 257:6102–5 (1982)]. The structural similarity of hPARP2 to hPARP1 suggests that hPARP2 will also possess poly(ADP) polymerase activity. However, structural differences in the amino terminal half-of the molecules make it uncertain whether hPARP2 will be 1) activated by DNA damage, or 2) a target of automodification.

The activation of hPARP2 by DNA can be readily assessed by employing methods developed for the measurement of polymerase activity by PARP1 in the presence or absence of DNA [see, e.g., Benjamin and Gill, *J Biol Chem* 255:10502–8 (1980); Yoshihara, *Biochem Biophys Res Commun* 47:119–25 (1972)]. DNA samples may be prepared to contain single stranded or double stranded DNA, closed circular DNA, or linear DNA, with blunt, 3'-recessed, or 5'-recessed ends. The automodification of hPARP2 can readily be determined by measurement of incorporation of ADP-ribose into forms covalently attached to the hPARP2 protein using methods developed for PARP1 [e.g., Banasik et al., supra].

Alternatively, one method for the determination of hPARP2 catalytic activity, in the absence of information regarding DNA binding activity or automodification activity, is to substitute the catalytic region of hPARP2 for the catalytic region of hPARP1 in the hPARP1 cDNA. This can be accomplished using the standard tools of molecular biology. The expression and purification of such a chimeric protein allows the assessment of hPARP2 catalytic activity in a context that is independent of hPARP2-specific activation or substrates. In this case, the DNA-binding domain of hPARP1 may permit DNA-dependent activation of the hPARP2 catalytic domain. Likewise, the automodification domain of HPARP1 may serve as a target of hPARP2-mediated ADP-ribosylation.

If the ability of hPARP2 to automodify either in the form of native polypeptide or chimeric polypeptide is undetectable or difficult to detect, an alternative approach is to add to the assay heterologous proteins that might be expected to serve as a target of ADP-ribosylation [e.g., Tsopanakis et al., *Eur J Biochem* 90:337–45 (1978)].

Further characterization of biological activities of hPARP2 can also be obtained by ectopic expression of the hPARP2 polypeptide. Ectopic expression can be induced, for example, by transfection of hPARP2 expression vectors into cultured cell lines. Analysis of the phenotype of transiently or stably transfected cell lines can be used for the determination of biological function. Such experiments are common in the art [see, e.g., Fritz et al., *Mutation Res* 308:127–33 (1994)]. Conversely, targeted disruption of hPARP2 expression or activity by, for example, the use of gene activation, antisense oligonucleotides, or hPARP2-specific chemical inhibitors, can be used for the identification of hPARP2-specific biological function.

Construction of Baculovirus Expression Plasmids

The primary structure of the hparp2 polypeptide suggests that hPARP2, like hPARP1, will have poly(ADP-ribose) polymerase activity. The PARP activity of hPARP2, or some substructure thereof, can be measured by the ability of that component to incorporate the ADP-ribose unit from NAD into polymers of ADP-ribose coupled to a protein substrate. The demonstration of such activity on a given substrate is readily accomplished by the skilled artisan [see, for example, Smith et al., *Science* 282:1484–1487 (1998)].

A fusion protein, designated PARP1A/PARP2B, containing aa 1–662 of hPARP1 (SEQ ID NO:25) fused upstream of aa 230–583 of hPARP2 (SEQ ID NO:2) was used in the measurement of hPARP2 poly(ADP-ribose) polymerase activity. PARP1A/PARP2B contained the DNA binding domain (aa 1–373 of SEQ ID NO:25) and automodification domain (aa 373–525 of SEQ ID NO:25) of hPARP1 and the putative catalytic domain of hPARP2 (aa 224–583 of SEQ ID NO:2).

The PARP1A piece of the fusion protein was amplified by PCR using a primer (Sal-PARP1; SEQ ID NO:26) corresponding to the sense strand of hparp1 polynucleotide sequence (nt 1–30 of SEQ ID NO:24) and a primer (revMlu-PARP1; SEQ ID NO:27) corresponding to the antisense strand of hparp1 polynucleotide sequence (nt 1957–1985 of SEQ ID NO:24).

Sal-PARP1 CGTCGACCCATGGCGGAGTCTTCG-GATAAGCTCTATCGA (SEQ ID NO:26)

revMlu-PARP1 GGAAACGCGTTTGGTGCCAGGATT-TACTGTCAGCTTCTT (SEQ ID NO:27)

The PCR reaction contained 0.5 µL of human thymus or testis QUICK-Clone™ cDNA (Clontech), 0.25 µM each primer, 0.20 mM dNTPs, 1×PCR buffer, and 1 µL of Clontech Advantage® polymerase mix. The reactions were performed in a GeneAmp® PCR System 9700 machine (PE Applied Biosystems) with the following steps: 1) 1 cycle at 94° C. for 1 min; 2) 30 cycles of 94° C. for 30 sec, 60° C. for 2 min, and 72° C. for 2 min; and 3) 1 cycle at 72° C. for 7 min. The PCR fragment (designated hparp1A) was isolated using gel electrophoresis and a QIAquick® Gel Extraction Kit (QIAGEN) according to the manufacturer's instructions. hparp1A was subcloned into the pTrcHis2™-Topo™ vector (Invitrogen) according to the manufacturer's instructions. hparp1A was digested from pTrcHis2™-Topo™ with SalI and MluI, the fragment isolated using gel electrophoresis and a QIAquick® Gel Extraction Kit (QIAGEN), and saved for further subcloning described below.

The PARP2B piece of the fusion protein was amplified by PCR using a primer (forMlu-PARP2; SEQ ID NO:28) corresponding to the sense strand of hparp2 polynucleotide sequence (nt 750–776 of SEQ ID NO:1) and a primer (PARP2-Strep-Not; SEQ ID NO:29) corresponding to the antisense strand of hparp2 polynucleotide sequence (nt 1771–1811 of SEQ ID NO:1).

forMlu-PARP2 TTGAAACGCGTTCCAGAGTCA-CAGCTAGATCTTCGGGTA (SEQ ID NO:28)

PARP2-Strep-Not GTCTCGAAAGCGGCCGCTTAGC-CTCCGAACTGTGGATGC

CTCCACGCCCACAGCTGAAGGAAAT-TAAACTGAACCTTTAAAAGGTACC (SEQ ID NO:29)

The PCR reaction contained 100 ng hparp2 cDNA, 0.25 µM each primer, 0.20 mM dNTPs, 1×PCR buffer, and 1 µL of Clontech Advantage® polymerase mix. The reactions were performed in a GeneAmp® PCR System 9700 machine (PE Applied Biosystems) with the following steps: 1) 1 cycle at 94° C. for 1 min; 2) 30 cycles of 94° C. for 30 sec, 60° C. for 2 min, and 72° C. for 2 min; and 3) 1 cycle at 72° C. for 7 min. The PCR fragment (designated hparp2B) was isolated using gel electrophoresis and a QIAquick® Gel Extraction Kit (QIAGEN) according to the manufacturer's instructions. The hparp2B fragment was cloned into the pcDNA3.1/NT-GFP-TOPO™ vector (Invitrogen) according to the manufacturer's instructions.

hparp2B was digested from pcDNA3.1/NT-GFP-TOPO™ with MluI and NotI and subcloned with SalI/MluI digested hparp1A (see above) into a pFASTBAC vector (Gibco BRL, Rockville, Md.) that had previously been digested with SalI and NotI. The resultant plasmid was designated pFB-PARP1A/PARP2B.

pFB-PARP1A/PARP2B was sequenced with primers designed to anneal to the vector sequence (SEQ ID NOs:30 and 31) and primers designed to anneal to the cDNA sequence (SEQ ID NOs:6, 11, and 32–45).

Vector primers for PARP1A/PARP2B

FastBac for TTTGTTCGCCCAGACTC (SEQ ID NO:30)

FastBac rev TATGTTTCAGGTTCAGGGGGAG (SEQ ID NO:31)

cDNA Primers for PARP1A/PARP2B

| P1 | GCGGAAGCTGGAGGAGTGAC | (SEQ ID NO:32) |
|---|---|---|
| P2 | GTCACTCCTCCAGCTTCCGC | (SEQ ID NO:33) |
| P3 | AAGCCCTGAAGAAGCAGCTC | (SEQ ID NO:34) |
| P4 | GAGCTGCTTCTTCAGGGCTT | (SEQ ID NO:35) |
| P5 | CAGACACCCAACCGGAAGGA | (SEQ ID NO:36) |
| P6 | TCCTTCCGGTTGGGTGTCTG | (SEQ ID NO:37) |
| P7 | TCCGCCTCCACCAAGAGCCT | (SEQ ID NO:38) |
| P8 | AGGCTCTTGGTGGAGGCGGA | (SEQ ID NO:39) |
| P9 | TGGCCTGGTGGACATCGTTA | (SEQ ID NO:40) |
| P10 | TAACGATGTCCACCAGGCCA | (SEQ ID NO:41) |
| 3-P2-SEQ2 | CTTCCATGAGAGCTCGTCCATGCTGGCC | (SEQ ID NO:11) |
| 3-PARP2 | GTGTTGGTCCAATGGGTGTTCTGGGCTTTGTAGCTCTG | (SEQ ID NO:6) |
| AA#5 | GTATTCTTTAGGCGAGAGGC | (SEQ ID NO:42) |
| H23985-5 | TGACGAAGTGGGCAGAACTG | (SEQ ID NO:43) |
| PARP2U2 REV | GAGCACCCCCTGGACCAGCAC | (SEQ ID NO:44) |
| AA#3 | ACAGCGACTATACCATGACC | (SEQ ID NO:45) |

The nucleotide sequence of PARP1A/PARP2B is set out in SEQ ID NO:46, and the amino acid sequence of PARP1A/PARP2B is set out in SEQ ID NO:47. PARP1 A/PARP2B consists of the following regions: a His tag leader region at aa 1–36; a hPARP1 region at aa 37–698; a spacer region from amino acids 699 to 700; a hPARP2 region at aa 701–1054; and a Strep-tag region at aa 1055–1063.

In addition to PARP1A/PARP2B, a full-length hPARP2 protein fused to a poly-His tag (FB-hPARP2) was constructed for use in the measurement of hPARP2 poly(ADP-ribose) polymerase activity. The construction of FB-hPARP2 was carried out as follows.

A carboxyl region of hparp2 was isolated by digesting the pFB-PARP1A/PARP2B plasmid with SalI and SacI to remove the hPARP1 region. This hPARP2 region (pFB-PARP2B-Sal/Sac) was isolated using gel electrophoresis and a QIAquick® Gel Extraction Kit (QIAGEN) and saved for further subcloning described below.

An amino terminal region of hPARP2 was amplified by PCR using a primer (Sal-PARP2; SEQ ID NO:48) corresponding to the sense strand of hparp2 polynucleotide sequence (nt 63–92 of SEQ ID NO:1) and a primer (revMlu-PARP2; SEQ ID NO:49) corresponding to the antisense strand of hparp2 polynucleotide sequence (nt 720–748 of SEQ ID NO:1).

Sal-PARP2 CGTCGACCCATGGCGGCGCGGCGGC-GACGGAGCACCGGC (SEQ ID NO:48)

revMlu-PARP2 TGGAACGCGTTTCAAGGGAGATT-TAAGAGATTCCTCTTT (SEQ ID NO:49)

The PCR reaction contained 100 ng of hparp2 cDNA, 0.25 μM each primer, 0.20 mM dNTPs, 1×PCR buffer, and 1 μL of Clontech Advantage® polymerase mix. The reactions were performed in a GeneAmp® PCR System 9700 machine (PE Applied Biosystems) with the following steps: 1) 1 cycle at 94° C. for 1 min; 2) 30 cycles of 94° C. for 30 sec, 60° C. for 2 min, and 72° C. for 2 min; and 3) 1 cycle at 72° C. for 7 min. The PCR fragment (designated hparp2-Sal/Mlu) was isolated using gel electrophoresis and a QIAquick® Gel Extraction Kit (QIAGEN) according to the manufacturer's instructions. hparp2-Sal/Mlu was subcloned into the pTrcHis2™-Topo™ vector (Invitrogen) according to the manufacturer's instructions. The resultant plasmid, pTrcHis2-hparp2-Sal/Mlu, was digested with SalI and AvaII, and an hparp2 fragment (designated hparp2-Sal/Ava) was isolated using gel electrophoresis and a QIAquick® Gel Extraction Kit (QIAGEN) and saved for further subcloning described below.

A central region of hparp2 was isolated from hparp2 cDNA by digesting with AvaII and SacI. The fragment (designated hparp2-Ava/Sac) was isolated using gel electrophoresis and a QIAquick Gel Extraction Kit (QIAGEN).

pFB-PARP2B-Sal/Sac, hparp2-Sal/Ava, and hparp2-Ava/Sac were ligated to produce pFB-hparp/Strep-tag. The Strep-tag was removed from pFB-hparp/Strep-tag by digestion with KpnI, yielding a plasmid designated pFB-hparp-Kpn. The KpnI digestion also removed the last 14 amino acids of hPARP2. To replace this missing region, a fragment was PCR amplified using a primer (5-P2-Kpn; SEQ ID NO:50) corresponding to the sense strand of hparp2 polynucleotide sequence (nt 1757–1776 of SEQ ID NO:1) and a primer (3-P2-Kpn; SEQ ID NO:5 1) corresponding to the antisense strand of hparp2 polynucleotide sequence (nt 1799–1814 of SEQ ID NO:1).

5-P2-Kpn CCAGGTCCGTATGCGGTACC (SEQ ID NO:50)

3-P2-Kpn GCCACGATGGGTACCGCGGCCGCTCAC-CACAGCTGAAGG (SEQ ID NO:51)

The PCR reaction contained 100 ng hparp2 cDNA, 0.5 μM each primer, 0.25 mM dNTPs, 1×PCR buffer, and 2.5 U of PfuTurbo® polymerase mix (Stratagene). The reactions were performed in a GeneAmp® PCR System 9700 machine (PE Applied Biosystems) with the following steps: 1) 1 cycle at 94° C. for 1 min; 2) 25 cycles of 94° C. for 30 sec, 55° C. for 30 sec, and 72° C. for 30 sec; and 3) 1 cycle at 72° C. for 7 min. The PCR fragment was digested with KpnI, isolated using gel electrophoresis and a QIAquick® Gel Extraction Kit (QIAGEN), and ligated with pFB-hparp-Kpn to produce pFB-hparp2.

pFB-hparp2 was sequenced with primers designed to anneal to the vector sequence (SEQ ID NOs:30 and 31) and primers designed to anneal to the cDNA sequence (SEQ ID NOs:11, 12, 42, and 52–57).

cDNA Primers for pFB-hparp2

|  |  |  |
|---|---|---|
| 3-P2-SEQ2 | CTTCCATGAGAGCTCGTCCATGCTGGCC | (SEQ ID NO:11) |
| 5-SEQ-2 | GGCCAGCATGGACGAGCTCTCATGGAAG | (SEQ ID NO:12) |
| AA#5 | GTATTCTTTAGGCGAGAGGC | (SEQ ID NO:42) |
| AA#1 | GGTGACGAAGTGGGCAGAAC | (SEQ ID NO:52) |
| AA#2 | TTCTGCCCACTTCGTCACCC | (SEQ ID NO:53) |
| AA#4 | CGCAAGGCACAATGTAGGTT | (SEQ ID NO:54) |
| AA#6 | GCCTCTCGCCTAAAGAATAC | (SEQ ID NO:55) |
| H2 | AAGCAATCCTTCGGCCTTAG | (SEQ ID NO:56) |
| H6 | AGTTCTGCCCACTTCGTCAC | (SEQ ID NO:57) |

The nucleotide sequence of pFB-hparp2 is set out in SEQ ID NO:58 and the corresponding amino acid sequence of FB-hPARP2 is set out in SEQ ID NO:59. FB-hPARP2 contains a His tag leader region at aa 1–36. Amino acids 37–619 of FB-hPARP2 represent full-length hPARP2.

Production of Recombinant Viral Stocks and Protein Purification

PARP1 A/PARP2B and FB-hPARP2 recombinant viral stocks were separately produced using the FastBac system (Gibco BRL) according to the manufacturer's suggested protocol and protein expression was carried out as follows. Sf9 cells were grown at 27° C. in CCM3 medium (Hyclone, Logan, Utah) containing 50 U/mL penicillin and 50 µg/mL streptomycin sulfate (Gibco BRL). Exponentially growing cells were infected at a multiplicity of infection of approximately 0.5 virus per cell and incubated for 48 hr. Cells were collected by centrifugation at 1000×g for 15 min, and the pellets were frozen and stored at −80° C. until use.

For protein purification, reagents were obtained from Sigmna (St. Louis, Mo.), unless otherwise indicated. Cells were lysed in Lysis buffer (25 mM Tris-HCl, pH 9.0, 50 mM glucose, 10 mM EDTA, 1 mM 2-mercaptoethanol, 1 mM PMSF, 100 µM antipain, and 2 µg/mL aprotinin) by sonication. Igepal CA-630 (final concentration of 0.2%), Tween®-20 (final concentration of 0.2%), and NaCl (final concentration of 0.5 M) were added to the Lysis buffer and the samples were agitated for 30 min at 4° C. The supernatants were collected after centrifugation at 20,000×g for 20 min at 4° C. at which time they were treated with 1 mg/mL protamine sulfate and allowed to stir for 1 hr at 4° C. The supernatants were collected after centrifugation at 4,000×g for 20 min at 4° C. at which time the protein was precipitated with 70% ammonium sulfate for 1 hr at 4° C. Protein pellets were collected by centrifugation at 20,000×g for 15 min at 4° C. and resuspended in Re-suspension buffer (100 mM Tris-HCl, pH 7.4, 0.5 mM EDTA, 10% glycerol, 1 mM PMSF, and 12 mM 2-mercaptoethanol).

Proteins were first purified via the His tag using TALON™ Superflow Metal Affinity Resin (Clontech) and eluted with 200 mM imidazole (Clontech) according to the manufacturer's instructions. The protein elutions were next purified using a 3-aminobenzamide Affi-Gel® matrix (Bio-Rad Laboratories) prepared as described elsewhere [D'Amours et al., Anal Biochem 249:106–8 (1997)]. Proteins were eluted with 10 mM 3-methoxybenzamide in Elution buffer (50 mM Tris-HCl, pH 7.5, 0.3 M NaCl, 10 mM 2-mercaptoethanol, 1 mM PMSF, 100 µM antipain, and 2 µg/mL aprotinin). The proteins were dialyzed 4×in 1 L Dialysis buffer (50 mM Tris-HCl, pH 8.0, 1 mM dithiothreitol, 4 mM MgCl$_2$, 10 mM EDTA, 1 mM PMSF, and 2 µg/mL aprotinin). Glycerol was added to a final concentration of 10% and the proteins were stored at −80° C.

Poly(ADP-ribose) Polymerase Activity

For poly(ADP-ribose) polymerase activity assays, reagents were obtained from Sigma, unless otherwise indicated. PARP1A/PARP2B (250 ng) or FB-hPARP2 (25 ng) protein was incubated for 10 min at room temperature in assay buffer (total volume of 20 µL) containing 100 mM Tris, pH 8.0, 1 mM MgCl$_2$, 10% glycerol, 1.5 mM dithiothreitol (Boehringer Mannheim/Roche Molecular Biochemicals, Indianapolis, Ind.), 2.5 µM unlabeled NAD$^+$, 16.7 µg/mL E. coli Strain B DNA, and 0.33 µCi gamma-[$^{32}$P]-NAD$^+$ (NEN, Boston, Mass.). Reactions were stopped by boiling in SDS running buffer and separated by SDS-polyacrylamide gel electrophoresis (SDS-PAGE). Autoradiography was used to visualize labeled protein. Addition of poly(ADP-ribose) polymers to protein substrate results in an increase in molecular weight of the protein, and subsequently causes the protein to run higher on SDS-PAGE. Also, the level of poly(ADP-ribose) polymers added to the protein substrate can vary with each single protein molecule, resulting in labeled protein with different molecular weights and visualized on the autoradiography film as a ladder or smear [for example, see Smith et al. (1998), supra]. Both PARP1A/PARP2B and FB-hPARP2 possessed intrinsic poly (ADP-ribose) polymerase activity as shown by their ability produce poly(ADP-ribose) polymers. The PARP1A/PARP2B poly(ADP-ribose) polymerase reaction produced a ladder of labeled protein approximately from 174 kDa to 200 kDa. The FB-hPARP2 poly(ADP-ribose) polymerase reaction produced a ladder of labeled protein approximately from 136 kDa to 250 kDa.

EXAMPLE 4

Preparation of Antibodies Immunoreactive with hPARP2 Polypeptides

The present invention provides for antibodies with specificity for hPARP2 polypeptides. Antibodies to hPARP2 may be produced by any method known in the art, typically including, for example, the immunization of laboratory animals with preparations of purified native hPARP2, purified recombinant hPARP2, purified recombinant peptide fragments of hPARP2, or synthetic peptides derived from the hPARP2 predicted amino acid sequence. In order to maximize the probability of obtaining antibodies with appropriate specificity for hPARP2, regions of the polypeptide may be selected for use as an immunogen based upon differences in those regions between hPARP1 and hPARP2. For example, amino acid residues 1–86 are substantially different between hPARP1 and hPARP2, and this region can be expressed as a truncated polypeptide in an appropriate expression system for use as an immunogen or to test polyclonal or monoclonal antibody preparations. Similar approaches can be applied to other regions of the hPARP2 polypeptide. Likewise, synthetic peptides can be made corresponding to selected regions of hPARP2, and such peptides can be used to generate specific polyclonal or monoclonal antibodies by methods known in the art [see, e.g., Harlow et al., supra].

Two regions in the carboxyl region of hPARP2 (designated hPARP2 U1 and hPARP2 U2) were chosen as immunogens in antibody development. hparp2 U1 was amplified by PCR using a primer (5-PARP2 U1; SEQ ID NO:60) corresponding to the sense strand of hparp2 polynucleotide sequence (nt 1074–1093 of SEQ ID NO:1) and a primer (PARP2 L2; SEQ ID NO:16) corresponding to the antisense strand of hparp2 polynucleotide sequence (nt 1790–1811 of SEQ ID NO:1). hparp2 U2 was amplified by PCR using a primer (5-PARP2 U2; SEQ ID NO:61) corresponding to the sense strand of hparp2 polynucleotide sequence (nt 1125–1145 of SEQ ID NO:1) and the same antisense primer (PARP2 L2; SEQ ID NO:16) used for hparp2 U1.

5-PARP2 U1 GGAGACATTGAAATTGCTAT (SEQ ID NO:60)

5-PARP2 U2 GAACACCCATTGGACCAACAC (SEQ ID NO:61)

The PCR reaction contained 100 ng hparp2 cDNA, 0.5 μM each primer, 0.25 mM dNTPs, 1×PCR-buffer, and 2.5 U of PfuTurbo® polymerase mix (Stratagene). The reactions were performed in a GeneAmp® PCR System 9700 machine (PE Applied Biosystems) with the following steps: 1) 1 cycle at 94° C. for 1 min; 2) 25 cycles of 94° C. for 30 sec, 55° C. for 2 min, and 72° C. for 2 min; and 3) 1 cycle at 72° C. for 7 min. The PCR fragments were subcloned into the pTrcHis2™-Topo™ vector (Invitrogen) according to the manufacturer's instructions. hparp2 U1 and hparp2 U2 were sequenced with primers designed to anneal to the vector (SEQ ID NOs:62 and 63).

pTrcHis Forward GAGGTATATATTAATGTATCG (SEQ ID NO:62)

pTrcHis Reverse GATTTAATCTGTATCAGG (SEQ ID NO:63)

The polynucleotide sequence of hparp2 U1 is set out in SEQ ID NO:64 and the amino acid sequence (hPARP2 U1) is set out in SEQ ID NO:65. hPARP2 U1 includes aa 338–583 of hPARP2 (SEQ ID NO:2). The polynucleotide sequence of hparp2 U2 is set out in SEQ ID NO:66 and the amino acid sequence (hPARP2 U2) is set out in SEQ ID NO:67. hPARP2 U2 includes aa 355–583 of hPARP2 (SEQ ID NO:2).

hPARP2 U1 and hPARP2 U2 poly-His fusion proteins were expressed separately in *E. coli* and were induced with 1 mM IPTG at 37° C. hPARP2 U1 and hPARP2 U2 proteins were isolated from inclusion bodies using B-PER™ Bacterial Protein Extraction Reagent (Pierce, Rockford, Ill.) according to the manufacturer's instructions.

Each of five 6 to 12 week old Balb/c mice were pre-bled on day 0 and injected with 30 μg per mouse of a mixture of hPARP2 U1 and hPARP2 U2 in Freund's complete adjuvant. Subsequent boosts were made on day 21 and 63 in Freund's incomplete adjuvant. Mice were test bled on day 73 and the bleeds were screened by ELISA, using standard methods, on plates coated with PARP1A/PARP2B (described above). Specific antibody was detected using goat anti-mouse IgG (fc) horseradish peroxidase conjugate.

ELISA reactive mouse sera are tested in Western analysis using standard methods. The spleens of mice reactive to FB-hPARP2 protein in the Western analysis are removed, and fused to NS-1 cells by standard methods [Harlow and Lane,

*Antibodies, a Laboratory Manual*, Cold Spring Harbor Laboratory (1988)] to produce monoclonal antibodies.

All publications and patent documents cited in this specification are incorporated herein by reference for all that they disclose.

While the present invention has been described with specific reference to certain preferred embodiments for purposes of clarity and understanding, it will be apparent to the skilled artisan that further changes and modifications may be practiced within the scope of the invention as it is defined in the claims set forth below. Accordingly, no limitations should be placed on the invention other than those specifically recited in the claims.

What is claimed is:

1. An isolated polynucleotide encoding the human poly (ADP-ribose) polymerase 2 (hPARP2) polypeptide comprising the amino acid sequence defined by SEQ ID NO:2.

2. A method for producing a polypeptide having an amino acid sequence defined by SEQ ID NO: 2, comprising the steps of:
   a) growing a host cell transformed or transfected with an expression construct comprising the polynucleotide defined by SEQ ID NO: 1 under conditions appropriate for expression of the polypeptide; and
   b) isolating the polypeptide from the host cell or the medium in which the host cell is grown.

3. A method for producing a polypeptide having an amino acid sequence defined by SEQ ID NO: 2, comprising the steps of:
   a) growing a host cell transformed or transfected with an expression construct comprising the polynucleotide defined by SEQ ID NO: 1 operatively linked to a heterologous promoter, under conditions appropriate for expression of the polypeptide; and
   b) isolating the polypeptide from the host cell or the medium in which the host cell is grown.

* * * * *

UNITED STATES PATENT AND TRADEMARK OFFICE
CERTIFICATE OF CORRECTION

PATENT NO. : 6,599,727 B1
DATED : July 29, 2003
INVENTOR(S) : Christenson et al.

It is certified that error appears in the above-identified patent and that said Letters Patent is hereby corrected as shown below:

Title page,
Item [56], References Cited, OTHER PUBLICATIONS, "Anderson, W.F.," reference, delete "25-30.", and insert -- 25-30 (1998). --.

Column 1,
Line 54, delete "in cells, from", and insert -- in cells from --.

Column 9,
Line 38, delete "length-of", and insert -- length of --.

Column 11,
Line 11, delete "at least.80%", and insert -- at least 80% --.

Column 13,
Line 11, delete "hPARP2 can be produced and isolate from host cells", and insert -- hPARP2 can be produced and isolated from host cells --.

Column 17,
Line 6, delete "to a fragment thereof", and insert -- to a fragment thereof. --.

Column 25,
Line 7, delete "13:1014-21:1974);", and insert -- 13:1014-21 (1974); --.
Line 34, delete "phycoerythrins,.", and insert -- phycoerythrins, --.
Line 46, delete "isocyanrate,", and insert -- isocyanate, --.
Line 50, delete "carboduimides,", and insert -- carbodiimides, --.
Line 52, delete "method-", and insert -- method --.

Column 26,
Line 45, delete "(5'43 3')", and insert -- (5'→3') --.

Column 27,
Line 46, delete "(BACS);", and insert -- (BACs), --.

Column 30,
Line 6, delete "hPARP2.", and insert -- hPARP2 --.
Line 13, delete "that-specifically", and insert -- that specifically --.

Column 32,
Line 67, delete "from naturals sources", and insert -- from natural sources --.

UNITED STATES PATENT AND TRADEMARK OFFICE
CERTIFICATE OF CORRECTION

PATENT NO. : 6,599,727 B1
DATED : July 29, 2003
INVENTOR(S) : Christenson et al.

It is certified that error appears in the above-identified patent and that said Letters Patent is hereby corrected as shown below:

Column 33,
Lines 25-26, delete "typically involves of iterative series", and insert
-- typically involves an iterative series --.

Column 34,
Line 9, delete "who are or may subject to", and insert -- who are or may be subject to --.

Column 35,
Line 27, delete "T lymphocytes", and insert -- T lymphocytes --.

Column 37,
Line 43, delete "between the various. Structural elements", and insert -- between the various structural elements --.

Column 40,
Line 52, delete "where it would be preferably to block", and insert -- where it would be preferable to block --.

Column 45,
Line 49, delete "Genome.Expression", and insert -- Genome Expression --.

Column 47,
Line 23, delete "QIAquick®.Gel", and insert -- QIAquick® Gel --.
Line 24, delete "according to manufacturer's instructions. P2-1 and P2-9...", and insert -- according to manfacturer's instructions. (Begin new paragraph)P2-1 and P2-9... --.

Column 48,
Line 45, delete "maybe", and insert -- may be --.

Column 49,
Line 2, delete "half-of", and insert -- half of --.

Column 52,
Line 51, delete "NO:5 1", and insert -- NO:51 --.

Column 53,
Line 37, delete "PARP1 A", and insert -- PARP1A --.

UNITED STATES PATENT AND TRADEMARK OFFICE
CERTIFICATE OF CORRECTION

PATENT NO. : 6,599,727 B1
DATED : July 29, 2003
INVENTOR(S) : Christenson et al.

It is certified that error appears in the above-identified patent and that said Letters Patent is hereby corrected as shown below:

Column 54,
Line 20, delete "of 20 ,$\mu$L)", and insert -- of 20 $\mu$L) --.
Lines 38-39, delete "shown by their ability produce", and insert -- shown by their ability to produce --.

Column 56,
Line 24, delete "removed,", and insert -- removed --.

Signed and Sealed this

Thirtieth Day of December, 2003

JAMES E. ROGAN
*Director of the United States Patent and Trademark Office*